United States Patent
Saus

(10) Patent No.: US 6,579,969 B1
(45) Date of Patent: Jun. 17, 2003

(54) GOODPASTURE ANTIGEN BINDING PROTEIN

(76) Inventor: Juan Saus, C/Conde de Altea 8-7$^a$, 46005 Valencia (ES)

( * ) Notice: Subject to any disclaimer, the term of this patent is extended or adjusted under 35 U.S.C. 154(b) by 0 days.

(21) Appl. No.: 09/512,563

(22) Filed: Feb. 24, 2000

Related U.S. Application Data

(60) Provisional application No. 60/121,483, filed on Feb. 24, 1999.

(51) Int. Cl.$^7$ .......................... A61K 38/16; C07K 17/00
(52) U.S. Cl. ....................................... 530/324; 530/352
(58) Field of Search ............................... 530/352, 324; 424/185.1

(56) References Cited

U.S. PATENT DOCUMENTS

| | | |
|---|---|---|
| 5,424,408 A | 6/1995 | Reeders et al. |
| 5,716,622 A * | 2/1998 | Darnell, Jr. et al. |
| 5,843,646 A * | 12/1998 | Bowtell et al. |
| 5,973,120 A | 10/1999 | Reeders et al. |
| 6,007,980 A | 12/1999 | Reeders et al. |
| 6,045,997 A * | 4/2000 | Futreal et al. |

OTHER PUBLICATIONS

Aberle, H., Bauer, A., Stappert, J., Kispert, A., and Kemler, R. (1997) *EMBO J.* 16, 3797–3804.
Altschul, S.F., Madden, T.L., Schaffer, A.A., Zhang, J., Zhang, Z., Miller, W., and Lipman, D.J. (1997) *Nucleic Acids Res.* 25, 3389–3402.
Bairoch A., Bucher, P., and Hofmann, K. (1997) *Nucleic Acids Res.* 25, 217–221.
Bayer, K.–U., Löhler, J., & Harbers, K. (1996) *Mol. Cell. Biol.* 16, 29–36.
Beelers, J.F., LaRochelle, W.J., Chedid, M., Tronick, S.R., and Aaronson, S.A. (1994) Mol. Cell. Biol. 14, 982–988.
Bernal, D., Quinones, S., and Saus, J. (1993) *J. Biol Chem.* 268, 12090–12094.
Bolívar, J., Guelman, C., Iglesias, S., Ortiz, M., & Valdivia, M. (1998) *J. Biol Chem.* 273, 17122–17127.
Boulikas, T. (1993) Crit. Rev. Eukaryot. Gene Expr. 3, 193–227.
Brown, K., Gerstberger, S., Carlson, L., Franzoso, G., and Siebenlist, U. (1995) Science 267, 1485–1488.
Campagnoni, A.T. (1988) *J. Neurochem.* 51, 1–14.
Casciola–Rosen, L., & Rosen, A. (1997) *Lupus* 6, 175–180.
Casciola–Rosen, L.A., Anhalt, G. & Rosen, A. (1994) *J. Exp. Med.* 179, 1317–1330.
Casciola–Rosen, L.A., Anhalt, G.J.& Rosen, A.(1995) *J. Exp. Med.* 182, 1625–1634.
Casiano, C.A., Martin, S.J., Green, D.R., & Tan, E.M. (1996) *J. Exp. Med.* 184, 765–770.
Chen, Z.J., Parent, L., and Maniatis, T. (1996) Cell 84, 853–862.
Côté G.P., Lou, X., Murphy, M.B., and Egelhoff, T.T.(1997) J. Biol. Chem. 272, 6846–6849.

Csermely, P., and Kahn, C.R. (1991) *J. Biol. Chem.* 266, 4943–4950.
Csermely, P., Miyata, Y., Schnaider, T., and Yahara, I. (1995) J. Biol. Chem. 270, 6381–6388.
Dikstein, R., Ruppert, S., and Tjian, R. (1996) *Cell* 84, 781–790.
Eichinger, L., Bomblies, L., Vandekerckhove, J., Schleicher, M., and Gettermans, J. (1996) EMBO J. 15, 5547–5556.
Erlich, H. and Apple, R. (1998) *MHC Disease Associations. Encyclopedia of Immunology*, 2$^{nd}$ Ed., Delves, P.J. and Roitt, I.M. Eds., Academic Press Limited, London, UK, 1690–1700.
Feng, L., Xia, Y., and Wilson, C.B. (1994) *J. Biol Chem.* 269, 2342–2348.
Fraser, R.A., Heard, D.J., Adam, S., Lavigne, A.C., Le Douarin, B., Tora, L., Losson, R., Rochette–Egly, C., and Chambon, P. (1998) *J. Biol. Chem.* 273, 16199–16204.
Golan, T.D., Elkon, K.B., Ghavari, A.E.,& Krueger, J.G.(1992) *J. Clin. Invest.* 90, 1067–1076.
Green, M.R. (1986) *Ann. Rev. Genet.* 20, 671–708.
Henderson, R.D., Saltissi, D., and Pender, M.P.(1998) Acta Neurol. Scand. 98, 134–135.
Hsu, S.M., Raine, L., and Fanger, H. (1981) *J. Histochem. Cytochem.* 29, 577–580.
Kalluri et al., (1996) *J. of Biological Chem.*, 113, 9062–9068.
Langelier, Y., Champoux, L., Hamel, M., Guilbault, C., Lamarche, N., Gaudreau, P., and Massie, B.(1998) *J. Biol. Chem.* 273, 1435–1443.
Leinonen, A., Mariyama, M., Mochizuki, T., Tryggvason, K., and Reeders, S.T. (1994) *J. Biol. Chem.* 269, 26172–26177.
Lemmon, M.A., and Ferguson, K.M. (1998) *Curr. Top. Microbiol. Immunol.* 228, 39–74.
Lemmon, M.A., Falasca, M., Ferguson, K.M., and Schlessinger, J. (1997) *Trends Cell Biol.* 7, 237–242.
Litersky, J.M., and Johnson, G.V.W. (1992) J. Biol. Chem. 267, 1563–1568.
Lupas, A. (1996) *Trends Biochem. Sci.* 21, 375–382.
Madaule, P., Eda, M., Watanabe, N, Fujisawa, K., Matsuoka, T., Bito, H., Ishizaki, T., & Narumiya, S. (1998) *Nature* 394, 491–494.
Maru, Y., and Witte, O.N.(1991) *Cell* 67, 459–468.
Maruoka, Y., Harada, H., Mitsuyasu et al. (1997) *Biochem. Biophys. Res. Commun.* 238, 886–890.

(List continued on next page.)

Primary Examiner—Christina Chan
Assistant Examiner—Phuong N. Huynh
(74) Attorney, Agent, or Firm—McDonnell Boehnen Hulbert & Berghoff; David S. Harper

(57) ABSTRACT

The present invention provides isolated nucleic acid sequences and expression vectors encoding the Goodpasture antigen binding protein (GPBP), substantially purified GPBP, antibodies against GPBP, and methods for detecting GPBP.

15 Claims, 21 Drawing Sheets

OTHER PUBLICATIONS

Naito, Y., Watanabe, Y., Yokokura, H., Sugita, R., Nishio M., & Hidaka, H. (1997) *J. Biol. Chem.* 272, 32704–32708.

Pablos, J.L:, Santiago, B., Galindo, M., Carreira, P.E., Ballestin, C.& Gomez–Reino, J.J. (1999) *J. Pathol.* 188, 63–68.

Papin, C., Denouel–Galy, A., Laugier, D. Calothy, G., & Eychéne, A. (1998) *J. Biol. Chem.* 273, 24939–24947.

Penadés, J.R., Bernal, D., Revert, F., Johansson, C., Fresquet, V.J., Cervera, J., Wieslander, J., Quinones, S., and Saus, J. (1995) *Eur. J. Biochem.* 229, 754–760.

Pette, M., Fujita, K., Wilkinson, D., Altmann, D.M., Trowsdale, J., Giegerich, G., Hinkkanen, A., Epplen, J.T., Kappos, L., and Wekerle, H. (1994) *Proc. Natl. Acad. Sci. USA* 87, 7968–7972.

Phelps, R.G., Jones, V.L., Coughlan, M., Turner, A.N., and Rees, A.J. (1998) *J. Biol. Chem.* 273, 11440–11447.

Phelps, R.G., Turner, A.N., and Rees, A.J.(1996) J. Biol. Chem. 271, 18549–18553.

Polalowska, R.R., Piacentini, M.,Bartlett, R., Goldsmith, L.A., & Haake, A.R. (1994) *Dev. Dinam.* 199, 176–188.

Quinones, S., Bernal, D., García–Sogo, M., Elena, S.F., and Saus, J. (1992) *J. Biol. Chem.* 267, 19780–19784.

Raus, J. CM, en *Multiple Sclerosis : Encyclopedia of Immunology* 2$^{nd}$ edn. vol. 3(eds. Delves, P.J., & Roitt, I.M.) 1786–1789 (Academic Press Ltd., London, 1998).

Raya, A., Revert, F., Navarro, S., & Saus, J. (1999) *J. Biol. Chem.* 274, 12642–12649.

Rebecchi, M.J., and Scarlata S. (1998) *Annu. Rev. Biophys. Biomol. Struct.* 27, 503–528.

Regnier, C.H., Song, H.Y., Gao, X., Goeddel, D.V., Cao, Z., and Rothe, M. (1997) *Cell* 90, 373–383.

Revert, F., Penadés J.R., Plana, M. Bernal, D., Johansson, C., Itarte, E., Cervera, J., Wieslander, J., Quinones, S., and Saus, J. (1995) *J. Biol. Chem.* 270, 13254–13261.

Roitt, I. (1994) *Autoimmune diseases in Essential Immunology*, 383–439, 8$^{th}$ Ed., Blackwell Scientific, Oxford, UK.

Roth H.J. et al., (1987) *J. of Neuroscience Res.* 17, 321–328.

Ryazanov, A.G., Ward, M.D., Mendola, C.E., Pavur, K.S., Dorovkov. M.V., Wiedmann, M., M., Erdjument–Bromage, H., Tempst, P., Parmer, T.G., Prostko, C.R., Germino, F.J., and Hait, W.N. (1997) *Proc. Natl. Acad. Sci. USA* 94, 4884–4889.

Saus, J. (1998) in *Goodpasture's Syndrome: Encyclopedia of Immunology* 2$^{nd}$ edn. vol. 2, eds. Delves, P.J., & Roitt, I.M., (Academic Press Ltd., London), pp. 1005–1011.

Srinivasan, M., Edman, C.F., & Schulman, H. (1994) *J. Cell. Biol.* 126, 839–852.

Tsuchida, T., Parker, K.C., Turner, R.V., McFarland, H.F., Coligan, J.E., and Biddison, W.E.(1994) *Proc. Natl. Acad. Sci. USA* 91, 10859–10863.

Turner, N. et al. (1992), *J. Clin. Invest.* 89, 592–601.

Utz, P.J., & Anderson, P. (1998) *Arthritis Rheum.* 41, 1152–1160.

Vlach, J., Hennecke, S., and Amati, B. (1997) *EMBO J.* 16, 5334–5344.

Xu, W., Harrison, S.C., & Eck, M.J. (1997) *Nature* 385, 595–602.

Matumoto et al, Immunology 69(2): 215–21; Feb. 1990.*

McCarron et al, J of Immunology 141(4): 1143–9; Aug. 1988.*

Mackay et al, Allergy 41(3): 169–78; Apr. 1986.*

Fritz et al, Molecular Immunology 19(5):665–70; May 1982.*

Stryer et al., in Biochemistry (Third Edition), W.H. Freeman and Co., New York, pp. 31–33, 1988.*

Ngo et al., in The Protein Folding Problem and Tertiary Structure Prediction, Merz, et al., (ed.), Birkhauser, Boston, MA, pp. 433 and 492–495, 1994.*

Skolnick et al., From genes to protein structure and function: novel applications of computational approaches in the genomic era, Jan. 2000, Trends in Biotech. 18(1): 34–39.*

Attwood et al., The babel of bioinformatics, Oct. 2000, Science 290 (5491): 471–473.*

Mikayama et al, Molecular cloning and functional expression of a cDNA encoding gycosylation–inhibting factor, Nov. 1993, Proc. Natl. Acad. Sci, USA vol. 90: 10056–10060.*

Voet et al., Biochemistry I, 1990, pp. 126–134.*

* cited by examiner

```
GCAGGAAGATGGCGGCGGTAGCGGAGGTGTGAGTGGACGCGGGACTCAGCGGCCGGATTTTCTCTTCCCT    70

TCTTTTCCCTTTTCCTTCCCTATTTGAAATTGGCATCGAGGGGGCTAAGTTCGGGTGGCAGCGCCGGGCG   140

CAACGCAGGGGTCACGGCGACGGCGGCGGCGGCTGACGGCTGGAAGGGTAGGCTTCATTCACCGCTCGTC   210

CTCCTTCCTCGCTCCGCTCGGTGTCAGGCGCGGCGGCGGCGCGGCGGGCGGACTTCGTCCCTCCTCCTGC   280

TCCCCCCCACACCGGAGCGGGCACTCTTCGCTTCGCCATCCCCCGACCCTTCACCCCGAGGACTGGGCGC   350

CTCCTCCGGCGCAGCTGAGGGAGCGGGGGCCGGTCTCCTGCTCGGTTGTCGAGCCTCCATGTCGGATAAT   420
                                                              M  S  D  N    4

CAGAGCTGGAACTCGTCGGGCTCGGAGGAGGATCCAGAGACGGAGTCTGGGCCGCCTGTGGAGCGCTGCG   490
 Q  S  W  N  S  S  G  S  E  E  D  P  E  T  E  S  G  P  P  V  E  R  C     27

GGGTCCTCAGTAAGTGGACAAACTACATTCATGGGTGGCAGGATCGTTGGGTAGTTTTGAAAAATAATGC   560
 G  V  L  S  K  W  T  N  Y  I  H  G  W  Q  D  R  W  V  V  L  K  N  N  A   51

TCTGAGTTACTACAAATCTGAAGATGAAACAGAGTATGGCTGCAGAGGATCCATCTGTCTTAGCAAGGCT   630
  L  S  Y  Y  K  S  E  D  E  T  E  Y  G  C  R  G  S  I  C  L  S  K  A    74

GTCATCACACCTCACGATTTTGATGAATGTCGATTTGATATTAGTGTAAATGATAGTGTTTGGTATCTTC   700
  V  I  T  P  H  D  F  D  E  C  R  F  D  I  S  V  N  D  S  V  W  Y  L    97

GTGCTCAGGATCCAGATCATAGACAGCAATGGATAGATGCCATTGAACAGCACAAGACTGAATCTGGATA   770
 R  A  Q  D  P  D  H  R  Q  Q  W  I  D  A  I  E  Q  H  K  T  E  S  G  Y  121

TGGATCTGAATCCAGCTTGCGTCGACATGGCTCAATGGTGTCCCTGGTGTCTGGAGCAAGTGGCTACTCT   840
  G  S  E  S  S  L  R  R  H  G  S  M  V  S  L  V  S  G  A  S  G  Y  S   144

GCAACATCCACCTCTTCATTCAAGAAAGGCCACAGTTTACGTGAGAAGTTGGCTGAAATGGAAACATTTA   910
  A  T  S  T  S  S  F  K  K  G  H  S  L  R  E  K  L  A  E  M  E  T  F   167

GAGACATCTTATGTAGACAAGTTGACACGCTACAGAAGTACTTTGATGCCTGTGCTGATGCTGTCTCTAA   980
 R  D  I  L  C  R  Q  V  D  T  L  Q  K  Y  F  D  A  C  A  D  A  V  S  K  191

GGATGAACTTCAAAGGGATAAAGTGGTAGAAGATGATGAAGATGACTTTCCTACAACGCGTTCTGATGGT  1050
   D  E  L  Q  R  D  K  V  V  E  D  D  E  D  D  F  P  T  T  R  S  D  G   214

GACTTCTTGCATAGTACCAACGGCAATAAAGAAAAGTTATTTCCACATGTGACACCAAAAGGAATTAATG  1120
   D  F  L  H  S  T  N  G  N  K  E  K  L  F  P  H  V  T  P  K  G  I  N   237

GTATAGACTTTAAAGGGGAAGCGATAACTTTTAAAGCAACTACTGCTGGAATCCTTGCAACACTTTCTCA  1190
  G  I  D  F  K  G  E  A  I  T  F  K  A  T  T  A  G  I  L  A  T  L  S  H 261

TTGTATTGAACTAATGGTTAAACGTGAGGACAGCTGGCAGAAGAGACTGGATAAGGAAACTGAGAAGAAA  1260
   C  I  E  L  M  V  K  R  E  D  S  W  Q  K  R  L  D  K  E  T  E  K  K   284

AGAAGAACAGAGGAAGCATATAAAAATGCAATGACAGAACTTAAGAAAAAATCCCACTTTGGAGGACCAG  1330
   R  R  T  E  E  A  Y  K  N  A  M  T  E  L  K  K  K  S  H  F  G  G  P   307

ATTATGAAGAAGGCCCTAACAGTCTGATTAATGAAGAAGAGTTCTTTGATGCTGTTGAAGCTGCTCTTGA  1400
   D  Y  E  E  G  P  N  S  L  I  N  E  E  E  F  F  D  A  V  E  A  A  L  D 331
```

FIGURE 1a

```
CAGACAAGATAAAATAGAAGAACAGTCACAGAGTGAAAAGGTGAGATTACATTGGCCTACATCCTTGCCC 1470
  R  Q  D  K  I  E  E  Q  S  Q  S  E  K  V  R  L  H  W  P  T  S  L  P    354

TCTGGAGATGCCTTTTCTTCTGTGGGGACACATAGATTTGTCCAAAAGCCCTATAGTCGCTCTTCCTCCA 1540
  S  G  D  A  F  S  S  V  G  T  H  R  F  V  Q  K  P  Y  S  R  S  S  S    377

TGTCTTCCATTGATCTAGTCAGTGCCTCTGATGATGTTCACAGATTCAGCTCCCAGGTTGAAGAGATGGT 1610
  M  S  S  I  D  L  V  S  A  S  D  D  V  H  R  F  S  S  Q  V  E  E  M  V 401

GCAGAACCACATGACTTACTCATTACAGGATGTAGGCGGAGATGCCAATTGGCAGTTGGTTGTAGAAGAA 1680
  Q  N  H  M  T  Y  S  L  Q  D  V  G  G  D  A  N  W  Q  L  V  V  E  E    424

GGAGAAATGAAGGTATACAGAAGAGAAGTAGAAGAAAATGGGATTGTTCTGGATCCTTTAAAAGCTACCC 1750
  G  E  M  K  V  Y  R  R  E  V  E  E  N  G  I  V  L  D  P  L  K  A  T    447

ATGCAGTTAAAGGCGTCACAGGACATGAAGTCTGCAATTATTTCTGGAATGTTGACGTTCGCAATGACTG 1820
  H  A  V  K  G  V  T  G  H  E  V  C  N  Y  F  W  N  V  D  V  R  N  D  W 471

GGAAACAACTATAGAAAACTTTCATGTGGTGGAAACATTAGCTGATAATGCAATCATCATTTATCAAACA 1890
  E  T  T  I  E  N  F  H  V  V  E  T  L  A  D  N  A  I  I  I  Y  Q  T    494

CACAAGAGGGTGTGGCCTGCTTCTCAGCGAGACGTATTATATCTTTCTGTCATTCGAAAGATACCAGCCT 1960
  H  K  R  V  W  P  A  S  Q  R  D  V  L  Y  L  S  V  I  R  K  I  P  A    517

TGACTGAAAATGACCCTGAAACTTGGATAGTTTGTAATTTTTCTGTGGATCATGACAGTGCTCCTCTAAA 2030
  L  T  E  N  D  P  E  T  W  I  V  C  N  F  S  V  D  H  D  S  A  P  L  N 541

CAACCGATGTGTCCGTGCCAAAATAAATGTTGCTATGATTTGTCAAACCTTGGTAAGCCCACCAGAGGGA 2100
  N  R  C  V  R  A  K  I  N  V  A  M  I  C  Q  T  L  V  S  P  P  E  G    564

AACCAGGAAATTAGCAGGGACAACATTCTATGCAAGATTACATATGTAGCTAATGTGAACCCTGGAGGAT 2170
  N  Q  E  I  S  R  D  N  I  L  C  K  I  T  Y  V  A  N  V  N  P  G  G    587

GGGCACCAGCCTCAGTGTTAAGGGCAGTGGCAAAGCGAGAGTATCCTAAATTTCTAAAACGTTTTACTTC 2240
  W  A  P  A  S  V  L  R  A  V  A  K  R  E  Y  P  K  F  L  K  R  F  T  S 611

TTACGTCCAAGAAAAAACTGCAGGAAAGCCTATTTTGTTCTAGTATTAACAGGTACTAGAAGATATGTTT 2310
  Y  V  Q  E  K  T  A  G  K  P  I  L  F                                   624

TATCTTTTTTTAACTTTATTTGACTAATATGACTGTCAATACTAAAATTTAGTTGTTGAAAGTATTTACT 2380

ATGTTTTTT                                                                2389
```

FIGURE 1b

```
GPΔIII      GLKGKRGDSGSPATWTTRGFVFTRHSQTTAI
             | | |    |
MBP         MASQKRP-SQRHGSKYLATASTMDHARHGFL

GPΔIII      PSCPEGPVPLYSGFSFLFVQGNQRAHGQDLD

MBP         PRHRDTGILDSIGRFFGGDRGAPKRGSGK--

GPΔIII      ALFVKVLRSP
            · · · · | · · | | |
MBP         VPWLKPGRSP
```

FIGURE 17

GOODPASTURE ANTIGEN BINDING PROTEIN

CROSS REFERENCE

This application claims priority to U.S. Provisional Patent Application Ser. No. 60/121,483, filed Feb. 24, 1999.

STATEMENT OF GOVERNMENT RIGHTS

This work was supported in part by Grants SAL91/0513, SAF94/1051 and SAF97/0065 from the Plan Nacional I+D of the Comisión Interministerial de Ciencia Tecnologia (CICYT, Spain), Grant 93/0343 from Fondo de Investigaciones Sanitarias (FISss, Spain) and Grants GV-3166/95, GV-C-VS-21-118-96 from la Dirección General d'Ensenyaments Universitaris i Investigació (Comunitat Valenciana, Spain); therefore the State of Spain may have rights in the invention.

FIELD OF THE INVENTION

The invention relates to the fields of protein kinases, automimmune disease, apoptosis, and cancer.

BACKGROUND OF THE INVENTION

Goodpasture (GP) disease is an autoimmune disorder described only in humans. In GP patients, autoantibodies against the non-collagenous C-terminal domain (NC1) of the type IV collagen α3 chain ("Goodpasture antigen") cause a rapidly progressive glomerulonephritis and often lung hemorrhage, the two cardinal clinical manifestations of the GP syndrome (see 1 for review. The reference numbers in this section correspond to reference list of Example 1).

The idea that common pathogenic events exist at least for some autoimmune disorders is suggested by the significant number of patients displaying more than one autoimmune disease, and also by the strong and common linkage that some of these diseases show to specific MHC haplotypes (31, 32). The experimental observation that the autoantigen is the leading moiety in autoimmunity and that a limited number of self-components are autoantigenic (31), suggest that these self-components share biological features with important consequences in self/non-self recognition by the immune system. One possibility is that triggering events, by altering different but specific self-components, would result in abnormal antigen processing. In certain individuals expressing a particular MHC specificity, the abnormal peptides could be recognized by non-tolerized T cells and trigger an immune response (1).

We have previously explored the GP antigen to identify biological features of relevance in autoimmune pathogenesis. Since the NC1 domain is a highly conserved domain among species and between the different type IV collagen α chains (α1–α6) (2), the exclusive involvement of the human α3(IV)NC1 in a natural autoimmune response suggests that this domain has structural and/or biological peculiarities of pathogenic relevance. Consistent with this, the N-terminus of the human antigen is highly divergent, and it contains a unique five-reside motif (KRGDS$^9$; SEQ ID NO: 63) that conforms to a functional phosphorylation site for type A protein kinases (3, 4). Furthermore, the human α3 gene, but not the other related human or homologous genes from other species, is alternatively spliced and generates multiple transcripts also containing the phosphorylatable N-terminal region (5, 7). Recent studies indicate that the phosphorylation of the N-terminus of the GP antigen by cAMP-dependent protein kinase is up regulated by the presence of the alternative products (see Example 3 below). Specific serine phosphorylation and pre-mRNA alternative splicing are also associated with the biology of other autoantigens including the acetylcholine receptor and myelin basic protein (MBP) (4). The latter is suspected to be the major antigen in multiple sclerosis (MS), another exclusively human autoimmune disease in which the immune system targets the white matter of the central nervous system. GP disease and MS are human disorders that display a strong association with the same HLA class II haplotype (HLA DRB1*1501)(32, 33). This, along with the recent report of death by GP disease of an MS patient carrying this HLA specificity (34), supports the existence of common pathogenic events in these human disorders.

Thus, specific serine/threonine phosphorylation may be a major biological difference between the human GP antigen, the GP antigens of other species, and the homologous domains from the other human α(IV) chains, and might be important in pathogenesis (1, 4).

Therefore, the identification and isolation of the specific serine/threonine kinase that phosphorylates the N-terminal region of the human GP antigen would be very advantageous for the diagnosis and treatment of GP syndrome, and possibly for other autoimmune disorders.

SUMMARY OF THE INVENTION

The present invention fulfills the need in the art for the identification and isolation of a serine/threonine kinase that specifically binds to and phosphorylates the unique N-terminal region of the human GP antigen. In one aspect, the present invention provides nucleic acid sequences encoding various forms of the Goodpasture antigen binding protein (GPBP), as well as recombinant expression vectors operatively linked to the GPBP-encoding sequences.

In another aspect, the present invention provides host cells that have been transfected with the recombinant expression vectors. In a further aspect, the present invention provides substantially purified GPBP and antibodies that selectively bind to GPBP. In still further aspect, the invention provides methods for detecting the presence of GPBP or nucleic acids encoding GPBP.

In a further aspect, the present invention provides methods for detecting the presence of an autoimmune condition or apoptosis, which comprises detecting an increase in the expression of GPBP in a tissue compared to a control tissue.

In another aspect, the present invention provides methods and pharmaceutical compositions for treating an autoimmune disorder, apoptosis, or a tumor, comprising modifying the expression or activity of GPBP in a patient in need thereof.

BRIEF DESCRIPTION OF THE FIGURES

FIGS. 1a–b. Nucleotide (SEQ ID NO: 1) and derived amino acid (SEQ ID NO: 2) sequences of n4'. The denoted structural features are from 5' to 3' end: the cDNA present in the original clone (HeLa1) (dotted box), which contains the PH homology domain (in black) and the Ser-Xaa-Yaa repeat (in gray); the heptad repeat of the predictable coiled-coil structure (open box) containing the bipartite nuclear localization signal (in gray); and a serine-rich domain (filled gray box). The asterisks denote the positions of in frame stop codons.

FIG. 17. Sequence alignment of GPΔIII and MBP. The phosphorylation sites for PKA (boxed) and the structural similarity for the sites at Ser 8 and 9 of MBP and GPΔIII respectively are shown (underlined). The identity (vertical bars) and chemical homology (dots) of the corresponding exon II (bent arrow) of both molecular species are indicated. The complete sequence of GPΔIII (SEQ ID NO: 61) from the collagenase cleavage site (72-residues) is aligned with the 69-N terminal residues of MBP (SEQ ID NO: 62) comprising the exon I and ten residues of the exon II.

DETAILED DESCRIPTION OF THE INVENTION

Figure 2:
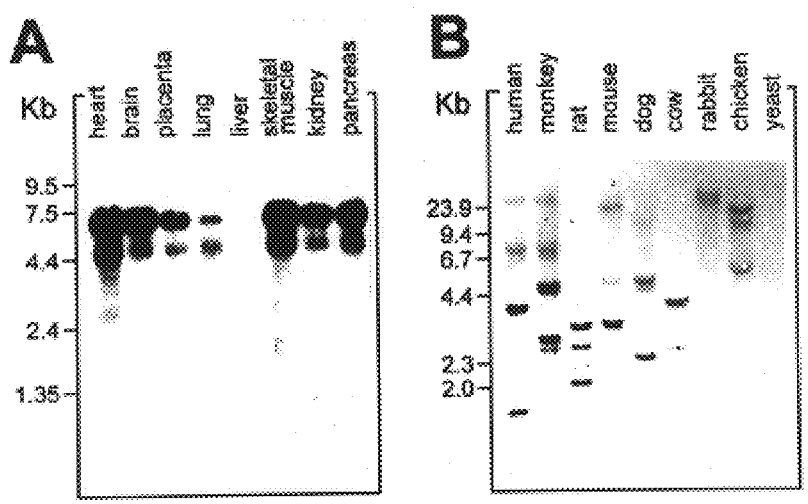
FIG. 2. Distribution of GPBP in human tissues (Northern blot) and in eukaryotic species (Southern blot). A random primed $^{32}$P-labeled HeLa1 cDNA probe was used to identify homologous messages in a Northern blot of poly(A+)RNA from the indicated human tissues (panel A) or in a Southern blot of genomic DNA from the indicated eukaryotic species (panel B). Northern hybridization was performed under highly stringent conditions to detect perfect matching messages and at low stringency in the Southern to allow the detection of messages with mismatches. No appreciable differences in the quality and amount of each individual poly A+ RNA was observed by denaturing gel electrophoresis or when probing a representative blot from the same lot with human β-actin cDNA. The numbers denote the position and the sizes in kb of the RNA or DNA markers used.

All references cited are herein incorporated by reference in their entirety.

The abbreviations used herein are: bp, base pair; DTT, dithiothreitol; DMEM, Dulbecco's modified Eagle's medium; EDTA, ethylenediamine tetraacetic acid; EGTA, ethylene glycol-bis(β-aminoethyl ether) N,N,N',N'-tetraacetic acid; GP, Goodpasture; rGPΔIII, rGPΔIII/IV/V and rGPΔV, recombinant material representing the alternative forms of the Goodpasture antigen resulting from splicing out exon III, exon III, IV and V or exon V, respectively; GPBP and rGPBP, native and recombinant Goodpasture antigen binding protein; GPBPΔ26 and rGPBPΔ26, native and recombinant alternative form of the GPBP; GST, glutathione S-transferase; HLA, human lymphocyte antigens; HPLC, high performance liquid chromatography; Kb, thousand base pairs; kDa, thousand daltons; MBP, rMBP, native and recombinant 21 kDa myelin basic protein; MBPΔII and rMBPΔII, native and recombinant 18.5 kDa myelin basic protein that results from splicing out exon II; MBPΔV and MBPΔII/V, myelin basic protein alternative forms resulting from splicing out exon V and exons II and V, respectively; MHC, major histocompatibility complex; NC1, non-collagenous domain; PH, pleckstrin homology; PKA, cAMP-dependent protein kinase; PMSF, phenylmethylsulfonyl fluoride; SDS-PAGE, sodium dodecylsulfate polyacrylamide gel electrophoresis; TBS, tris buffered saline.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

As used herein, the term "GPBP" refers to Goodpasture binding protein, and includes both monomers and oligomers thereof. Human (SEQ ID NO:2), mouse (SEQ ID NO:4), and bovine GPBP sequences (SEQ ID NO:6) are provided herein.

As used herein, the term "GPBPΔ26" refers to Goodpasture binding protein deleted for the 26 amino acid sequence shown in SEQ ID NO:14, and includes both monomers and oligomers thereof. Human (SEQ ID NO:8), mouse (SEQ ID NO:10), and bovine GPBP sequences (SEQ ID NO:12) are provided herein.

As used herein the term "GPBPpep1" refers to the 26 amino acid peptide shown in SEQ ID NO:14, and includes both monomers and oligomers thereof.

As used herein, the term "GP antigen" refers to the α3 NC1 domain of type IV collagen.

As used herein, "MBP" refers to myelin basic protein.

In one aspect, the present invention provides isolated nucleic acids that encode GPBP, GPBPΔ26, and GPBPpep1, and mutants or fragments thereof. In one embodiment, the isolated nucleic acids comprise sequences substantially similar to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO: 17, SEQ ID NO: 19, SEQ ID NO:21, SEQ ID NO:23, or SEQ ID NO:25, or fragments thereof.

In another aspect, the present invention provides isolated nucleic acids that encode alternative products of the GP antigen or MBP. In one embodiment, the isolated nucleic acids comprise sequences that encode peptides substantially similar to SEQ ID NO:43 and SEQ ID NO:44.

The phrase "substantially similar" is used herein in reference to the nucleotide sequence of DNA or RNA, or the amino acid sequence of protein, having one or more conservative or non-conservative variations from the disclosed sequences, including but not limited to deletions, additions, or substitutions, wherein the resulting nucleic acid and/or amino acid sequence is functionally equivalent to the sequences disclosed herein. Functionally equivalent sequences will function in substantially the same manner to produce substantially the same protein disclosed herein. For example, functionally equivalent DNAs encode proteins that are the same as those disclosed herein or that have one or more conservative amino acid variations, such as substitution of a non-polar residue for another non-polar residue or a charged residue for a similarly charged residue. These changes include those recognized by those of skill in the art as substitutions that do not substantially alter the tertiary structure of the protein.

In practice, the term substantially similar means that DNA encoding two proteins hybridize to one another under conditions of moderate to high stringency, and encode proteins that have either the same sequence of amino acids, or have changes in sequence that do not alter their structure or function. As used herein, substantially similar sequences of nucleotides or amino acids share at least about 70% identity, more preferably at least about 80% identity, and most preferably at least about 90% identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

Stringency of hybridization is used herein to refer to conditions under which nucleic acid hybrids are stable. As known to those of skill in the art, the stability of hybrids is reflected in the melting temperature ($T_M$) of the hybrids. $T_M$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein, moderate stringency refers to conditions that permit hybridization of those nucleic acid sequences that form stable hybrids in 0.1% SSPE at 37° C. or 55° C., while high stringency refers to conditions that permit hybridization of those nucleic acid sequences that form stable hybrids in 0.1%SSPE at 65° C. It is understood that these conditions may be duplicated using a variety of buffers and temperatures and that they are not necessarily precise. Denhardt's solution and SSPE (see, e.g., Sambrook, Fritsch, and Maniatis, in: Molecular Cloning, A Laboratory Manual, Cold Spring Harbor Laboratory Press, 1989) are well known to those of skill in the art, as are other suitable hybridization buffers.

The isolated nucleic acid sequence may comprise an RNA, a cDNA, or a genomic clone with one or more introns. The isolated sequence may further comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals.

In another aspect, the present invention provides recombinant expression vectors comprising nucleic acid sequences that express GPBP, GPBPΔ26, or GPBPpep1, and mutants or fragments thereof. In one embodiment, the vectors comprise nucleic acid sequences that are substantially similar to the sequences shown in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, or SEQ ID NO:25, or fragments thereof.

In another aspect, the present invention provides recombinant expression vectors comprising nucleic acid sequences that express peptides that are substantially similar to the amino acid sequence shown in SEQ ID NO:43, SEQ ID NO:44, or peptide fragments thereof.

"Recombinant expression vector" includes vectors that operatively link a nucleic acid coding region or gene to any promoter capable of effecting expression of the gene product. The promoter sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols,* pp. 109–128, ed. E. J. Murray, The Humana Press Inc., Clifton, N.J.), and the Ambion 1998 Catalog (Ambion, Austin, Tex.).

The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a further aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique,* $2^{nd}$ Ed. (R. I. Freshney. 1987. Liss, Inc. New York, N.Y.), In a still further aspect, the present invention provides substantially purified GPBP, GPBPΔ26, and GPBPpep1, and mutants or fragments thereof. In one embodiment, the amino acid sequence of the substantially purified protein is substantially similar to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or peptide fragments thereof.

In another aspect, the present invention provides substantially purified alternative products of the GP antigen and MBP. In one embodiment, the amino acid sequence of the substantially purified polypeptide is substantially similar to SEQ ID NO:43, SEQ ID NO:44, or peptide fragments thereof.

As used herein, the term "substantially purified" means that the protein has been separated from its in vivo cellular environments. Thus, the protein can either be purified from natural sources, or recombinant protein can be purified from the transfected host cells disclosed above. In a preferred embodiment, the proteins are produced by the transfected cells disclosed above, and purified using standard techniques. (See for example, *Molecular Cloning: A Laboratory Manual* (Sambrook, et al., 1989, Cold Spring Harbor Laboratory Press.)) The protein can thus be purified from prokaryotic or eukaryotic sources. In various further preferred embodiments, the protein is purified from bacterial, yeast, or mammalian cells.

The protein may comprise additional sequences useful for promoting purification of the protein, such as epitope tags and transport signals. Examples of such epitope tags include, but are not limited to FLAG (Sigma Chemical, St. Louis, Mo.), myc (9E10) (Invitrogen, Carlsbad, Calif.), 6-His (Invitrogen; Novagen, Madison, Wis.), and HA (Boehringer Manheim Biochemicals). Examples of such transport signals include, but are not limited to, export signals, secretory signals, nuclear localization signals, and plasma membrane localization signals.

In another aspect, the present invention provides antibodies that selectively bind to GPBP, GPBPΔ26, or GPBPpep1. In one aspect, the antibodies selectively bind to a protein comprising a sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, or peptide fragments thereof. Such antibodies can be produced by immunization of a host animal with either the complete GPBP, or with antigenic peptides thereof. The antibodies can be either polyclonal or monoclonal.

In another aspect, the present invention provides antibodies that selectively bind to a polypeptide comprising an amino acid sequence substantially similar to a sequence selected from the group consisting of SEQ ID NO:43, SEQ ID NO:44, SEQ ID NO: 46, SEQ ID NO: 48, SEQ ID NO:50, SEQ ID NO:54, or antigenic fragments thereof. The antibodies can be either polyclonal or monoclonal.

Antibodies can be made by well-known methods, such as described in Harlow and Lane, Antibodies; A Laboratory Manual, Cold Spring Harbor Laboratory, Cold Spring Harbor, N.Y., (1988). In one example, preimmune serum is collected prior to the first immunization. Substantially purified proteins of the invention, or antigenic fragments thereof, together with an appropriate adjuvant, is injected into an animal in an amount and at intervals sufficient to elicit an immune response. Animals are bled at regular intervals, preferably weekly, to determine antibody titer. The animals may or may not receive booster injections following the initial immunization. At about 7 days after each booster immunization, or about weekly after a single immunization, the animals are bled, the serum collected, and aliquots are stored at about −20° C. Polyclonal antibodies against the proteins and peptides of the invention can then be purified directly by passing serum collected from the animal through a column to which non-antigen-related proteins prepared from the same expression system without GPBP-related proteins bound.

Monoclonal antibodies can be produced by obtaining spleen cells from the animal. (See Kohler and Milstein, Nature 256, 495–497 (1975)). In one example, monoclonal antibodies (mAb) of interest are prepared by immunizing inbred mice with the proteins or peptides of the invention, or an antigenic fragment thereof. The mice are immunized by the IP or SC route in an amount and at intervals sufficient to elicit an immune response. The mice receive an initial immunization on day 0 and are rested for about 3 to about 30 weeks. Immunized mice are given one or more booster immunizations of by the intravenous (IV) route.

Lymphocytes, from antibody positive mice are obtained by removing spleens from immunized mice by standard procedures known in the art. Hybridoma cells are produced by mixing the splenic lymphocytes with an appropriate fusion partner under conditions which will allow the formation of stable hybridomas. The antibody producing cells and fusion partner cells are fused in polyethylene glycol at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells and are screened for antibody production by an immunoassay such as solid phase immunoradioassay. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

To generate such an antibody response, the proteins of the present invention are typically formulated with a pharmaceutically acceptable carrier for parenteral administration. Such acceptable adjuvants include, but are not limited to, Freund's complete, Freund's incomplete, alum-precipitate, water in oil emulsion containing Corynebacterium parvum and tRNA. The formulation of such compositions, including the concentration of the polypeptide and the selection of the vehicle and other components, is within the skill of the art.

The term antibody as used herein is intended to include antibody fragments thereof which are selectively reactive with the proteins and peptides of the invention, or fragments thereof. Antibodies can be fragmented using conventional techniques, and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

In a further aspect, the invention provides methods for detecting the presence of the proteins or peptides of the invention in a protein sample, comprising providing a protein sample to be screened, contacting the protein sample to be screened with an antibody against the proteins or peptides of the invention, and detecting the formation of antibody-antigen complexes. The antibody can be either polyclonal or monoclonal as described above, although monoclonal antibodies are preferred. As used herein, the term "protein sample" refers to any sample that may contain the proteins or peptides of the invention, and fragments thereof, including but not limited to tissues and portions thereof, tissue sections, intact cells, cell extracts, purified or partially purified protein samples, bodily fluids, nucleic acid expression libraries. Accordingly, this aspect of the present invention may be used to test for the presence of GPBP, GPBPΔ26, GPBPpep1, or alternative products of the GP antigen in these various protein samples by standard techniques including, but not limited to, immunolocalization, immunofluorescence analysis, Western blot analysis, ELISAs, and nucleic acid expression library screening, (See for example, Sambrook et al, 1989.) In one embodiment, the techniques may determine only the presence or absence of the protein or peptide of interest. Alternatively, the techniques may be quantitative, and provide information about the relative amount of the protein or peptide of interest in the sample. For quantitative purposes, ELISAs are preferred.

Detection of immunocomplex formation between the proteins or peptides of the invention, or fragments thereof, and their antibodies or fragments thereof, can be accomplished by standard detection techniques. For example, detection of immunocomplexes can be accomplished by using labeled antibodies or secondary antibodies. Such methods, including the choice of label are known to those ordinarily skilled in the art. (Harlow and Lane, Supra). Alternatively, the polyclonal or monoclonal antibodies can be coupled to a detectable substance. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase. Examples of suitable prosthetic-group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of suitable radioactive material include $^{125}$I, $^{131}$I, $^{35}$S or $^3$H.

Such methods of detection are useful for a variety of purposes, including but not limited to detecting an autoimmune condition, identifying cells targeted for or undergoing apoptosis, immunolocalization of the proteins of interest in a tissue sample, Western blot analysis, and screening of expression libraries to find related proteins.

In yet another aspect, the invention provides methods for detecting the presence in a sample of nucleic acid sequences encoding the GPBP, GPBPΔ26, GPBPpep1, or alternative products of the GP antigen comprising providing a nucleic acid sample to be screened, contacting the sample with a nucleic acid probe derived from the isolated nucleic acid sequences of the invention, or fragments thereof, and detecting complex formation.

As used herein, the term "sample" refers to any sample that may contain GPBP-related nucleic acid, including but not limited to tissues and portions thereof, tissue sections, intact cells, cell extracts, purified or partially purified nucleic acid samples, DNA libraries, and bodily fluids. Accordingly, this aspect of the present invention may be used to test for the presence of GPBP mRNA or DNA in these various samples by standard techniques including, but not limited to, in situ hybridization, Northern blotting, Southern blotting, DNA library screening, polymerase chain reaction (PCR) or reverse transcription-PCR (RT-PCR). (See for example, Sambrook et al, 1989.) In one embodiment, the techniques may determine only the presence or absence of the nucleic acid of interest. Alternatively, the techniques may be quantitative, and provide information about the relative amount of the nucleic acid of interest in the sample. For quantitative purposes, quantitative PCR and RT-PCR are preferred. Thus, in one example, RNA is isolated from a sample, and contacted with an oligonucleotide derived from the nucleic acid sequence of interest, together with reverse transcriptase under suitable buffer and temperature conditions to produce cDNAs from the GPBP-related RNA. The cDNA is then subjected to PCR using primer pairs derived from the nucleic acid sequence of interest. In a preferred embodiment, the primers are designed to detect the presence of the RNA expression product of SEQ ID NO:5, and the amount of GPBP gene expression in the sample is compared to the level in a control sample.

For detecting the nucleic acid sequence of interest, standard labeling techniques can be used to label the probe, the nucleic acid of interest, or the complex between the probe and the nucleic acid of interest, including, but not limited to radio-, enzyme-, chemiluminescent-, or avidin or biotin-labeling techniques, all of which are well known in the art. (See, for example, *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.); *PCR Protocols: A Guide to Methods and Applications* (Innis, et al. 1990. Academic Press, San Diego, Calif.)).

Such methods of nucleic acid detection are useful for a variety of purposes, including but not limited to diagnosing an autoimmune condition, identifying cells targeted for or undergoing apoptosis, in situ hybridization, Northern and Southern blot analysis, and DNA library screening.

As demonstrated in the following examples, GPBP shows preferential expression in tissue structures that are commonly targeted in naturally-occurring autoimmune responses, and is highly expressed in several autoimmune conditions, including but not limited to Goodpasture Syndrome (GP), systemic lupus erythematosus (SLE), and lichen planus. Furthermore, following a similar experimental approach to that described below, recombinant proteins representing autoantigens in GP disease (α3 Type IV collagen), SLE (P1 ribosomal phosphoprotein and Sm-D1 small nuclear ribonucleoproteins) and dermatomyositis (hystididyl-tRNA synthetase) were shown to be in vitro substrates of GPBP.

Thus, in a preferred embodiment, detection of GPBP expression is used to detect an autoimmune condition. A sample that is being tested is compared to a control sample for the expression of GPBP, wherein an increased level of GPBP expression indicates the presence of an autoimmune condition. In this embodiment, it is preferable to use antibodies that selectively bind to GPBPpep1, which is present in GPBP but not in GPBPΔ26.

Furthermore, as shown in the accompanying examples, GPBP is down-regulated in tumor cell lines, and the data suggest that GPBP/GPBPΔ26 are likely to be involved in cell signaling pathways that induce apoptosis, which may be up-regulated during autoimmune pathogenesis and down-regulated during cell transformation to prevent autoimmune attack to transformed cells during tumor growth. Thus, the detection methods disclosed herein can be used to detect cells that are targeted for, or are undergoing apoptosis.

In another aspect, the present invention provides a method for treating an autoimmune disorder, a tumor, or for preventing cell apoptosis comprising modification of the expression or activity of GPBP, GPBPΔ26, or a protein comprising a polypeptide substantially similarly to GPBPpep1 in a patient in need thereof Modifying the expression or activity of GPBP, GPBPΔ26, or a protein comprising a polypeptide substantially similarly to GPBPpep1 can be accomplished by using specific inducers or inhibitors of GPBP expression or activity, GPBP antibodies, gene or protein therapy using GP or myelin basic protein alternative products, cell therapy using host cells expressing GP or myelin basic protein alternative products, antisense therapy, or other techniques known in the art. In a preferred embodiment, the method further comprises administering a substantially purified alternative product of the GP antigen or MBP to modify the expression or activity of GPBP, GPBPΔ26, or a protein comprising a polypeptide substantially similarly to GPBPpep1. As used herein, "modification of expression or activity" refers to modifying expression or activity of either the RNA or protein product.

In a further aspect, the present invention provides pharmaceutical compositions, comprising an amount effective of substantially purified alternative products of the GP antigen or MBP to modify the expression or activity of GPBP RNA or protein, and a pharmaceutically acceptable carrier.

For administration, the active agent is ordinarily combined with one or more adjuvants appropriate for the indicated route of administration. The compounds may be mixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The present invention may be better understood with reference to the accompanying examples that are intended for purposes of illustration only and should not be construed to limit the scope of the invention, as defined by the claims appended hereto.

EXAMPLE 1

Characterization of GPBP

Here we report the cloning and characterization of a novel type of serine/threonine kinase that specifically binds to and phosphorylates the unique N-terminal region of the human GP antigen.

MATERIALS AND METHODS

Synthetic polymers
Peptides
GPpep1, KGKRGDSGSPATWTTRGFVFT (SEQ ID NO:26), representing residues 3–23 of the human GP antigen and GPpep1Ala$^9$, KGKRGDAGSPATWTTRGFVFT (SEQ ID NO:27), a mutant Ser$^9$ to Ala$^9$ thereof, were synthesized by MedProbe and CHIRON. FLAG peptide, was from Sigma.
Oligonucleotides
The following as well as several other GPBP-specific oligonucleotides were synthesized by Genosys and GIBCO BRL:

> ON-GPBP..54m: TCGAATTCACCATGGCCCCACTAGC-
> CGACTACAAGGACGACGATG ACAAG (SEQ ID NO: 28).
>
> ON-GPBP..55c: CCGAGCCCGACGAGTTCCAGCTCTGAT-
> TATCCGACATCTTGTCATCG TCG (SEQ ID NO:29).
>
> ON-HNC-B-N-14m: CGGGATCCGCTAGCTAAGCCAG-
> GCAAGGATGG (SEQ ID NO:30).
>
> ON-HNC-B-N-16c: CGGGATCCATGCATAAATAGCAGTTCT-
> GCTGT (SEQ ID NO:31).

Isolation and Characterization of cDNA Clones Encoding Human GPBP

Several human λ-gt11 cDNA expression libraries (eye, fetal and adult lung, kidney and HeLa S3, from CLONTECH) were probed for cDNAs encoding proteins interacting with GPpep1. Nitrocellulose filters (Millipore) prepared following standard immunoscreening procedures were blocked and incubated with 1–10 nmoles per ml of GPpep1 at 37° C. Specifically bound GPpep1 was detected using M3/1A monoclonal antibodies (7). A single clone was identified in the HeLa-derived library (HeLa1). Specificity of fusion protein binding was confirmed by similar binding to recombinant eukaryotic human GP antigen. The EcoRI cDNA insert of HeLa1 (0.5-kb) was used to further screen the same library and to isolate overlapping cDNAs. The largest cDNA (2.4-kb) containing the entire cDNA of HeLa1 (n4') was fully sequenced.

Northern and Southern Blots

Pre-made Northern and Southern blots (CLONTECH) were probed with HeLa1 cDNA following manufacturer instructions.

Plasmid Construction, Expression and Purification of Recombinant Proteins

GPBP-derived Material

The original λ-gt11 HeLa1 clone was expressed as a lysogen in *E. Coli* Y1089 (8). The corresponding β-galactosidase-derived fusion protein containing the N-terminal 150 residues of GPBP was purified from the cell lysate using an APTG-agarose column (Boehringer). The EcoRI 2.4-kb fragment of n4' was subcloned in Bluescribe M13+ vector (Stratagene) (BS-n4'), amplified and used for subsequent cloning. A DNA fragment containing (from 5' to 3'), an EcoRI restriction site, a standard Kozak consensus for translation initiation, a region coding for a tag peptide sequence (FLAG, DYKDDDDK (SEQ ID NO:32)), and the sequence coding for the first eleven residues of GPBP including the predicted $Met_i$ and a Ban II restriction site, was obtained by hybridizing ON-GPBP-54m and ON-GPBP-55c, and extending with modified $T_7$ DNA polymerase (Amersham). The resulting DNA product was digested with EcoRI and BanII, and ligated with the BanII/EcoRI cDNA fragment of BS-n4' in the EcoRI site of pHIL-D2 (Invitrogen) to produce pHIL-FLAG-n4'. This plasmid was used to obtain $Mut^s$ transformants of the GS115 strain of *Pichia pastoris* and to express FLAG-tagged recombinant GPBP (rGPBP) either by conventional liquid culture or by fermentation procedures (Pichia Expression Kit, Invitrogen). The cell lysates were loaded onto an anti-FLAG M2 column (Sigma), the unbound material washed out with Tris buffered saline (TBS, 50 mM Tris-HCl, pH 7.4, 150 mM NaCl) or salt-supplemented TBS (up to 2M NaCl), and the recombinant material eluted with FLAG peptide. For expression in cultured human kidney-derived 293 cells (ATCC 1573-CRL), the 2.4- or 2.0-kb EcoRI cDNA insert of either BS-n4' or pHIL-FLAG-n4' was subcloned in pcDNA3 (Invitrogen) to produce pc-n4' and pc-FLAG-n4'respectively. When used for transient expression, 18 hours after transfection the cells were lysed with 3.5–4 $\mu$l/cm² of chilled lysis buffer (1% Nonidet P-40 or Triton-X100, 5 mM EDTA and 1 mM PMSF in TBS) with or without 0.1% SDS, depending on whether the lysate was to be used for SDS-PAGE or FLAG-purification, respectively. For FLAG purification, the lysate of four to six 175 cm² culture dishes was diluted up to 50 ml with lysis buffer and purified as above. For stable expression, the cells were similarly transfected with pc-n4' and selected for three weeks with 800 $\mu$g/ml of G418. For bacterial recombinant expression, the 2.0-kb EcoRI cDNA fragment of pHIL-FLAG-n4' was cloned in-frame downstream of the glutathione S-transferase (GST)-encoding cDNA of pGEX-5x-1 (Pharmacia). The resulting construct was used to express GST-GPBP fusion protein in DH5α cells (9).

GP Antigen-derived Material

Human recombinant GP antigen (rGP) was produced in 293 cells using the pRc/CMV-BM40 expression vector containing the α3-specific cDNA between ON-HNC-B-N-14m and ON-HNC-B-N-16c. The expression vector is a pRc/CMV (Invitrogen)-derived vector provided by Billy G. Hudson (Kansas University Medical Center) that contains cDNA encoding an initiation Met, a BM40 signal peptide followed by a tag peptide sequence (FLAG), and a polylinker cloning site. To obtain α3-specific cDNA, a polymerase chain reaction was performed using the oligonucleotides above and a plasmid containing the previously reported α3(IV) cDNA sequence (3) as template (clone C2). For stable expression of rGP, 293 cells were transfected with the resulting construct (fα3VLC) and selected with 400 $\mu$g/ml of G418. The harvested rGP was purified using an anti-FLAG M2 column.

All the constructs were verified by restriction mapping and nucleotide sequencing.

Cell Culture and DNA Transfection

Human 293 cells were grown in Dulbecco's modified Eagle's medium (DMEM) supplemented with 10% fetal calf serum. Transfections were performed using the calcium phosphate precipitation method of the Profection Mammalian Transfection Systems (Promega). Stably transfected cells were selected by their resistance to G418. Foci of surviving cells were isolated, cloned and amplified.

Antibody Production

Polyclonal Antibodies Against the N-terminal Region of GPBP

Cells expressing HeLa1 λ-gt11 as a lysogen were lysed by sonication in the presence of Laemmli sample buffer and subjected to electrophoresis in a 7.5% acrylamide preparative gel. The gel was stained with Coomassie blue and the band containing the fusion protein of interest excised and used for rabbit immunization (10). The anti-serum was tested for reactivity using APTG-affinity purified antigen. To obtain affinity-purified antibodies, the anti-serum was diluted 1:5 with TBS and loaded onto a Sepharose 4B column containing covalently bound affinity purified antigen. The bound material was eluted and, unless otherwise indicated, used in the immunochemical studies.

Monoclonal Antibodies Against GPBP

Monoclonal antibodies were produced essentially as previously reported (7) using GST-GPBP. The supernatants of individual clones were analyzed for antibodies against rGPBP.

In vitro Phosphorylation Assays

About 200 ng of rGPBP were incubated overnight at 30° C. in 25 mM β-glycerolphosphate (pH 7.0), 0.5 mM EDTA, 0.5 mM EGTA, 8 mM $MgCl_2$, 5 mM $MnCl_2$, 1 mM DTT and 0.132 $\mu$M γ-$^{32}$P-ATP, in the presence or absence of 0.5–1 $\mu$g of protein substrates or 10 nmoles of synthetic peptides, in a total volume of 50 $\mu$l.

In vivo Phosphorylation Assays

Individual wells of a 24-well dish were seeded with normal or with stably pc-n4' transfected 293 cells. When the cells were grown to the desired density, a number of wells of the normal 293 cells were transfected with pc-FLAG-n4'. After 12 hours, the culture medium was removed, 20 $\mu$Ci/well of $H_3^{32}PO4$ in 100 $\mu$l of phosphate-free DMEM added, and incubation continued for 4 hours. The cells were lysed with 300 $\mu$l/well of TBS containing 1% Triton X-100, 2 mM EDTA, 1 mM PMSF, 50 mM NaF and 0.2 mM vanadate, and extracted with specific antibodies and Protein A-Sepharose. When anti-GPBP serum was used, the lysate was pre-cleared using pre-immune serum and Protein A-Sepharose.

In vitro Dephosphorylation of rGPBP

About 1 $\mu$g of RGPBP was dephosphorylated in 100 $\mu$l of 10 mM Tris-acetate (pH 7.5), 10 mM magnesium acetate and 50 mM potassium acetate with 0.85 U of calf intestine alkaline phosphatase (Pharmacia) for 30 min at 30° C.

Renaturation Assays

In-blot renaturation assays were performed using 1–5 μg of rGPBP as previously described (11).

Nucleotide Sequence Analysis cDNA sequence analyses were performed by the dideoxy chain termination method using [α]$^{35}$S-dATP, modified T$_7$ DNA polymerase (Amersham) and universal or GPBP-specific primers (8–10).

$^{32}$P..Phosphoamino Acid Analysis

Immunopurified rGPBP or HPLC gel-filtration fractions thereof containing the material of interest were phosphorylated, hydrolyzed and analyzed in one dimensional (4) or two dimensional thin layer chromatography (12). When performing two dimensional analysis, the buffer for the first dimension was formic acid:acetic acid:water (1:3.1:35.9) (pH 1.9) and the buffer for the second dimension was acetic acid:pyridine:water (2:0.2:37.8) (pH 3.5). Amino acids were revealed with ninhydrin, and $^{32}$P-phosphoamino acids by autoradiography.

Physical Methods and Immunochemical Techniques

SDS-PAGE and Western-blotting were performed as in (4). Immunohistochemistry studies were done on human multi-tissue control slides (Biomeda, Biogenex) using the ABC peroxidase method (13).

Computer Analysis

Homology searches were carried out against the GenBank and SwissProt databases with the BLAST 2.0 (14) at the NCBI server, and against the TIGR Human Gene Index database for expressed sequence tags, using the Institute for Genomic Research server. The search for functional patterns and profiles was performed against the PROSITE database using the ProfileScan program at the Swiss Institute of Bioinformatics (15). Prediction of coiled-coil structures was done at the Swiss Institute for Experimental Cancer Research using the program Coils (16) with both 21 and 28 residue windows.

RESULTS

Molecular Cloning of GPBP

To search for proteins specifically interacting with the divergent N-terminal region of the human GP antigen, a 21-residue peptide (GPpep1; SEQ ID NO:26)), encompassing this region and flanking sequences, and specific monoclonal antibodies against it were combined to screen several human cDNA expression libraries. More than 5×10$^6$ phages were screened to identify a single HeLa-derived recombinant encoding a fusion protein specifically interacting with GPpep1 without disturbing antibody binding.

Using the cDNA insert of the original clone (HeLa1), we isolated a 2.4-kb cDNA (n4') that contains 408-bp of 5'-untranslated sequence, an open reading frame (ORF) of 1872-bp encoding 624 residues, and 109-bp of 3'-untranslated sequence (FIG. 1) (SEQ ID NO:1–2). Other structural features are of interest. First, the predicted polypeptide (hereinafter referred to as GPBP) has a large number of phosphorylatable (17.9%) and acidic (16%) residues unequally distributed along the sequence. Serine, which is the most abundant residue (9.3%), shows preference for two short regions of the protein, where it comprises nearly 40% of the amino acids, compared to an average of less than 7% throughout the rest of the polypeptide chain. It is also noteworthy that the more N-terminal, serine-rich region consists mainly of a Ser-Xaa-Yaa repeat. Acidic residues are preferentially located at the N-terminal three-quarters of the polypeptide, with nearly 18% of the residues being acidic. These residues represent only 9% in the most C-terminal quarter of the polypeptide, resulting in a polypeptide chain with two electrically opposite domains. At the N-terminus, the polypeptide contains a pleckstrin homology (PH) domain, which has been implicated in the recruitment of many signaling proteins to the cell membrane where they exert their biological activities (17). Finally, a bipartite nuclear targeting sequence (18) exists as an integral part of a heptad repeat region that meets all the structural requirements to form a coiled-coil (16).

Protein data bank searches revealed homologies almost exclusively within the approximately 100 residues at the N-terminal region harboring the PH domain. The PH domain of the oxysterol-binding protein is the most similar, with an overall identity of 33.5% and a similarity of 65.2% with GPBP. In addition, the *Caenorhabditis elegans* cosmid F25H2 (accession number Q93569) contains a hypothetical ORF that displays an overall identity of 26.5% and a similarity of 61% throughout the entire protein sequence, indicating that similar proteins are present in lower invertebrates. Several human expressed sequence tags (accession numbers AA287878, AA287561, AA307431, AA331618, AA040134, AA158618, AA040087, AA122226, AA158617, AA121104, AA412432, AA412433, AA282679 and N27578) possess a high degree of nucleotide identity (above 98%) with the corresponding stretches of the GPBP cDNA, suggesting that they represent human GPBP. Interestingly, the AA287878 EST shows a gap of 67 nucleotides within the sequence corresponding to the GPBP 5'-untranslated region, suggesting that the GPBP pre-mRNA is alternatively spliced in human tissues (not shown).

The distribution and expression of the GPBP gene in human tissues was first assessed by Northern blot analysis (FIG. 2, panel A). The gene is expressed as two major mRNAs species between 4.4-kb and 7.5-kb in length and other minor species of shorter lengths. The structural relationship between these multiple mRNA species is not known and their relative expression varies between tissues. The highest expression level is seen in striated muscle (skeletal and heart), while lung and liver show the lowest expression levels.

Southern blot studies analysis of genomic DNA from different species indicated that homologous genes exist throughout phylogeny (FIG. 2, panel B). Consistent with the human origin of the probe, the hybridization intensities decreased in a progressive fashion as the origin of the genomic DNA moves away from humans in evolution.

Experimental Determination of the Translation Start Site

Figure 3:
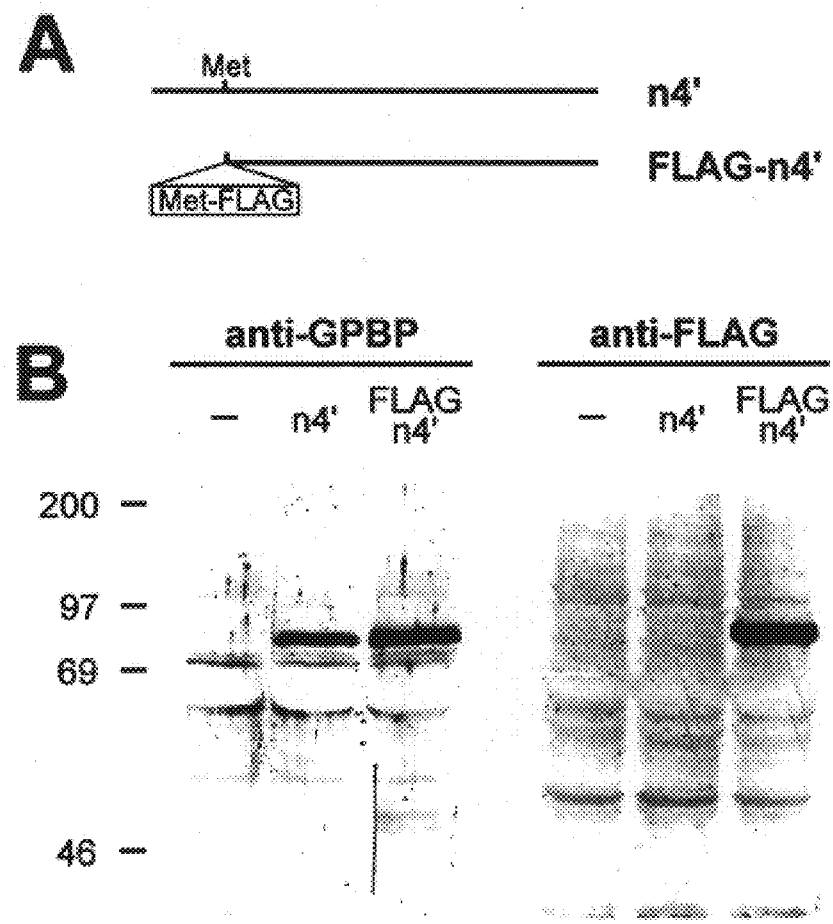
FIG. 3. Experimental determination of the translation start site. In (A), the two cDNAs present in pc-n4' and pc-FLAG-n4' plasmids used for transient expression are represented as black lines. The relative position of the corresponding predicted (n4') or engineered (FLAG-n4') translation start site is indicated (Met). In (B), the extracts from control (−), pc-n4'(n4') or pc-FLAG-n4' (FLAG-n4') transfected 293 cells were subjected to SDS-PAGE under reducing conditions in 10% gels. The separated proteins were transferred to a PVDF membrane (Millipore) and blotted with the indicated antibodies. The numbers and bars indicate the molecular mass in kDa and the relative positions of the molecular weight markers, respectively.

To experimentally confirm the predicted ORF, eukaryotic expression vectors containing either the 2.4-kb of cDNA of n4', or only the predicted ORF tagged with a FLAG sequence (FIG. 3A), were used for transient expression assays in 293 cells. The corresponding extracts were analyzed by immunoblot using GPBP- or FLAG-specific antibodies. The GPBP-specific antibodies bind to a similar major polypeptide in both transfected cells, but only the polypeptide produced by the engineered construct expressed the FLAG sequence (FIG. 3B). This located the translation start site of the n4' cDNA at the predicted Met and confirmed the proposed primary structure. Furthermore, the recombinant polypeptides displayed a molecular mass higher than expected (80 versus 71 kDa) suggesting that GPBP undergoes post-translational modifications.

Expression and Characterization of Yeast rGPBP

Figure 4:
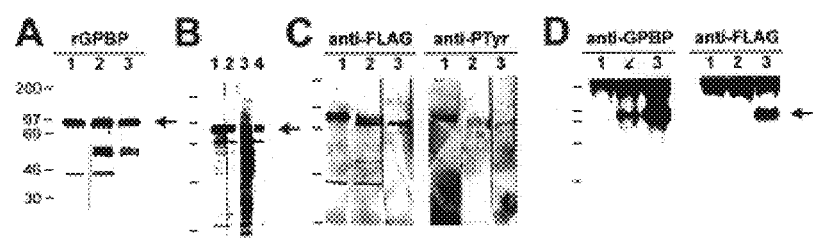
FIG. 4. Characterization of rGPBP from yeast and 293 cells. In (A), 1 μg (lane 1) or 100 ng (lanes 2 and 3) of yeast rGPBP were analyzed by reducing SDS-PAGE in a 10% gel. The separated proteins were stained with Coomassie blue (lane 1) or transferred and blotted with anti-FLAG antibodies (lane 2) or Mab14, a monoclonal antibody against GPBP (lane 3). In (B), the cell extracts from GPBP-expressing yeast were analyzed as in A and blotted with anti-FLAG (lane 1), anti-PSer (lane 2), anti-PThr (lane 3) or anti-PTyr (lane 4) monoclonal antibodies respectively. In (C), 200 ng of either yeast rGPBP (lane 1), dephosphorylated yeast rGPBP (lane 2) or 293 cells-derived rGPBP (lane 3) were analyzed as in B with the indicated antibodies. In (D), similar amounts of $H_3{}^{32}PO_4$-labeled non-transfected (lanes 1), stable pc-n4' transfected (lanes 2) or transient pc-FLAG-n4' expressing (lanes 3) 293 cells were lysed, precipitated with the indicated antibodies and analyzed by SDS-PAGE and autoradiography. The molecular weight markers are represented with numbers and bars as in FIG. 3. The arrows indicate the position of the rGPBP.

Yeast expression and FLAG-based affinity-purification were combined to produce rGPBP (FIG. 4A). A major polypeptide of ~89 kDa, along with multiple related products displaying lower $M_r$, were obtained. The recombinant material was recognized by both anti-FLAG and GPBP-specific antibodies, guaranteeing the fidelity of the expression system. Again, however, the $M_r$ displayed by the major product was notably higher than predicted and even higher than the $M_r$ of the 293 cell-derived recombinant material, supporting the idea that GPBP undergoes important and differential post-translational modifications. Since phosphorylatable residues are abundant in the polypeptide chain, we investigated the existence of phosphoamino acids in the recombinant materials. By using monoclonal or polyclonal (not shown) antibodies against phosphoserine (Pser), phosphothreonine (PThr) and phosphotyrosine (PTyr), we identified the presence of all three phosphoresidues either in yeast RGPBP (FIG. 4B) or in 293 cell-derived material (not shown). The specificity of the antibodies was further assessed by partially inhibiting their binding by the addition of 5–10 mM of the corresponding phosphoamino acid (not shown). This suggests that the phosphoresidue content varies depending upon the cell expression system, and that the $M_r$ differences are mainly due to phosphorylation. Dephosphorylated yeast-derived material consistently displayed similar $M_r$ to the material derived from 293 cells, and phosphoamino acid content correlates with SDS-PAGE mobilities (FIG. 4C). As an in vivo measurement, the phosphorylation of RGPBP in the 293 cells was assessed (FIG. 4D). Control cells (lanes 1) and cells expressing RGPBP in a stable (lanes 2) or transient (lanes 3) mode were cultured in the presence of $H_3{}^{32}PO_4$. Immunoprecipitated recombinant material contained $^{32}P$, indicating that phosphorylation of GPBP occurred in vivo and therefore is likely to be a physiological process.

Figure 5:
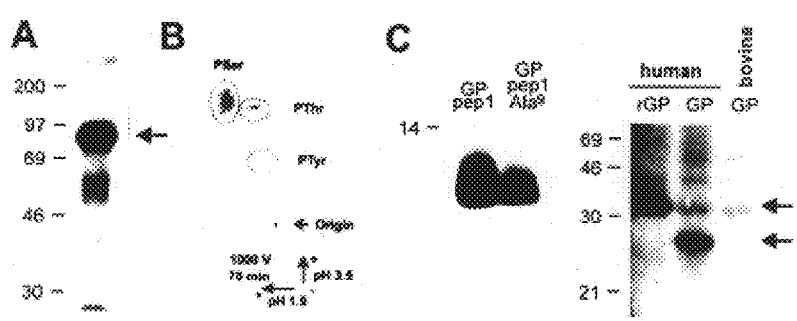
FIG. 5. Recombinant GPBP contains a serine/threonine kinase that specifically phosphorylates the N-terminal region of the human GP antigen. To assess phosphorylation, approximately 200 ng of yeast rGPBP was incubated with $[\gamma]^{32}$P-ATP in the absence (A and B) or presence (C) of GP antigen-derived material (C). In (A), the mixture was subjected to reducing SDS-PAGE (10% gel) and autoradiographed. In (B), the mixture was subjected to $^{32}$P-phosphoamino acid analysis by two-dimensional thin-layer chromatography. The dotted circles indicate the position of ninhydrin stained phosphoamino acids. In (C), the phosphorylation mixtures of the indicated GP-derived material were analyzed by SDS-PAGE (15% gel) and autoradiography (GPpep1 and GPpep1Ala$^9$) or immunoprecipitated with Mab 17, a monoclonal antibody that specifically recognize GP antigen from human and bovine origin, and analyzed by SDS-PAGE (12.5%) and autoradiography (rGP, GP). The relative positions of RGPBP (A), rGP antigen and the native human and bovine GP antigens (C) are indicated by arrows. The numbers and bars refer to molecular weight markers as in previous Figures.

The rGPBP is a Serine/threonine Kinase that Phosphorylates the N-terminal Region of the Human GP Antigen Although GPBP does not contain the conserved structural regions required to define the classic catalytic domain for a protein kinase, the recent identification and characterization of novel non-conventional protein kinases (19–27) encouraged the investigation of its phosphorylating activity. Addition of $[\gamma^{32}P]ATP$ to rGPBP (either from yeast or 293 cells (not shown)) in the presence of $Mn^{2+}$ and $Mg^{2+}$ resulted in the incorporation of $^{32}P$ as PSer and PThr in the major and related products recognized by both anti-FLAG and specific antibodies (FIGS. 5A and B), indicating that the affinity-purified material contains a Ser/Thr protein kinase. To further characterize this activity, GPpep1, GPpep1Ala$^9$ (a GPpep1 mutant with Ser$^9$ replaced by Ala), native and recombinant human GP antigens, and native bovine GP antigen were assayed (FIG. 5C). Affinity-purified rGPBP phosphorylates all human-derived material to a different extent. However, in similar conditions, no appreciable $^{32}P$-incorporation was observed in the bovine-derived substrate. The lower $^{32}P$ incorporation displayed by GPpep1Ala$^9$ when compared with GPpep1, and the lack of phosphorylation of the bovine antigen, indicates that the kinase present in rGPBP discriminates between human and bovine antigens, and that Ser$^9$ is a target for the kinase.

Figure 6:
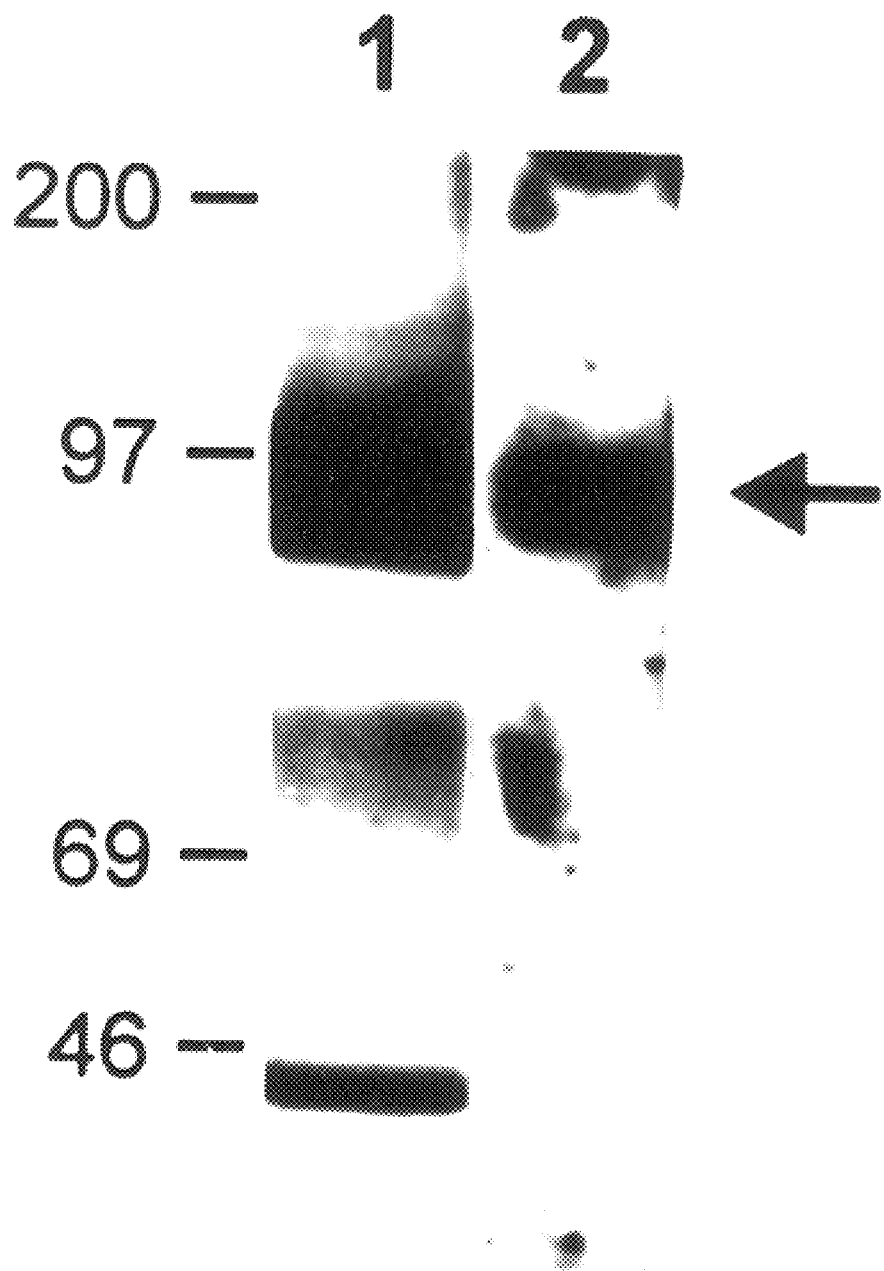
FIG. 6. In-blot renaturation of the serine/threonine kinase present in rGPBP. Five micrograms of rGPBP from yeast were in-blot renatured. The recombinant material was specifically identified by anti-FLAG antibodies (lane 1) and the in situ $^{32}$P-incorporation detected by autoradiography (lane 2). The numbers and bars refer to molecular weight markers as in previous Figures. The arrow indicates the position of the 89 kDa rGPBP polypeptide.

Although the purification system provides high quality material, the presence of contaminants with a protein kinase activity could not be ruled out. The existence of contaminants was also suggested by the presence of a FLAG-containing 40 kDa polypeptide, which displayed no reactivity with specific antibodies nor incorporation of $^{32}P$ in the phosphorylation assays (FIGS. 4A and 5A). To precisely identify the polypeptide harboring the protein kinase activity, we performed in vitro kinase renaturation assays after SDS-PAGE and Western-blotted (FIG. 6). We successfully combined the use of specific antibodies (lane 1) and autoradiographic detection of in situ $^{32}P$-incorporation (lane 2), and identified the 89 kDa rGPBP material as the primary polypeptide harboring the Ser/Thr kinase activity. The lack of $^{32}P$-incorporation in the rGPBP-derived products, as well as in the 40 kDa contaminant, further supports the specificity of the renaturation assays and locates the kinase activity to the 89 kDa polypeptide. Recently, it has been shown that traces of protein kinases intimately associated with a polypeptide can be released from the blot membrane, bind to, and phosphorylate the polypeptide during the labeling step (28). To assess this possibility in our system, we performed renaturation studies using a small piece of membrane containing the 89 kDa polypeptide, either alone or together with membrane pieces representing the different regions of the blot lane. We observed similar $^{32}P$-incorporation at the 89 kDa polypeptide regardless of the co-incubated pieces (not shown), indicating that if there are co-purified protein kinases in our sample they are not phosphorylating the 89 kDa polypeptide in the renaturation assays unless they co-migrate. Co-migration does not appear to be a concern, however, since rGPBP deletion mutants (GPBPΔ26 and R3; see below) displaying different mobilities also have kinase activities and could be similarly in-blot renatured (not shown).

Immunohistochemical Localization of the Novel Kinase

Figure 7:
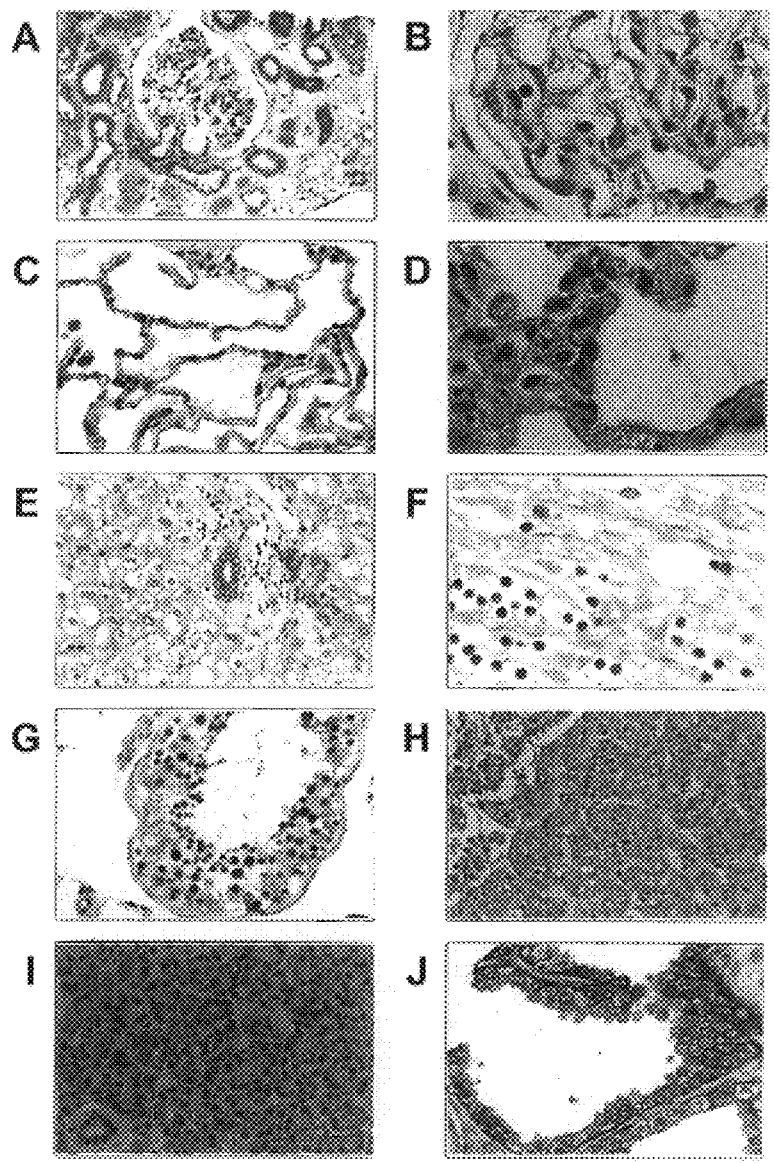
FIG. 7. Immunological localization of GPBP in human tissues. Rabbit serum against the N-terminal region of GPBP (1:50) was used to localize GPBP in human tissues. The tissues shown are kidney (A) glomerulus (B), lung (C), alveolus (D), liver (E), brain (F), testis (G), adrenal gland (H), pancreas (I) and prostate (J). Similar results were obtained using anti-GPBP affinity-purified antibodies or a pool of culture medium from seven different GPBP-specific monoclonal antibodies (anti-GPBP Mabs 3, 4, 5, 6, 8, 10 and 14). Rabbit pre-immune serum did not stain any tissue structure in parallel control studies. Magnification was 40× except in B and D where it was 100×.

To investigate GPBP expression in human tissues we performed immunohistochemical studies using specific polyclonal (FIG. 7) or monoclonal antibodies (not shown). Although GPBP is widely expressed in human tissues, it shows tissue and cell-specificity. In kidney, the major expression is found at the tubule epithelial cells and the glomerular mesangial cells and podocytes. At the lung alveolus, the antibodies display a linear pattern suggestive of a basement membrane localization, along with staining of pneumocytes. Liver shows low expression in the parenchyma, but high expression in biliary ducts. Expression in the central nervous system is observed in the white matter, but not in the neurons of the brain. In testis, a high expression in the spermatogonium contrasts with the lack of expression in Sertoli cells. The adrenal gland shows a higher level of expression in cortical cells versus the medullar. In the pancreas, GPBP is preferentially expressed in Langerhans islets versus the exocrine moiety. In prostate, GPBP is expressed in the epithelial cells but not in the stroma (FIG. 7). Other locations with high expression of GPBP are striated muscle, epithelial cells of intestinal tract, and Purkinje cells of the cerebellum (not shown). In general, in tissues where GPBP is highly expressed the staining pattern is mainly diffuse cytosolic. However in certain locations there is, in addition, an important staining reinforcement at the nucleus (spermatogonium), at the plasma membrane (pneumocyte, hepatocyte, prostate epithelial cells, white matter) or at the extracellular matrix (alveolus) (FIG. 7).

DISCUSSION

Our data show that GPBP is a novel, non-conventional serine/threonine kinase. We also present evidence that GPBP discriminates between human and bovine GP antigens, and targets the phosphorylatable region of human GP antigen in vitro. Several lines of evidence indicate that the 89 kDa polypeptide is the only kinase in the affinity purified rGPBP. First, we found no differences in auto- or trans-phosphorylation among RGPBP samples purified in the presence of 150 mM, 0.5 M, 1 M or 2 M salt (not shown), suggesting that RGPBP does not carry intimately bound kinases. Second, there is no FLAG-containing, yeast-derived kinase in our samples, since material purified using GPBP-specific antibodies shows no differences in phosphorylation (not shown). Third, a deletion mutant (GPBPΔ26; see below) displays reduced auto- and trans-phosphorylation activities (not shown), demonstrating that the 89 kD polypeptide is the only portion of the rGPBP with the ability to carry out phosphate transfer.

Although GPBP is not homologous to other non-conventional kinases, they share some structural features including an N-terminal α-helix coiled-coil (26, 27), serine-rich motifs (24), high phosphoamino acids content (27), bipartite nuclear localization signal (27), and the absence of a typical nucleotide or ATP binding motif (24, 27).

Immunohistochemistry studies show that GPBP is a cytosolic polypeptide also found in the nucleus, associated with the plasma membrane and likely at the extracellular matrix associated with the basement membrane, indicating that it contains the structural requirements to reach all these destinations. The nuclear localization signal and the PH domain confer to it the potential to reach the nucleus and the cell membrane, respectively (17, 29, 30). Although GPBP does not contain the structural requirements to be exported, the 5'-end untranslated region of its mRNA includes an upstream ORF of 130 residues with an in-frame stop codon at the beginning (FIG. 1). A mRNA editing process inserting a single base pair (U) would generate an operative in-frame start site and an ORF of 754-residues containing an export signal immediately downstream of the edited Met (not shown). Polyclonal antibodies against a synthetic peptide representing part of this hypothetical extra-sequence (PRSARCQARRRRGGRTSS (SEQ ID NO:33)) display a linear vascular reactivity in human.tissues suggestive of an extracellular basement membrane localization (data not shown).

Alternatively, a splicing phenomenon could generate transcripts with additional unidentified exon(s) that would provide the structural requirements for exportation. The multiple cellular localization, the high content in PTyr, and the lack of tyrosine kinase activity in vitro, suggest that GPBP is itself the target of specific tyrosine kinase(s) and therefore likely involved in specific signaling cascade(s).

As discussed above, specific serine phosphorylation, as well as pre-mRNA alternative splicing, are associated with the biology of several autoantigens, including the GP antigen, acetylcholine receptor and myelin basic protein (MBP) (4). The latter is suspected to be the major antigen in multiple sclerosis (MS), another exclusively human autoimmune disease in which the immune system targets the white matter of the central nervous system. GP disease and MS are human disorders that display a strong association with the same HLA class II haplotype (HLA DRB1*1501)(32, 33). This, along with the recent report of death by GP disease of a MS patient carrying this HLA specificity (34), supports the existence of common pathogenic events in these human disorders.

Phosphorylation of specific serines has been shown to change intracellular proteolysis (35–40). Conceivably, alterations in protein phosphorylation can affect processing and peptide presentation, and thus mediate autoimmunity. GP antigen-derived peptide presentation by the HLA-DR15 depends more on processing than on preferences of relatively indiscriminate DR15 molecules (41), suggesting that if processing is influenced by abnormal phosphorylation, the resulting peptides would likely be presented by this HLA. Our more recent data indicate that in both the GP and MBP systems, the production of alternative splicing products serves to regulate the phosphorylation of specific and structurally homologous PKA sites, suggesting that this or a closely related kinase is the in vivo phosphorylating enzyme. Alterations in the degree of antigen phosphorylation, caused either by an imbalance in alternative products, or by the action of an intruding kinase that deregulates phosphorylation of the same motifs, could lead to an autoimmune response in predisposed individuals. rGPBP phosphorylates the human GP antigen at a major PKA phosphorylation site in an apparently unregulated fashion, since the presence of specific alternative products of the GP antigen did not affect phosphorylation of the primary antigen by GPBP (not shown).

Although GPBP is ubiquitously expressed, in certain organs and tissues it shows a preference for cells and tissue structures that are target of common autoimmune responses: the Langerhans cells (type I diabetes); the white matter of the central nervous system (multiple sclerosis); the biliary ducts (primary biliary cirrhosis); the cortical cells of the adrenal gland (Addison disease); striated muscle cells (myasthenia gravis); spermatogonium (male infertility); Purkinje cells of the cerebellum (paraneoplasic cerebellar degeneration syndrome); and intestinal epithelial cells (pernicious anemia, autoimmune gastritis and enteritis). All the above observations point to this novel kinase as an attractive candidate to be considered when envisioning a model for human autoimmune disease.

REFERENCES FOR THE BACKGROUND AND EXAMPLE 1

1 Saus, J. (1998) *Goodpasture's Syndrome*. Encyclopedia of Immunology, 2nd Ed., Delves, P. J., and Roitt, I. M. Eds., Academic Press Limited, London,UK
2 Leinonen, A., Mariyama, M., Mochizuki, T., Tryggvason, K., and Reeders, S. T. (1994) *J. Biol. Chem.* 269, 26172–26177
3 Quinones, S., Bernal, D., García-Sogo, M., Elena, S. F., and Saus, J. (1992) *J. Biol. Chem.* 267, 19780–19784
4 Revert, F., Penadés J. R., Plana, M., Bernal, D., Johansson, C., Itarte, E., Cervera, J., Wieslander, J., Quinones, S., and Saus, J. (1995) *J. Biol. Chem.* 270, 13254–13261
5 Bernal, D., Quinones, S., and Saus, J. (1993) *J. Biol. Chem.* 268, 12090–12094
6 Feng, L., Xia, Y., and Wilson, C. B. (1994) *J. Biol. Chem.* 269, 2342–2348
7 Penadés, J. R., Bernal, D., Revert, F., Johansson, C., Fresquet, V. J., Cervera, J., Wieslander, J., Quinones, S., and Saus, J. (1995) *Eur. J. Biochem.* 229, 754–760
8 Sambrook, J., Fritsch, E. F., and Maniatis, T. (1989) *Molecular Cloning: A Laboratory Manual*, $2^{nd}$ Ed., Cold Spring Harbor Laboratory, Cold Spring Harbor, N.Y.
9 Coligan, J. E., Dunn, B. N., Ploegh, H. L., Speicher, D. W., and Winfield, P. T. (1995–97) *Current Protocols in Protein Science*, John Wiley & Sons Eds., New York, N.Y.
10 Ausubel, F. M., Brent, R., Kingston, R. E., Moore, D. D., Deidman, J. G., Smith, J. A., and Struhl, K. (1994–98) *Current Protocols in Molecular Biology*, John Wiley & Sons Eds., New York, N.Y.
11 Ferrel, J. E., and Martin, G. S. (1991) *Methods in Enzymology* 200, 430–435
12 Boyle, W. J., van der Geer, P., and Hunter, T. (1991) *Methods in Enzymology* 201, 110–149
13 Hsu, S. M., Raine, L., and Fanger, H. (1981) *J. Histochem. Cytochem.* 29, 577–580
14 Altschul, S. F., Madden, T. L., Schaffer, A. A., Zhang, J., Zhang, Z., Miller, W., and Lipman, D. J. (1997) *Nucleic Acids Res.* 25, 3389–3402
15 Bairoch, A., Bucher, P., and Hofmann, K. (1997) *Nucleic Acids Res.* 25, 217–221

16 Lupas, A. (1996) *Trends Biochem. Sci.* 21, 375–382
17 Lemmon, M. A., Falasca, M., Ferguson, K. M., and Schlessinger, J. (1997) *Trends Cell Biol.* 7, 237–242
18 Boulikas, T. (1993) *Crit. Rev. Eukaryot. Gene Expr.* 3, 193–227
19 Csermely, P., and Kahn, C. R. (1991) *J. Biol. Chem.* 266, 4943–4950
20 Maru, Y., and Witte, O. N. (1991) *Cell* 67, 459–468
21 Beeler, J. F., LaRochelle, W. J., Chedid, M., Tronick, S. R., and Aaronson, S. A. (1994) *Mol. Cell. Biol.* 14, 982–988
22 Csermely, P., Miyata, Y., Schnaider, T., and Yahara, I. (1995) *J. Biol. Chem.* 270, 6381–6388
23 Dikstein, R., Ruppert, S., and Tjian, R. (1996) *Cell* 84, 781–790
24 Eichinger, L., Bomblies, L., Vandekerckhove, J., Schleicher, M., and Gettermans, J. (1996) *EMBO J.* 15,5547–5556
25 Côté, G. P., Luo, X., Murphy, M. B., and Egelhoff, T. T. (1997) *J. Biol. Chem.* 272, 6846–6849
26 Ryazanov, A. G., Ward, M. D., Mendola, C. E., Pavur, K. S., Dorovkov, M. V., Wiedmann, M., Erdjument-Bromage, H., Tempst, P., Parmer, T. G., Prostko, C. R., Germino, F. J., and Hait, W. N. (1997) *Proc. Natl. Acad. Sci. USA* 94, 4884–4889
27 Fraser, R. A., Heard, D. J., Adam, S., Lavigne, A. C., Le Douarin, B., Tora, L., Losson, R., Rochette-Egly, C., and Chambon, P. (1998) *J. Biol. Chem.* 273, 16199–16204
28 Langelier, Y., Champoux, L., Hamel, M., Guilbault, C., Lamarche, N., Gaudreau, P., and Massie, B. (1998) *J. Biol. Chem.* 273, 1435–1443
29 Lemmon, M. A., and Ferguson, K. M. (1998) *Curr. Top. Microbiol. Immunol.* 228, 39–74
30 Rebecchi, M. J., and Scarlata, S. (1998) *Annu. Rev. Biophys. Biomol. Struct.* 27, 503–528
31 Roitt, I. (1994) *Autoimmune diseases in Essential Immunology*, 383–439, 8th Ed., Blackwell Scientific, Oxford, UK
32 Erlich, H., and Apple, R. (1998) *MHC disease associations. Encyclopedia of Immunology*, 2nd Ed., Delves, P. J., and Roitt, I. M. Eds., Academic Press Limited, London, UK
33 Phelps, R. G., Turner, A. N., and Rees, A. J. (1996)*J. Biol. Chem.* 271, 18549–18553
34 Henderson, R. D., Saltissi, D., and Pender, M. P. (1998) *Acta Neurol. Scand.* 98, 134–135
35 Litersky, J. M., and Johnson, G. V. W. (1992) *J. Biol. Chem.* 267, 1563–1568.
36 Brown, K., Gerstberger, S., Carlson, L., Franzoso, G., and Siebenlist, U. (1995) *Science* 267, 1485–1488
37 Chen, Z. J., Parent, L., and Maniatis, T. (1996) *Cell* 84, 853–862
38 Aberle, H., Bauer, A., Stappert, J., Kispert, A., and Kemler, R. (1997) *EMBO J.* 16, 3797–3804
39 Regnier, C. H., Song, H. Y., Gao, X., Goeddel, D. V., Cao, Z., and Rothe, M. (1997) *Cell* 90, 373–383
40 Vlach, J., Hennecke, S., and Amati, B. (1997) *EMBO J.* 16, 5334–5344
41 Phelps, R. G., Jones, V. L., Coughlan, M., Turner, A. N., and Rees, A. J. (1998) *J. Biol. Chem.* 273, 11440–11447

EXAMPLE 2

GPBP Alternative Splicing

Here we report the existence of two isoforms of GPBP that are generated by alternative splicing of a 78-base pair (bp) long exon that encodes a 26-residue serine-rich motif. Both isoforms, GPBP and GPBPΔ26, exist as high molecular aggregates that result from polypeptide self-aggregation. The presence of the 26-residue peptide in the polypeptide chain results in a molecular species that self-interacts more efficiently and forms aggregates with higher specific activity. Finally, we present evidences supporting the observation that GPBP is implicated in human autoimmune pathogenesis.

MATERIAL AND METHODS

Synthetic polymers
Peptides
GPpep1, KGKRGDSGSPATWTTRGFVFT (SEQ ID NO:26), is described in Example 1. GPBPpep1, PYSRSSSMSSIDLVSASDDVHRFSSQ (SEQ ID NO:14), representing residues 371–396 of GPBP was synthesized by Genosys.
Oligonucleotides
The following oligonucleotides were synthesized by Life Technologies, Inc., 5' to 3': ON-GPBP-11m, G CGG GAC TCA GCG GCC GGA TTT TCT (SEQ ID NO:34); ON-GPBP-15m, AC AGC TGG CAG AAG AGA C (SEQ ID NO:35); ON-GPBP-20c, C ATG GGT AGC TTT TAA AG (SEQ ID NO; 36); ON-GPBP-22m, TA GAA GAA CAG TCA CAG AGT GAA AAG G (SEQ ID NO;37); ON-GPBP-53c, GAATTC GAA CAA AAT AGG CTT TC (SEQ ID NO:38); ON-GPBP-56m, CCC TAT AGT CGC TCT TC (SEQ ID NO:39); ON-GPBP-57c, CTG GGA GCT GAA TCT GT (SEQ ID NO:40); ON-GPBP-62c, GTG GTT CTG CAC CAT CTC TTC AAC (SEQ ID NO:41); ON-GPBP-Δ26, CA CAT AGA TTT GTC CAA AAG GTT GAA GAG ATG GTG CAG AAC (SEQ ID NO:42).
Reverse Transcriptase and Polymerase Chain Rection (RT-PCR)
Total RNA was prepared from different control and GP tissues as described in (15). Five micrograms of total RNA was retrotranscribed using Ready-To-Go You-Prime First-Strand beads (Amersham Pharmacia Biotech) and 40 pmol of ON-GPBP-53c. The corresponding cDNA was subjected to PCR using the pairs of primers ON-GPBP-11m/ON-GPBP-53c or ON-GPBP-15m/ON-GPBP-62c. The identity of the products obtained with 15m-62c was further confirmed by Alu I restriction. To specifically amplify GPBP transcripts, PCR was performed using primers ON-GPBP-15m/ON-GPBP-57c.
Northern Hybridization Studies
Pre-made human multiple-tissue and tumor cell-line Northern Blots (CLONTECH) were probed with a cDNA containing the 78-bp exon present only in GPBP or with a cDNA representing both isoforms. The corresponding cDNAs were obtained by PCR using the pair of primers ON-GPBP-56m and ON-GPBP-57c using GPBP as a template, or with primers ON-GPBP-22m and ON-GPBP-20c, using GPBPΔ26 as a template. The resulting products were random-labeled and hybridized following the manufacturers' instructions.
Plasmid Construction, Expression and Purification of Recombinant Proteins
The plasmid pHIL-FLAG-n4', used for recombinant expression of FLAG-tagged GPBP in *Pichia pastoris* has been described elsewhere (4). The sequence coding for the 78-bp exon was deleted by site-directed mutagenesis using ON-GPBP-Δ26 to generate the plasmid pHIL-FLAG-n4'Δ26. Expression and affinity-purification of recombinant GPBP and GPBPΔ26 was done as in (4).
Gel-filtration HPLC
Samples of 250 μl were injected into a gel filtration PE-TSK-G4000SW HPLC column equilibrated with 50 mM Tris-HCl pH 7.5, 150 mM NaCl. The material was eluted from the column at 0.5 ml/min, monitored at 220 nm and minute fractions collected.

In vitro Phosphorylation Assays

The auto-, trans-phosphorylation and in-blot renaturation studies were performed as in Example 1.

Antibodies and Immunochemical Techniques

Polyclonal antibodies were raised by in chicken against a synthetic peptide (GPBPpep1) representing the sequence coded by the 78-bp exon (Genosys). Egg yolks were diluted 1:10 in water, the pH adjusted to 5.0. After 6 hours at 4° C., the solution was clarified by centrifugation (25 min at 10000×g at 4° C.) and the antibodies precipitated by adding 20% (w/v) of sodium sulfate at 20,000×g, 20'. The pellets were dissolved in PBS (1 ml per yolk) and used for immunohistochemical studies. The production of antibodies against GPBP/GPBPΔ26 or against α3(IV)NC1 domain are discussed above (see also 4, 13).

Sedimentation Velocity

Determination of sedimentation velocities were performed in an Optima XL-A analytical ultracentrifuge (Beckman Instruments Inc.), equipped with a VIS-UV scanner, using a Ti60 rotor and double sector cells of Epon-charcoal of 12 mm optical path-length. Samples of ca. 400 μl were centrifuged at 30,000 rpm at 20° C. and radial scans at 220 nm were taken every 5 min. The sedimentation coefficients were obtained from the rate of movement of the solute boundary using the program XLAVEL (supplied by Beckman).

Sedimentation Equilibrium

Sedimentation equilibrium experiments were done as described above for velocity experiments with samples of 70 μl, and centrifuged at 8,000 rpm. The experimental concentration gradients at equilibrium were analyzed using the program EQASSOC (Beckman) to determine the corresponding weight average molecular mass. A partial specific volumes of 0.711 $cm^3$/g for GPBP and 0.729 $cm^3$/g for GPBPΔ26 were calculated from the corresponding amino acid compositions.

Physical Methods and Immunochemical Techniques

SDS-PAGE and Western blotting were performed under reducing conditions as previously described (3). Immunohistochemistry studies were done on formalin fixed paraffin embedded tissues using the ABC peroxidase method (4) or on frozen human biopsies fixed with cold acetone using standard procedures for indirect immunofluorescence.

Two Hybrid Studies

Self-interaction studies were carried out in *Saccharomyces cerevisiae* (HF7c) using pGBT9 and pGAD424 (CLONTECH) to generate GAL4 binding and activation domain-fusion proteins, respectively. Interaction was assessed following the manufacture's recommendations. β-galactosidase activity was assayed with X-GAL (0.75 mg/ml) for in situ and with ortho-nitrophenyl β-D galactopyranoside (0.64 mg/ml) for the in-solution determinations.

RESULTS

Identification of Two Spliced GPBP Variants

Figure 8:
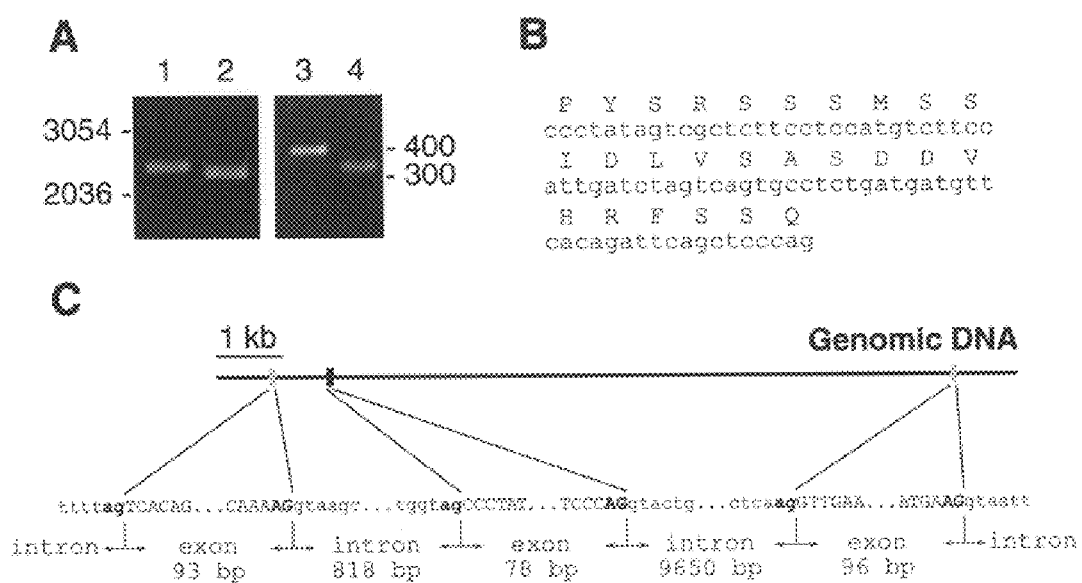
FIG. 8. GPBPΔ26 is a splicing variant of GPBP. (A) Total RNA from normal skeletal muscle was retrotranscribed using primer 53c and subsequently subjected to PCR with primers 11m-53c (lane 2) or 15m-62c (lane 4). Control amplifications of a plasmid containing GPBP cDNA using the same pairs of primers are shown in lanes 1 and 3. Numbers on the left and right refer to molecular weight in base pairs. The region missing in the normal muscle transcript was identified and its nucleotide sequence (lower case; SEQ ID NO: 13) and deduced amino acid sequence (upper case; SEQ ID NO: 14) are shown in (B). A clone of genomic DNA comprising the cDNA region of interest was sequenced and its structure is drawn in (C), showing the location and relative sizes of the 78-bp exon spliced out in GPBPΔ26 (black box), adjacent exons (gray boxes), and introns (lines). The size of both intron and exons is given and the nucleotide sequence of intron-exon boundaries (SEQ ID NOs: 55–60) is presented, with consensus for 5' and 3' splice sites shown in bold case.

To characterize the GPBP species in normal human tissues, we coupled reverse transcription to a polymerase chain reaction (RT-PCR) on total RNA from different tissues, using specific oligonucleotides that flank the full open reading frame of GPBP. A single cDNA fragment displaying lower size than expected was obtained from skeletal muscle-derived RNA (FIG. 8A), and from kidney, lung, skin, or adrenal gland-derived RNA (not shown). By combining nested PCR re-amplifications and endonuclease restriction mapping, we determined that all the RT-PCR products corresponded to the same molecular species (not shown). We fully sequenced the 2.2-Kb of cDNA from human muscle and found it identical to HeLa-derived material except for the absence of 78-nucleotides (positions 1519–1596), which encode a 26-residues motif (amino acids 371–396) (FIG. 8B). We therefore named this more common isoform of GPBP as GPBPΔ26.

To investigate whether the 78-bp represent an exon skipped transcript during pre-mRNA processing, we used this cDNA fragment to probe a human-derived genomic library and we isolated a ~14-Kb clone. By combining Southern blot hybridization and PCR, the genomic clone was characterized and a contiguous DNA fragment of 12482-bp was fully sequenced (SEQ ID 25). The sequence contained (from 5' to 3'), 767-bp of intron sequence, a 93-bp exon, an 818-bp intron, the 78-bp exon sequence of interest, a 9650-bp intron, a 96-bp exon and a 980-bp intron sequence (FIG. 8C). The exon-intron boundaries determined by comparing the corresponding DNA and cDNA sequences meet the canonical consensus for 5' and 3' splice sites (FIG. 8C) (5), thus confirming the exon nature of the 78-bp sequence. The GPBP gene was localized to chromosome 5q13 by fluorescence in situ hybridization (FISH) using the genomic clone as a probe (not shown).

Figure 9:
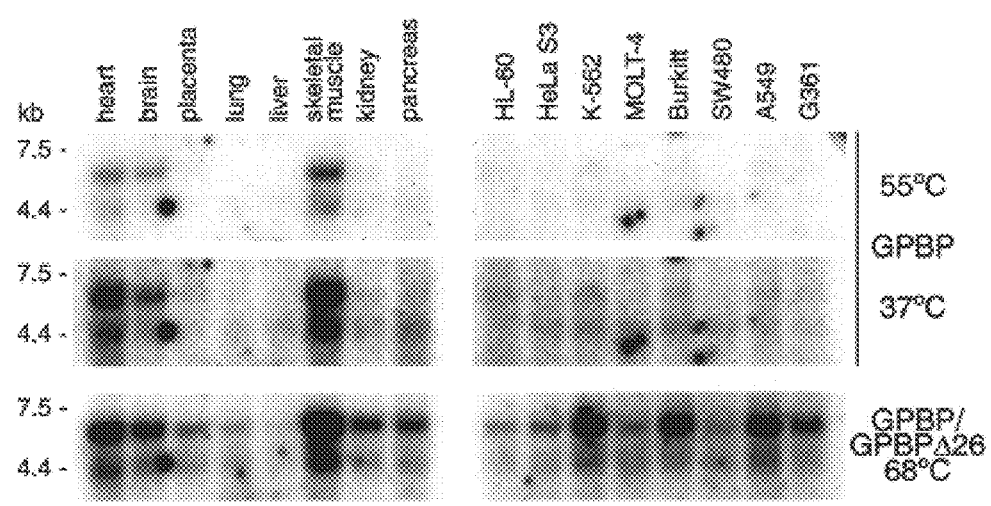
FIG. 9. Differential expression of GPBP and GPBPΔ26. Fragments representing the 78-bp exon (GPBP) or flanking sequences common to both isoforms (GPBP/GPBPΔ26) were $^{32}$P-labeled and used to hybridize human tissue and tumor cell line Northern blots (CLONTECH). The membranes were first hybridized with GPBP-specific probe, stripped and then reanalyzed with GPBP/GPBPΔ26 probe. Washing conditions were less stringent for GPBP-specific probe (0.1% SSPE, 37° C. or 55° C.) than for the GPBP/GPBPΔ26 (0.1% SSPE, 68° C.) to increase GPBP and GPBPΔ26 signals respectively. No detectable signal was obtained for the GPBP probe when the washing program was at 68° C. (not shown).

The relative expression of GPBP in human-derived specimens was assessed by Northern blot analysis, using either the 78-bp exon or a 260-bp cDNA representing the flanking sequence of 78-bp (103-bp 5' and 157-bp 3') present in both GPBP and GPBPΔ26 (FIG. 9). The 78-bp containing the molecular species of interest were preferably expressed in striated muscle (both skeletal and heart) and brain, and poorly expressed in placenta, lung and liver. In contrast to GPBPΔ26, the GPBP was expressed at very low levels in kidney, pancreas and cancer cell lines.

All the above indicates that GPBP is expressed at low levels in normal human tissues, and that the initial lack of detection by RT-PCR of GPBP can be attributed to a preferential amplification of the more abundant GPBPΔ26. Indeed, the cDNA of GPBP could be amplified from human tissues (skeletal muscle, lung, kidney, skin and adrenal gland) when the specific RT-PCR amplifications were done using 78-bp exon-specific oligonucleotides (not shown). This also suggests that GPBPΔ26 mRNA is the major transcript detected in Northern blot studies when using the cDNA probe representing both GPBP and GPBPΔ26.

Recombinant Expression and Functional Characterization of GPBPΔ26

Figure 10:
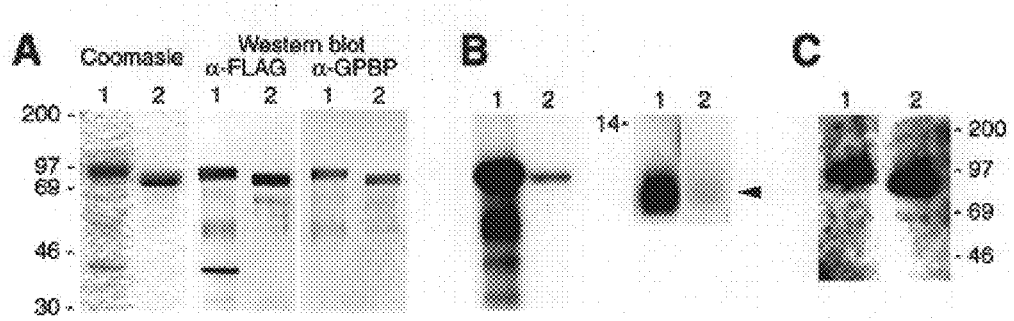
FIG. 10. GPBPΔ26 displays lower phosphorylating activity than GPBP. (A) Recombinantly-expressed, affinity-purified GPBP (rGPBP) (lanes 1) or rGPBPΔ26 (lanes 2) were subjected to SDS-PAGE under reducing conditions and either Coomasie blue stained (2 μg per lane) or blotted (200 ng per lane) with monoclonal antibodies recognizing the FLAG sequence (α-FLAG) or GPBP/GPBPΔ26 (Mab14). (B) 200 ng of rGPBP (lanes 1) or rGPBPΔ26 (lanes 2) were in vitro phosphorylated without substrate to assay autophosphorylation (left), or with 5 nmol GPpep1 to measure trans-phosphorylation activity (right). An arrowhead indicates the position of the peptide. (C) 3 μg of rGPBP (lane 1) or rGPBPΔ26 (lane 2) were in-blot renatured as described under Material and Methods. The numbers and bars indicate the molecular mass in kDa and the relative position of the molecular weight markers, respectively.

To investigate whether the absence of the 26-residue serine-rich motif would affect the biochemical properties of GPBP, we expressed and purified both isoforms (rGPBP and rGPBPΔ26), and assessed their auto- and trans-phosphorylation activities (FIG. 10). As reported above for rGPBP (see also 4), rGPBPΔ26 is purified as a single major polypeptide and several related minor products (FIG. 10A). However, the number and relative amounts of the derived products vary compared to rGPBP, and they display $M_r$ on SDS-PAGE that cannot be attributed simply to the 26-residue deletion. This suggests that the 26-residue motif has important structural and functional consequences that could account for the reduced in-solution auto- and trans-phosphorylation activities displayed by rGPBPΔ26 (FIG. 10B). Interestingly, the differences in specific activity shown in the in-solution assays were not evident when autophosphorylation was assessed in-blot after SDS-PAGE and renaturation, suggesting that the 26-residue motif likely has important functional consequences at the quaternary structure level. Renaturation studies further showed that phosphate transfer activities reside in the major polypeptides representing the proposed open reading frames, and are not detectable in derived minor products.

rGPBP and rGPBP-26 Exist as Very Active High Molecular Weight Aggregates

Figure 11:
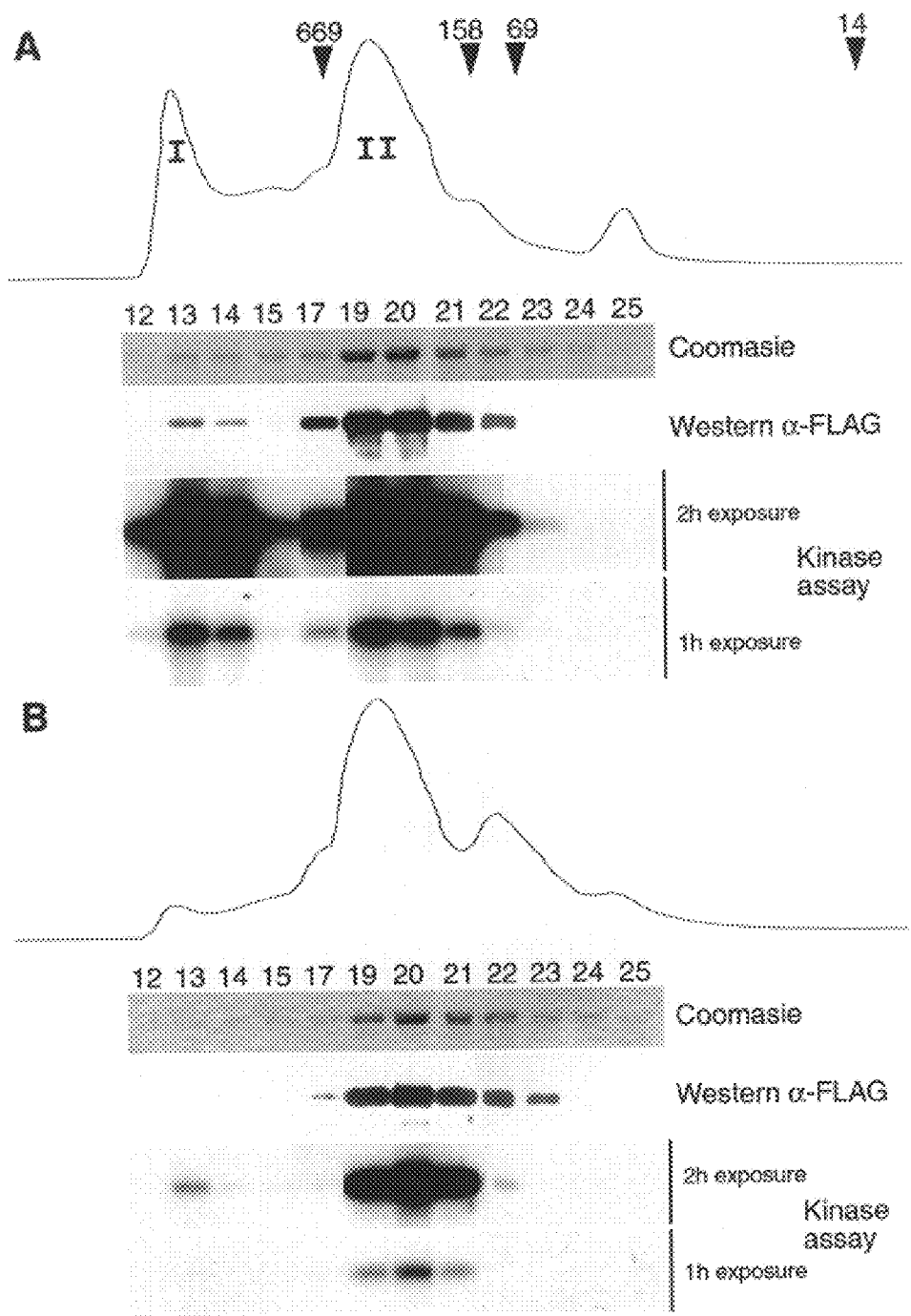
FIG. 11. rGPBP and rGPBPΔ26 form very active high molecular weight aggregates. About 300 μg of rGPBP (A) or rGPBPΔ26 (B) were subjected to gel filtration HPLC as described under Material and Methods. Vertical arrowheads and numbers respectively indicate the elution profile and molecular mass (kDa) of the molecular weight standards used. Larger aggregates eluted in the void volume (I), and the bulk of the material present in the samples eluted in the fractionation range of the column as a second peak between the 669 and 158 kDa markers (II). Fifteen microliters of the indicated minute fractions were subjected to SDS-PAGE and Coomasie blue staining. Five microliters of the same fractions were in vitro phosphorylated as described in Materials and Methods, and the reaction stopped by boiling in SDS sample buffer. The fractions were loaded onto SDS-PAGE, transferred to PVDF and autoradiographed for 1 or 2 hours using Kodak X-Omat films and blotted using anti-FLAG monoclonal antibodies (Sigma).

Gel filtration analysis of affinity-purified rGPBP or rGPBPΔ26 yielded two chromatographic peaks (I and II), both displaying higher MW than expected for the individual molecular species, as determined by SDS-PAGE studies (89 kDa and 84 kDa, respectively ) (FIG. 11). The bulk of the recombinant material eluted as a single peak between the 158 kDa and the 669 kDa molecular weight markers (peak II), while limited amounts of RGPBP and only traces of rGPBPΔ26 eluted in peak I (>1000 kDa). Aliquots of fractions representing each chromatographic profile were subjected to SDS-PAGE and stained, or incubated in the presence of $^{32}$P[γ] ATP, and analyzed by immunoblot and autoradiography. Along with the major primary polypeptide, every chromatographic peak contained multiple derived products of higher or lower sizes indicating that the primary polypeptide associates to form high molecular weight aggregates that are stabilized by covalent and non-covalent bonds (not shown). The kinase activity also exhibited two peaks coinciding with the chromatographic profiles. However, peak I showed a much higher specific activity than peak II, indicating that these high molecular weight aggregates contained a much more active form of the kinase. Equal volumes of rGPBP fractions number 13 and 20 exhibited comparable phosphorylating activity, even though the protein content is approximately 20 times lower in fraction 13, as estimated by Western blot and Coomasie blue staining (FIG. 11A). The specific activities of rGPBP and rGPBPΔ26 at peak II are also different, and are consistent with the studies shown for the whole material, thus supporting the hypothesis that the presence of the 26-rediue serine-rich motif renders a more active kinase. These results also suggest that both rGPBP and rGPBPΔ26 exist as oligomers under native conditions, and that both high molecular weight aggregate formation and specific activity are greatly dependent on the presence of the 26-residue serine-rich motif. Analytical centrifugation analysis of rGPBP revealed that peak I contained large aggregates (over $10^7$ Da). Peak II of rGPBP contained a homogenous population of 220±10 kDa aggregates, likely representing trimers with a sedimentation coefficient of 11S. Peak II of rGPBPΔ26 however consisted of a more heterogenous population that likely contains several oligomeric species. The main population (ca. 80%) displayed a weight average molecular mass of 310±10 kDa and a coefficient of sedimentation of 14S.

GPBP and GPBPΔ26 Self-interact in a Yeast Two-hybrid System

Figure 12:
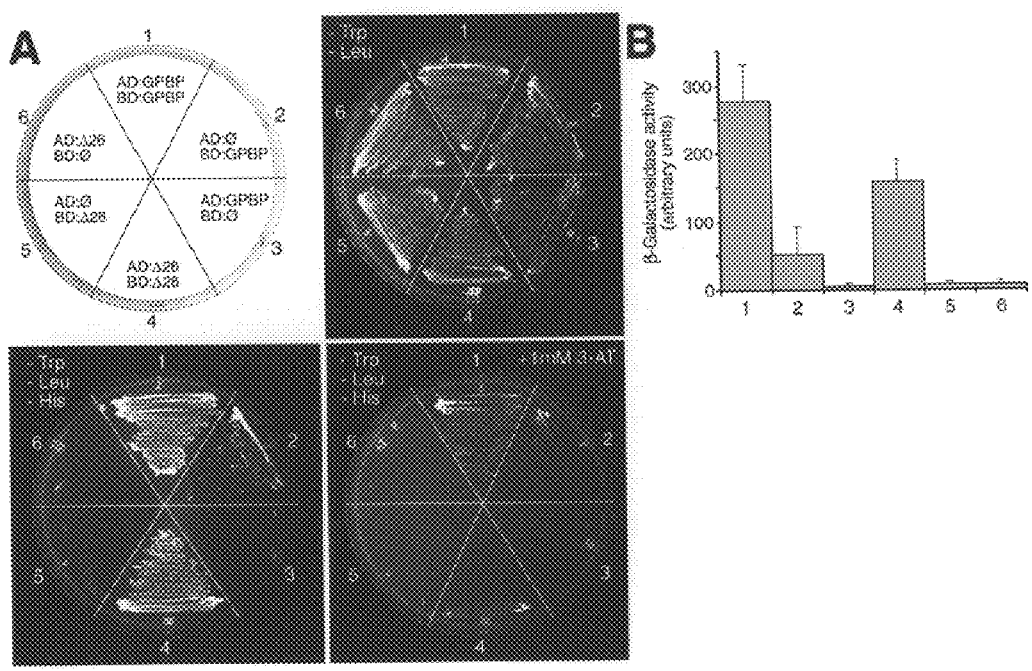
FIG. 12. Self-interaction of GPBP and GPBPΔ26 assessed by a yeast two-hybrid system. (A) Cell transfected for the indicated combinations of plasmids were selected on leucine-tryptophan-deficient medium (-Trp, -Leu), and independent transformants restreaked onto histidine-deficient plates (-Trp, -Leu, -His) in the presence or absence of 1 mM 3-amino-triazole (3-AT), to assess interaction. The picture was taken 3 days after streaking. (B) The bars represent mean values in β-galactosidase arbitrary units of four independent β-galactosidase in-solution assays.

To assess the physiological relevance of the self-aggregation, and to determine the role of the 26-residue motif, we performed comparative studies using a two-hybrid interaction system in yeast. In this type of study, the polypeptides whose interaction is under study are expressed as a part of a fusion protein containing either the activation or the binding domains of the transcriptional factor GAL4. An effective interaction between the two fusion proteins through the polypeptide under study would result in the reconstitution of the transcriptional activator and the subsequent expression of the two reporter genes, Lac Z and His3, allowing colony color detection and growth in a His-defective medium, respectively. We estimated the intensity of interactions by the growth-rate in histidine-defective medium, in the presence of different concentrations of a competitive inhibitor of the His3 gene product (3-AT), and a quantitative colorimetric liquid β-galactosidase assay. A representative experiment is presented in FIG. 12. When assaying GPBPΔ26 for self-interaction, a significant induction of the reporter genes was observed, while no expression was detectable when each fusion protein was expressed alone or with control fusion proteins. The insertion of the 26-residue motif in the polypeptide to obtain GPBP resulted in a notable increase in polypeptide interaction. All of the above data indicate that GPBPΔ26 self-associates in vivo, and that the insertion of the 26-residues into the polypeptide chain yields a more interactive molecular species.

Figure 13:
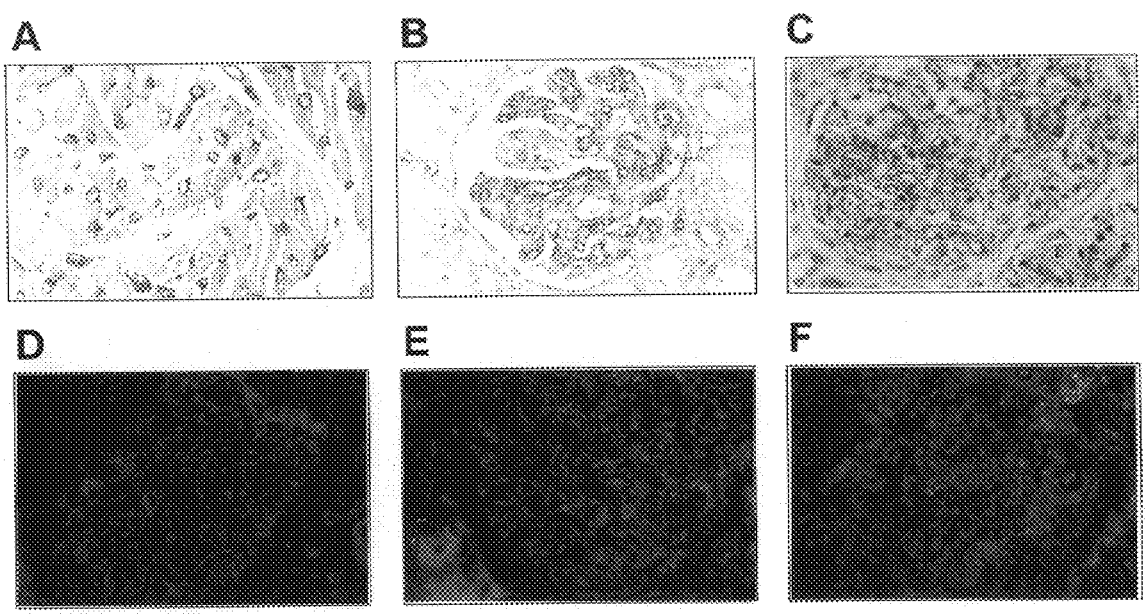
FIG. 13. GPBP is expressed associated with endothelial and glomerular basement membranes. Paraffin embedded sections of human muscle (A) or renal cortex (B, C) were probed with GPBP-specific antibodies (A,B) or with Mab189, a monoclonal antibody specific for the human α3(IV)NC1 (C). Frozen sections of human kidney (D-F) were probed with Mab17, a monoclonal antibody specific for the α3(IV)NC1 domain (D), GPBP-specific antibodies (E), or sera from a GP patient (F). Control sera (chicken pre-immune and human control) did not display tissue-binding in parallel studies (not shown).

GPBP is Highly Expressed in Human But Not in Bovine and Murine Glomerulus and Alveolus We have shown that GPBP/GPBPΔ26 is preferentially expressed in human cells and tissues that are commonly targeted in naturally occurring autoimmune responses. To specifically investigate the expression of GPBP, we raised polyclonal antibodies against a synthetic peptide representing the 26-residue motif characteristic of this kinase isoform, and used it for immunohistochemical studies on frozen or formalin fixed paraffin embedded human tissues (FIG. 13). In general, these antibodies showed more specificity than the antibodies recognizing both isoforms for the tissue structures that are target of autoimmune responses such as the biliary ducts, the Langerhans islets or the white matter of the central nervous system (not shown). Nevertheless, the most remarkable finding was the presence of linear deposits of GPBP-selective antibodies around the small vessels in every tissue studied (A), suggesting that GPBP is associated with endothelial basement membranes. Consequently, at the glomerulus, the anti-GPBP antibodies displayed a vascular pattern closely resembling the glomerular basement membrane staining yielded either by monoclonal antibodies specifically recognizing the α3(IV)NC1 (compare 13B with 13C and 13D), or by circulating GP autoantibodies (compare 13E and 13F). These observations further supported the initial observation that GPBP is expressed in tissue structures targeted in natural autoimmune responses, suggesting that the expression of GPBP is a risk factor and makes the host tissue vulnerable to an autoimmune attack.

Figure 14:
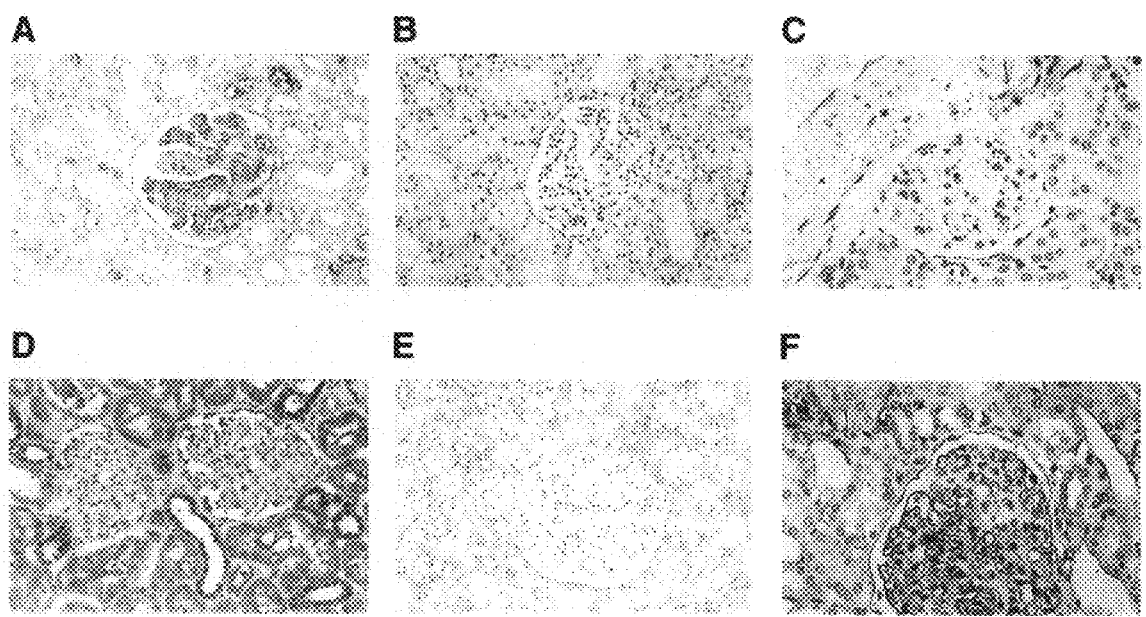
FIG. 14. GPBP is expressed in human but not in bovine and murine renal cortex. Cortex from human (A, D), bovine (B, E) or murine (C, F) kidney were paraffin embedded and probed with either GPBP-specific antibodies (A-C) or GPBP/GPBPΔ26-specific antibodies (D-F).

To further assess this hypothesis, we investigated the presence of GPBP and GPBPΔ26 in the glomerulus of two mammals that naturally do not undergo GP disease compared to human (FIG. 14). GPBP-specific antibodies failed to stain the glomerulus of both bovine or murine specimens (compare 14A with 14B and 14C) while antibodies recognizing the N-terminal sequence common to both GPBP and GPBPΔ26 stained these structures in all three species, although with different distributions and intensities (14D–14F). In bovine renal cortex, GPBPΔ26 was expressed at a lower rate than in human, but showed similar tissue distribution. In murine samples, however, GPBPΔ26 displayed a tissue distribution closely resembling that of GPBP in human glomerulus. Similar results were obtained when studying the alveolus in the three different species (not shown). To rule out that the differences in antibody detection was due to primary structure differences rather than to a differential expression, we determined the corresponding primary structures in these two species by cDNA sequencing. Bovine and mouse GPBP (SEQ ID NOS:3–6 and 9–12) displayed an overall identity with human material of 97.9% and 96.6% respectively. Furthermore, the mouse 26-residue motif was identical to human while bovine diverged only in one residue. Finally, and similarly to human, we successfully amplified GPBP cDNA from mouse or bovine kidney total RNA using oligonucleotides specific for the corresponding 78-bp exons, indicating that GPBP is expressed at very low levels not detectable by immunochemical techniques.

GPBP is Highly Expressed in Several Autoimmune Conditions

We analyzed several tissues from different GP patients by specific RT-PCR to assess GPBP/GPBPΔ26 mRNA levels. As in control kidneys, the major expressed isoform in GP kidneys was GPBPΔ26. However, in the muscle of one of the patients, GPBP was preferentially expressed, whereas GPBPΔ26 was the only isoform detected in control muscle samples (FIG. 15A). Since we did not have kidney samples from this particular patient, we could not assess GPBP/GPBPΔ26 expression in the corresponding target organ. For similar reasons, we could not assess GPBP/GPBPΔ26 levels in the muscle of the patients in which kidneys were studied. Muscle cells express high levels of GPBP/GPBPΔ26 (see Northern blot in FIG. 9), and they comprise the bulk of the tissue. In contrast, the expression of GPBP/GPBPΔ26 in the kidney was much less, and the glomerulus was virtually the only kidney structure expressing the GPBP isoform (see FIG. 13). The glomerulus is a relatively less abundant structure in kidney than the myocyte is in muscle, and the glomerulus is the structure targeted by immune attack in GP pathogenesis. These factors, together with the preferential amplification of the more abundant and shorter messages when performing RT-PCR studies, could account for the lack of detection of GPBP in both normal and GP kidneys, thus precluding the assessment of GPBP expression at the glomerulus during pathogenesis. Nevertheless, the increased levels of GPBP in a GP patient suggest that GPBP/GPBPΔ26 expression is altered during GP pathogenesis, and that augmented GPBP expression has a pathogenic significance in GP disease.

Figure 15:
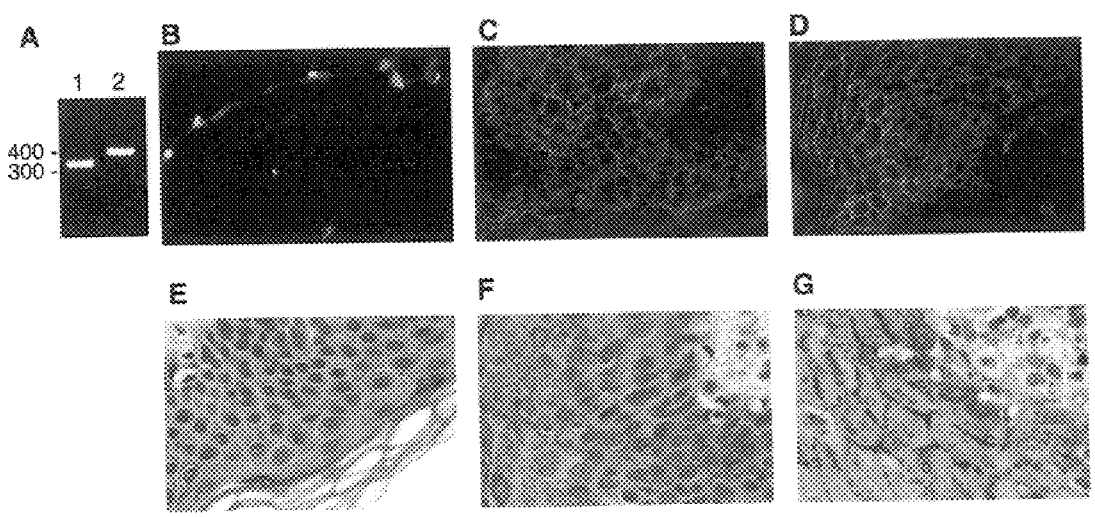
FIG. 15. GPBP is highly expressed in several autoimmune conditions. Skeletal muscle total RNA from a control individual (lane 1) or from a GP patient (lane 2) was subjected to RT-PCR as in FIG. 8, using the oligonucleotides 15m and 62c in the amplification program. Frozen (B-D) or paraffin embedded (E-G) human control skin (B, E) or skin affected by SLE (C, F) or lichen planus (D, G) were probed with GPBP-specific antibodies.

To investigate the expression of GPBP and GPBPΔ26 in autoimmune pathogenesis, we studied cutaneous autoimmune processes and compared them with control samples representing normal skin or non-autoimmune dermatitis (FIG. 15). Control samples displayed a limited expression of GPBP in the most peripheral keratinocytes (15B, 15E), while keratinocytes expanding from stratum basale to corneum expressed abundant GPBP in skin affected by systemic lupus erythematosus (SLE) (15C, 15F) or lichen planus (15D, 15G). GPBP was preferentially expressed in cell surface structures that closely resembled the blebs previously described in cultured keratinocytes upon UV irradiation and apoptosis induction (6). In contrast, antibodies recognizing both GPBP and GPBPΔ26 yielded a diffuse cytosolic pattern through the whole epidermis in both autoimmune affected or control samples (not shown). These data indicate that in both control and autoimmune-affected keratinocytes, GPBPΔ26 was expressed at the cytosol and that the expression did not significantly vary during cell differentiation. In contrast, mature keratinocytes were virtually the only GPBP expressing cells. However, bleb formation and expression of GPBP was observed in the early stages of differentiation in epidermis affected by autoimmune responses (15C, 15D, 15F, 15G). This further supports previous observations indicating that aberrant apoptosis at the basal keratinocytes is involved in the pathogenesis of autoimmune processes affecting skin (7), and suggests that apoptosis and GPBP expression are linked in this human cell system.

DISCUSSION

Alternative pre-mRNA splicing is a fundamental mechanism for differential gene expression that has been reported to regulate the tissue distribution, intracellular localization, and function of different protein kinases (8–11). In this regard, and closely resembling GPBP, B-Raf exists as multiple spliced variants, in which the presence of specific exons renders more interactive, efficient and oncogenic kinases (12).

Although it is evident that rGPBPΔ26 still bears the uncharacterized catalytic domain of this novel kinase, both auto- and trans-phosphorylating activities are greatly reduced when compared to rGPBP. Gel filtration and two hybrid experiments provide some insights into the mechanisms that underlie such a reduced phosphate transfer activity. About 1–2% of rGPBP is organized in very high molecular weight aggregates that display about one third of the phosphorylating activity of rGPBP, indicating that high molecular aggregation renders more efficient quaternary structures. Recombinant GPBPΔ26, with virtually no peak I material, consistently displayed a reduced kinase activity. However, aggregation does not seem to be the only mechanism by which the 26-residues increases specific activity, since the rGPBPΔ26 material present in peak II also shows a reduced phosphorylating activity when compared to homologous fractions of rGPBP. One possibility is that rGPBP-derived aggregates display higher specific activities because of quaternary structure strengthening caused by the insertion of the 26-residue motif. The oligomers are kept together mainly by very strong non-covalent bonds, since the bulk of the material appears as a single polypeptide in non-reducing SDS-PAGE, and the presence of either 8 M urea or 6 M guanidine had little effect on chromatographic gel filtration profiles (not shown). How the 26-residue motif renders a more strengthened and active structure remains to be clarified. Conformational changes induced by the presence of an exon encoded motif that alter the activation status of the kinase have been proposed for the linker domain of the Src protein (24) and exons 8b and 10 of B-Raf (12). Alternatively, the 26-residue motif may provide the structural requirements such as residues whose phosphorylation may be necessary for full activation of GPBP.

We have reported (13) that the primary structure of the GP antigen (α3(IV)NC1) is the target of a complex folding process yielding multiple conformers. Isolated conformers are non-minimum energy structures specifically activated by phosphorylation for supramolecular aggregation and likely quaternary structure formation. In GP patients, the α3(IV) NC1 shows conformational alterations and a reduced ability to mediate the disulfide stabilization of the collagen IV network. The GP antibodies, in turn, demonstrate stronger affinity towards the patient α3(IV)NC1 conformers, indicating that conformationally altered material caused the autoimmune response. Therefore, it seems that in GP disease an early alteration in the conforming process of the α3(IV) NC1 could generate altered conformers for which the immune system is not tolerant, thus mediating the autoimmune response.

Other evidence (Raya et al., unpublished results) indicates that phosphorylation is the signal that drives the folding of the α3(IV)NC1 into non-minimum energy ends. In this scenario, three features of the human α3(IV)NC1 system are of special pathogenic relevance when compared to the corresponding antigen systems from species that, like bovine or murine, do not undergo spontaneous GP disease. First, the N-terminus of the human α3(IV)NC1 contains a motif that is phosphorylatable by PKA and also by GPBP (see above, and also 2–4). Second, the human gene generates multiples alternative products by alternative exon splicing (14,15). Exon skipping generates alternative products with divergent C-terminal ends that up-regulate the in vitro PKA phosphorylation of the primary α3(IV)NC1 product (See below Example 3). Third, the human GPBP is expressed associated with glomerular and alveolar basement membranes, the two main targets in GP disease. The phosphorylation-dependent conforming process is also a feature of non-pathogenic NC1 domains (13), suggesting that the phosphorylatable N-terminus, the alternative splicing diversification, and the expression of GPBP at the glomerular and alveolar basement membranes, are all exclusively human features that place the conformation process of α3(IV)NC1 in a vulnerable condition. The four independent GP kidneys studied expressed higher levels of GP antigen alternative products (15; Bernal and Saus, unpublished results), and an augmented expression of GPBP were found in a GP patient (see above). Both increased levels of alternative GP antigen products and GPBP are expected to have consequences in the phosphorylation-dependent conformational process of the α3(IV)NC1, and therefore with pathogenic potential.

GPBP is highly expressed in skin targeted by natural autoimmune responses. In the epidermis, GPBP is associated with cell surface blebs characteristic of the apoptosis-mediated differentiation process that keratinocytes undergo during maturation from basale to corneum strata (22, 23). Keratinocytes from SLE patients show a remarkably heightened sensitivity to UV-induced apoptosis (6, 18, 20), and augmented and premature apoptosis of keratinocytes has been reported to exist in SLE and dermatomyositis (7). Consistently, we found apoptotic bodies expanding from basal to peripheral strata of the epidermis in several skin autoimmune conditions including discoid lupus (not shown), SLE and lichen planus. Autoantigens, and modified versions thereof are clustered in the cell surface blebs of apoptotic keratinocytes (6,18,20). Apoptotic surface blebs present autoantigens (21), and likely release modified versions to the circulation (16–20). It has been suggested that the release of modified autoantigens from apoptotic bodies could be the immunizing event that mediates systemic autoimmune responses mediating SLE and scleroderma (18,19).

Our evidence indicates that both GPBP and GPBPΔ26 are able to act in vitro as protein kinases, with GPBP being a more active isoform than GPBPΔ26. Furthermore, recombinant material representing GPBP or GPBPΔ26 purified from yeast or from human 293 cells contained an associated proteolytic activity that specifically degrades the α3(IV) NC1 domain (unpublished results). The proteolytic activity operates on α3(IV)NC1 produced in an eukaryotic expression system, but not on recombinant material produced in bacteria (unpublished results), indicating that α3(IV)NC1 processing has some conformational or post-translational requirements not present in prokaryotic recombinant material. Finally, it has been reported that several autoantigens undergo phosphorylation and degradation in apoptotic keratinocytes (20). While not being limited to an exact mechanism, we propose, in light of all of the above data, that the machinery assembling GPBP at the apoptotic blebs likely performs a complex modification of the autoantigens that includes phosphorylation, conformational changes and degradation. Accordingly, recombinant protein representing autoantigens in SLE (P1 ribosomal phosphoprotein and Sm-D1 small nuclear ribonucleoproteins) and in dermatomyositis (hystidil-tRNA synthetase) were in vitro substrates of GPBP (unpublished results).

The down-regulation in cancer cell lines of GPBP, suggest that the cell machinery harboring GPBP/GPBPΔ26 is likely involved in signaling pathways inducing programmed cell death. The corresponding apoptotic pathway could be up regulated during autoimmune pathogenesis to cause an altered antigen presentation in individuals carrying specific MHC haplotypes; and down regulated during cell transformation to prevent autoimmune attack to the transformed cells during tumor growth.

REFERENCES FOR EXAMPLE 2

1. Saus, J. (1998) in *Goodpasture's Syndrome: Encyclopedia of Immunology* $2^{nd}$ edn. Vol. 2, eds. Delves, P. J., & Roitt, I. M., (Academic Press Ltd., London),pp. 1005–1011.
2. Quinones, S., Bernal, D., García-Sogo, M., Elena S. F., & Saus, J. (1992) *J. Biol. Chem.* 267, 19780–19784.
3. Revert, F., Penadés, J. R., Plana, M., Bernal, D., Johansson, C., Itarte, E., Cervera, J., Wieslander, J., Quinones, S., & Saus, J.(1995) *J. Biol. Chem.* 270, 13254–13261.
4. Raya, A., Revert, F., Navarro, S., & Saus, J. (1999) *J. Biol. Chem.* 274, 12642–12649.
5. Green, M. R. (1986) *Ann. Rev. Genet.* 20, 671–708.
6. Casciola-Rosen, L. A., Anhalt, G. & Rosen, A. (1994) *J. Exp. Med.* 179:1317–1330.
7. Pablos, J. L:, Santiago, B., Galindo, M., Carreira, P. E., Ballestin, C.& Gomez-Reino, J. J. (1999) *J. Pathol.* 188: 63–68.
8. Srinivasan, M., Edman, C. F., & Schulman, H. (1994) *J. Cell. Biol.* 126, 839–852.
9. Naito, Y., Watanabe, Y., Yokokura, H., Sugita, R., Nishio, M., & Hidaka, H. (1997) *J. Biol. Chem.* 272, 32704–32708.
10. Bayer, K.-U., Löhler, J., & Harbers, K. (1996) *Mol. Cell. Biol.* 16, 29–36.
11. Madaule, P., Eda, M., Watanabe, N, Fujisawa, K., Matsuoka, T., Bito, H., Ishizaki, T., & Narumiya, S. (1998) *Nature* 394, 491–494.
12. Papin, C., Denouel-Galy, A., Laugier, D., Calothy, G., & Eychène, A. (1998) *J. Biol. Chem.* 273, 24939–24947.
13. U.S. Provisional Patent Application, Serial No. to be assigned, filed Feb. 11, 2000 (Case number 98,723-C)
14. Penadés, J. R., Bernal, D., Revert, F., Johansson, C., Fresquet, V. J., Cervera, J., Wieslander, J., Quinones, S. & Saus, J. (1995) *Eur. J. Biochem.* 229, 754–760.
15. Bernal, D., Quinones, S., & Saus, J. (1993) *J. Biol. Chem.,* 268, 12090–12094.
16. Casciola-Rosen, L. A., Anhalt, G. J.& Rosen, A.(1995) *J. Exp. Med.* 182: 1625–1634.
17. Casiano, C. A., Martin, S. J., Green, D. R., & Tan, E. M. (1996) *J Exp. Med.* 184: 765–770.
18. Casciola-Rosen, L., & Rosen, A. (1997) *Lupus* 6: 175–180.
19. Bolívar, J., Guelman, S., Iglesias, C., Ortíz, M., & Valdivia, M. (1998) *J. Biol. Chem.* 273: 17122–17127.
20. Utz, P. J., & Anderson, P. (1998) *Arthritis Rheum.* 41: 1152–1160.
21. Golan, T. D., Elkon, K. B., Ghavari, A. E., & Krueger, J. G. (1992) *J. Clin. Invest.* 90: 1067–1076.
22. Polalowska, R. R., Piacentini, M.,Bartlett, R., Goldsmith, L. A., & Haake, A. R. (1994) *Dev. Dinam.* 199: 176–188.
23. Maruoka, Y., Harada, H., Mitsuyasu et al. (1997) *Biochem. Biophys. Res. Commun.* 238: 886–890.
24. Xu, W., Harrison, S. C., & Eck, M. J. (1997) *Nature* 385, 595–602.

EXAMPLE 3

Regulation of Human Autoantigen Phosphorylation by Exon Splicing

INTRODUCTION

In GP disease, the immune system attack is mediated by autoantibodies against the non-collagenous C-terminal domain (NC1) of the α3 chain of collagen IV (the GP antigen) (1). The N-terminus of the human α3(IV)NC1 contains a highly divergent and hydrophilic region with a unique structural motif, KRGDS$^9$ (SEQ ID NO: 63), that harbors a cell adhesion signal as an integral part of a functional phosphorylation site for type A protein kinases (2,3). Furthermore, the gene region encoding the human GP antigen characteristically generates multiple mRNAs by alternative exon splicing (4,5). The alternative products diverge in the C-terminal ends and all but one share the N-terminal KRGDS$^9$ (SEQ ID NO: 63) (4,5).

Multiple sclerosis (MS) is an exclusive human neurological disease characterized by the presence of inflamatory demyelization plaques at the central nervous system. (6). Several evidences indicate that this disease is caused by an autoimmune attack mediated by cytotoxic T cells towards specific components of the white matter including the myelin basic protein (MBP) (7, 8). In humans, the MBP gene generates four products (MBP, MBPΔII, MBPΔV and MBPΔII/V) that result from alternative exon splicing during pre-mRNA processing (9). Among these, MBPΔII is the more abundant form in the mature central nervous system, while MBP form containing all the exons is virtually absent (9).

Several biological similarities exist between the autoimme responses mediating GP disease and MS, namely: 1) both are human exclusive diseases and typically initiate after a viral flu-like disease; 2) a strong linkage exists to the same haplotype of the HLA-DR region of the class II MHC; 3) several products are generated by alternative splicing; and 4) the death of a MS patient by GP disease has recently been reported (10).

MATERIALS AND METHODS

Synthetic Polymers

GPΔIII derived peptide, QRAHGQDLDALFVKVLRSP (SEQ ID NO:43) and GPΔIII/IV/V derived peptide, QRAH-GQDLESLFHQL (SEQ ID NO:44) were synthesized using either Boc- (MedProbe) or Fmoc- (Chiron, Lipotec) chemistry.

Plasmid Construction and Recombinant Expression
GP Derived Material

The constructs representing the different GP-spliced forms were obtained by subcloning the cDNAs used elsewhere to express the corresponding recombinant proteins (5) into the BamHI site of a modified pET15b vector, in which the extraneous vector-derived amino-terminal sequence except for the initiation Met was eliminated. The extra sequence was removed by cutting the vector with NcoI and Bam HI, filling-in of the free ends with Klenow, and re-ligation. This resulted in the reformation of both restriction sites and placed the BamHI site immediately downstream of the codon for the amino-terminal Met.

The recombinant proteins representing GP or GPΔV (SEQ ID NO:46) were purified by precipitation (5). Bacterial pellets containing the recombinant proteins representing GPΔIII (SEQ ID NO:48) or GPΔIII/IV/V (SEQ ID NO:50) were dissolved by 8 M urea in 40 mM Tris-HCl pH 6.8 and sonication. After centrifugation at 40,000×g the supernatants were passed through a 0.22 μm filter and applied to resource Q column for FPLC. The effluent was acidified to pH 6 with HCl and applied to a resource S column previously equilibrated with 40 mM MES pH 6 for a second FPLC purification. The material in the resulting effluent was used for in vitro phosphorylation. ps MBP-derived Material cDNA representing human MBPΔII (SEQ ID NO:51) was obtained by RT-PCR using total RNA from central nervous system. The cDNA representing human MBP was a generous gift from C. Campagnoni (UCLA). Both fragments were cloned into a modified version of pHIL-D2 (Invitrogen) containing a 6xHis-coding sequence at the C-terminus to generate pHIL-MBPΔII-His and pHIL-MBP-His, respectively. These plasmids were used for recombinant expression in *Pichia pastoris* as described in (12). Recombinant proteins were purified using immobilized metal affinity chromatography (TALON resin, CLONTECH) under denaturant conditions (8M urea) and eluted with 300 mM imidazole following manufacturers' instructions. The affinity-purified material was then renatured by dilution into 80 volumes of 50 mM Tris-HCl pH 8.0, 10 mM CHAPS, 400 mM NaCl, 2 mM DTT, and concentrated 50 times by ultrafiltration through a YM10-type membrane (AMICON). The Ser to Ala mutants were produced by site-directed mutagenesis over native sequence-containing constructs using transformer mutagenesis kit from CLONTECH and the resulting proteins were similarly produced.

Phosphorylation Studies

Phosphorylation studies were essentially done as described above (see also 3 and 12). In some experiments, the substrates were in-blot renatured and then, phosphorylated for 30 min at room temperature by overlaying 100 μl of phosphorylation buffer containing 0.5 μg of rGPBP. Digestion with V8 endopeptidase and immunoprecipitation were performed as described in (3).

Antibody Production

Synthetic peptides representing the C-terminal divergent ends of GPΔIII or GPΔIII/IV/V comprised in SEQ ID NO:43 or SEQ ID NO:44 respectively were conjugated to a cytochrome C, BSA or ovoalbumine using a glutaraldehyde coupling standard procedure. The resulting protein conjugates were used for mouse immmunization to obtain polyclonal antibodies specific for GPΔIII and monoclonal antibodies specific for GPΔIII/IV/V (Mab153). To obtain monoclonal antibodies specific for GPΔV (Mab5A) mouse were immunized using recombinant bacterial protein representing the corresponding alternative form comprising the SEQ ID NO:50. The production of monoclonal (M3/1, P1/2) or polyclonal (anti-GPpep1) antibodies against SEQ ID NO: 26 which represents the N-terminal region of the GP alternative forms have been previously described (3,5).

Boc-based Peptide Synthesis

Assembling

The peptide was assembled by stepwise solid phase synthesis using a Boc-Benzyl strategy. The starting resin used was Boc-Pro-PAM resin (0.56 meq/g, batch R4108). The deprotection /coupling procedure used was: TFA (1×1 min) TFA (1×3 min) DCM (flow flash) Isopropylalcohol (1×30 sec) DMF (3×1 min) COUPLING/DMF (1×10 min) DMF (1×1 min) COUPLING/DMF (1×10 min) DMF (2×1 min) DCM (1×1 min). For each step 10 ml per gram of peptide-resin were used. The coupling of all amino acids (fivefold excess) was performed in DMF in the presence of BOP, Hobt and DIEA. For the synthesis the following side-chain protecting groups were used: benzyl for serine; 2 chlorobenzyloxycarbonyl for lysine; cyclohexyl for aspartic and glutamic acid; tosyl for histidine and arginine.

Cleavage

The peptide was cleaved from the resin and fully deprotected by a treatment with liquid Hydrogen Fluoride (HF): Ten milliliters of HF per gram of peptide resin were added and the mixture kept at 0° C. for 45 min in the presence of p-cresol as scavengers. After evaporation of the HF, the crude reaction mixture is washed with ether, dissolved in TFA, precipitated with ether and dried.

Purification

Stationary phase: Silica C18, 15 µm, 120 A; Mobile phase: solvent A: water 0.1% TFA and solvent B: acetonitrile/A, 60/40 (v/v); Gradient: linear from 20 to 60% B in 30 min; Flow rate: 40 ml/min; and detection was U.V (210 nm). Fractions with a purity higher than 80% were pooled and lyophilized. Control of purity and identity was performed by analytical HPLC and ES/MS. The final product had 88% purity and an experimental molecular weight of 2192.9.

Fmoc-based Peptide Synthesis

Assembling

The peptides were synthesized by stepwise linear solid phase on Pro-clorotrityl-resin (0.685 meq/g) with standard Fmoc/tBu chemistry. The deprotection/coupling procedure used was: Fmoc aa (0.66 g) HOBt (0.26 g) DIPCDI (0.28 ml) for 40 min following a control by Kaiser test. If the test was positive the time was extended until change to negative. Then DMF (31 min), piperidine/DMF 20% (11 min) piperidine/DMF 20% (15 min) and DMF (41 min). Side chain protectors were: Pmc (pentamethylcromane sulfonyl) for arginine, Bcc (tert-butoxycarbonyl) for lysine, tBu (tert-butyl) for aspartic acid and for serine and Trl (trityl) for histidine.

Cleavage

The peptide was cleaved and fully deprotected by treatment cleavage with TFA/water 90/10. Ten milliliters of TFA solution per gram of resin were added. Water acts as scavenger. After two hours, resin was filtered and the resulting solution was precipitated five times with cold diethylether. The final precipitated was dried.

Purification

Stationary phase: Kromasil C18 10 µm; Mobile phase: solvent A: water 0.1% TFA and solvent B: acetonitrile 0.1% TFA; Isocratic: 28% B; Flow rate: 55 ml/min; Detection: 220 nm. Fractions with the higher purity were pooled and lyophilized, and a second HPLC purification round performed. Control of purity and identity was performed by analytical HPLC and ES/MS. The final product had 97% purity and an experimental molecular weight of 2190.9.

RESULTS

Figure 16:
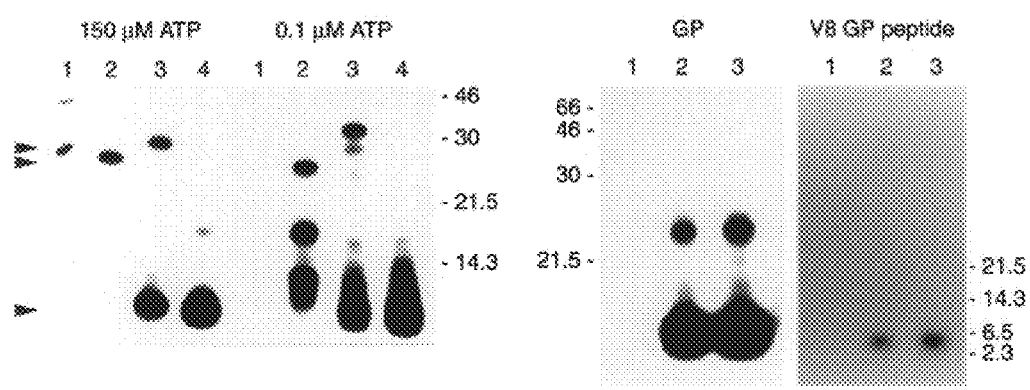
FIG. 16. Phosphorylation of GP alternative splicing products by PKA. In left panel, equimolecular amounts of rGP (lanes 1), rGPΔV (lanes 2), rGPΔIII (lanes 3) or rGPΔIII/IV/V (lanes 4), equivalent to 500 ng of the GP were phosphorylated at the indicated ATP concentrations. One-fifth of the total phosphorylation reaction mixture was separated by gel electrophoresis and transferred to PVDF, autoradiographed (shown) and the proteins blotted with M3/1, a specific monoclonal antibody recognizing all four species (shown) or using antibodies specific for each individual C-terminal region (not shown). Arrowheads indicate the position of each recombinant protein, from top to bottom, GP, GPΔV and, GPΔIII-GPΔIII/IV/V which displayed the same mobilities. Right panel: purified α3(IV) NC1 domain or hexamer was phosphorylated with PKA and 0.1 μM ATP in the absence (lanes 1) or in the presence of 10 nmol of peptides representing the C-terminal region of either GPΔIII (lanes 2) or GPΔIII/IV/V (lanes 3). Where indicated the phosphorylation mixtures of purified α3(IV)NC1 domain were V8 digested and immunoprecipitated with antibodies specific for the N terminus of the human α3(IV) NC1 domain (3). Bars and numbers indicate the position and sizes (kDa) of the molecular weight markers.

Regulation of the Phosphorylation of the Human GP Antigen by Alternative Splicing We produced bacterial recombinant proteins representing the primary antigen (GP) or the individual alternative products GPΔV (SEQ ID NO:46), GPΔIII (SEQ ID NO:48) and GPΔIII/IV/V (SEQ ID NO:50), and we tested their ability to be phosphorylated by PKA (FIG. 16, left panel ). Using standard ATP concentrations (150 µM), all four recombinant antigens were phosphorylated but to very different extents. The alternative forms incorporated $^{32}$P more efficiently than the primary GP antigen, suggesting that they are better substrates. Because these antigens are expected to be in the extracellular compartment, we also assayed their phosphorylatability with more physiological ATP concentrations (0.1–0.5 µM). Under these conditions, the differences in $^{32}$P incorporation between the primary and alternative products were more evident, indicating that at low ATP concentrations the primary GP antigen was a very poor substrate for the kinase. Among the three PKA phosphorylation sites present in the GP antigen, the N-terminal Ser$^9$ and Ser$^{26}$ are the major ones, and are common to all the alternative products assayed (3,5). Accordingly, the differences observed in phosphorylation for the full polypeptides also existed among the individual N-terminal regions, as determined after specific V8 digestion and immunoprecipitation (not shown). This strongly suggests that differences in phosphorylation might be due to the presence of different C-terminal sequences in the alternative products. Since GPΔIII and GPΔIII/IV/V displayed significantly higher $^{32}$P incorporation rates than GPΔV, and they have shorter divergent C-terminal regions (5), we used synthetic peptides individually representing these C-terminal sequences (SEQ ID NO: 43, SEQ ID NO:44) to further examine their regulatory roles in the in vitro phosphorylation of the native antigen. Collagen IV is a trimeric molecule comprised of three interwoven α chains. In basement membranes, two collagen IV molecules assemble through their NC1 domains to yield a hexameric NC1 structure that can be solubilized by bacterial collagenase digestion (1). Dissociation of the hexamer structure releases the GP antigen in monomeric and disulfide-related dimeric forms (1). For the following set of experiments, we carried out phosphorylations in the presence of low, extracellular-like ATP concentrations using both monomeric or hexameric native GP antigen (FIG. 16, right panel). The presence of each specific peptide but not control peptides (not shown) induced the phosphorylation of a single polypeptide displaying an apparent MW of 22 kDa. By specific V8 digestion and immunoprecipitation, the corresponding polypeptide has been identified as the 22 kDa conformer of the α3(IV)NC1, previously characterized and identified as the best substrate for the PKA (11).

Regulation of the Phosphorylation of the MBP by Alternative Splicing

Figure 18:
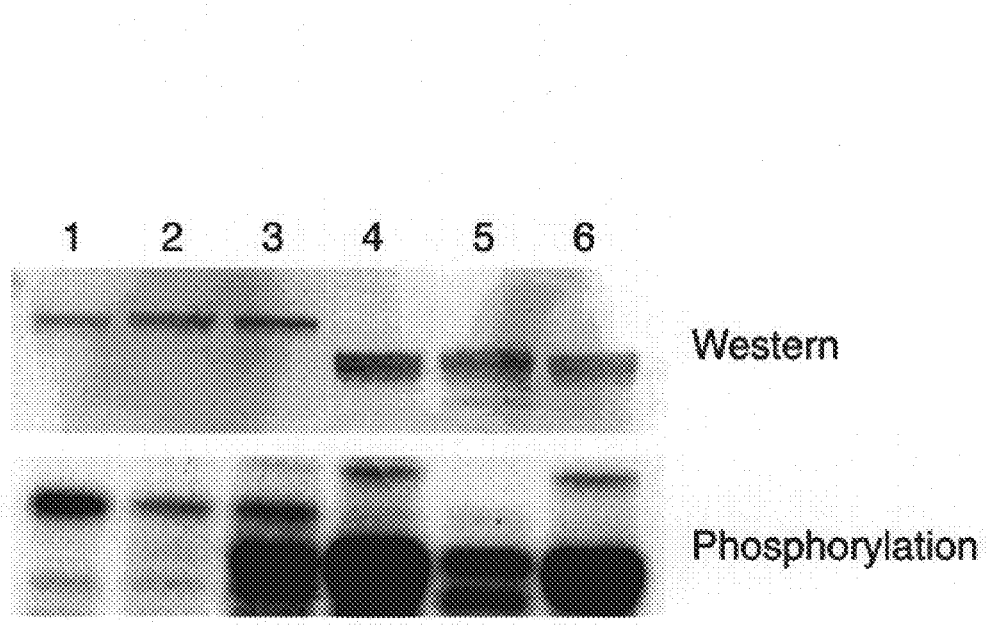
FIG. 18. Phosphorylation of recombinant MBP proteins by PKA. About 200 ng of rMBP (lane 1), or Ser to Ala mutants thereof in position 8 (lane 2) or 57 (lane 3), or rMPBΔII (lane 4) or Ser to Ala mutants thereof in position 8 (lane 5) or 57 (lane 6), were phosphorylated by PKA and 0.1 μM ATP. The mixtures were subjected to SDS-PAGE, transferred to PVDF and autoradiographed (Phosphorylation) and the individual molecular species blotted with monoclonal antibodies against human MBP obtained from Roche Molecular Biochemicals (Western).

The MBP contains at its N terminal region two PKA phosphorylation sites (Ser$^8$, Ser$^{57}$) that are structurally similar to the N terminus site (Ser$^9$) present in GP antigen products (FIG. 17). The Ser$^8$ site present in all the MBP proteins is located in a similar position than the Ser$^9$ in the GP-derived polypeptides. In addition, in the MBP and GPΔIII Ser$^8$ and Ser$^9$ respectively are at a similar distance in the primary structures of a highly homologous motif present in the corresponding exon II (bend arrow in FIG. 17). The GPΔIII-derived motif coincides with the C terminal divergent region that up-regulates PKA phosphorylation of Ser$^9$ in the GP antigen system (FIG. 16). The regulatory-like sequence in MBP is located at exon II and its presence in the final products depends on an alternative exon splicing mechanism. Therefore, the MBP motif identified by structural comparison to GPΔIII may be also regulating PKA phosphorylation of Ser$^8$. We produced recombinant proteins representing MBP and MBPΔII (SEQ ID NO:54) and the corresponding Ser to Ala mutants to knock-out each of the two PKA phosphorylation sites (Ser$^8$ and Ser$^{57}$) present in exon I. Subsequently, we assessed its in vitro phosphorylation by PKA (FIG. 18). MBPΔII was a better substrate than MBP, and Ser$^8$ was the major phosphorylation site, indicating that, similarly to GP antigenic system, alternative exon splicing regulates the PKA phosphorylation of specific sites located at the N-terminal region common to all the MBP-derived alternative forms.

Figure 19:
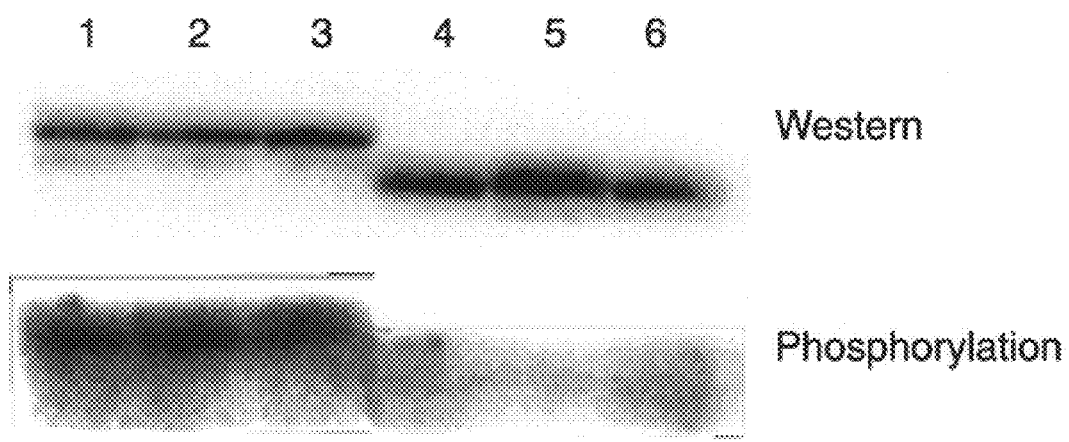
FIG. 19. Phosphorylation of recombinant MBP proteins by GPBP. About 200 ng of rMBP (lane 1), or Ser to Ala mutants thereof in positions 8 (lane 2) or 57 (lane 3), or rMPBΔII (lane 4), or Ser to Ala mutants thereof in positions 8 (lane 5) or 57 (lane 6), were subjected to SDS-PAGE, transferred to PVDF, and the area containing the proteins visualized with Ponceau and stripped out. The immobilized proteins were in situ phosphorylated with rGPBP as described in Materials and Methods, autoradiographed (Phosphorylation) and subsequently blotted as in FIG. 18 (Western).

In similar experiments assessing GPBP phosphorylation of the recombinant MBP proteins, GPBP preferentially phosphorylated MBP, while little phosphorylation of MBPΔII was observed (FIG. 19). Furthermore, recombinant Ser to Ala mutants displayed no significant reduction in $^{32}$P incorporation, indicating that GPBP phosphorylates MBP/MBPΔII in an opposite way than PKA, and that these two kinases do not share major phosphorylation sites in MBP proteins.

From all these data we concluded that in the MBP system, alternative splicing regulates the phosphorylation of specific serines by either PKA or GPBP.

Figure 20:
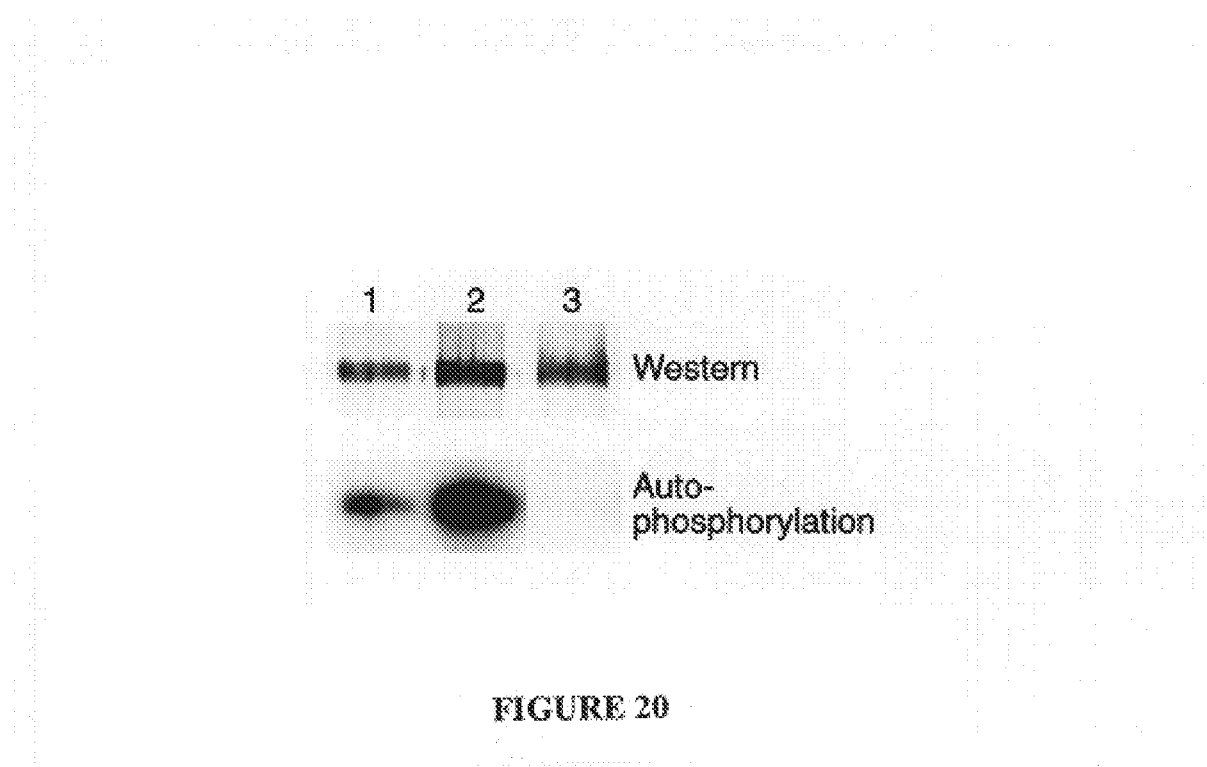
FIG. 20. Regulation of the GPBP by the C terminal region of GPΔIII. About 200 ng of rGPBP were in vitro phosphorylated with 150 μM ATP in the absence (lane 1) or in the presence of 5 nmol of GPΔIII-derived peptide synthesized either using Boc- (lane 2) or Fmoc-(lane 3) chemistry. The reaction mixtures were subjected to SDS-PAGE, transferred to PVDF and autoradiographed to asses autophosphorylation, and subsequently blotted with anti-FLAG monoclonal antibodies (Sigma) to determine the amount of recombinant material present (Western).

Synthetic Peptides Representing the C Terminal Region of GPΔIII Influence GPBP Phosphorylation To assess the effect of the C terminal region of GPΔIII on GPBP activity, peptides representing this region were synthesized using two different chemistries (Boc or Fmoc), and separately added to a phosphorylation mixture containing GPBP (FIG. 20). Boc-based synthetic peptides positively influenced GPBP autophosphorylation while Fmoc-based inhibited GPBP autophosphorylation, suggesting that the regulatory sequences derived from the alternative products in either GP and MBP antigenic systems can influence the kinase activity of GPBP.

DISCUSSION

We have shown that the α3(IV)NC1 domain undergoes a complex structural diversification by two different mechanism: 1) alternative splicing (4,5) and 2) conformational isomerization of the primary product (11). Both mechanisms generate products that are distinguished by PKA, indicating that PKA phosphorylation is a critical event in the biology of the α3(IV)NC1 domain. Phosphorylation guides at least in part the folding, but also the supramolecular assembly of the α3(IV)NC1 domain in the collagen IV network (11 and Raya et al. unpublished results). Altered conformers of the α3(IV)NC1 lead the autoimmune response mediating GP disease (11), suggesting that an alteration in antigen phosphorylation could be the primary event in the onset of the disease. Accordingly, we have found increased expression levels of GPΔIII in several GP kidneys (4 and Bernal and Saus, unpublished results), and an increased expression of GPBP has been detected in another Goodpasture patient (FIG. 15). Both increased expression of alternative GP antigen products and of GPBP are expected to have consequences in the phosphorylation steady state of α3(IV)NC1, and therefore in the corresponding conformational process. The discrimination among the different structural products by PKA strongly suggests that this kinase, or another structurally similar kinase, is involved in the physiological antigen conforming process, and that antigen phosphorylation by GPBP has a pathogenic significance. In pathogenesis, GPBP could be an intruding kinase, interfering in the phosphorylation-dependent conforming process. Accordingly, GPBP is expressed in tissue structures that are targeted by natural autoimmune responses, and an increased expression of GPBP is associated with several autoimmune conditions (See examples 1 and 2 above).

An alternative splicing mechanism also regulates the PKA phosphorylation of specific serines in the MBP antigenic system. MBP is also a substrate for GPBP suggesting that GPBP may play a pathogenic role in multiple sclerosis, and other autoimmune responses.

All of the above data identify GPBP as a potential target for therapeutics in autoimmune disease. In FIG. 20, we show that synthetic peptides representing the C terminal region of GPΔIII (SEQ ID NO:43) modulate the action of GPBP in vitro, and therefore we identified this and related sequences as peptide-based compounds to modulate the activity of GPBP in vivo. The induction of GP antigen phosphorylation by PKA was achieved when using Boc-based peptides, but not when using similar Fmoc-based peptides. Furthermore, Boc- but not Fmoc-based peptides were in vitro substrates of PKA (not shown), indicating that important structural differences exist between both products. Since both products displayed no significant differences in mass spectrometry, one possibility is that the different deprotection procedure used may be responsible for conformational differences in the secondary structure that may be critical for biological activity. Accordingly, Boc-based peptide loses its ability to induce PKA upon long storage at low temperatures. cl REFERENCES FOR EXAMPLE 3

1. Saus, J. (1998) in *Goodpasture's Syndrome: Encyclopedia of Immunology* 2$^{nd}$ edn. Vol. 2, eds. Delves, P. J., & Roitt, I. M., (Academic Press Ltd., London),pp. 1005–1011.
2. Quinones, S., Bernal, D., García-Sogo, M., Elena S. F., & Saus, J. (1992) *J. Biol. Chem.* 267, 19780–19784.
3. Revert, F., Penadés, J. R., Plana, M., Bernal, D., Johansson, C., Itarte, E., Cervera, J., Wieslander, J., Quinones, S., & Saus, J.(1995) *J. Biol. Chem.* 270, 13254–13261.
4. Bernal, D., Quinones, S., & Saus, J. (1993) *J. Biol. Chem.*, 268, 12090–12094.
5. Penadés, J. R., Bernal, D., Revert, F., Johansson, C., Fresquet, V. J., Cervera, J., Wieslander, J., Quinones, S. & Saus, J. (1995) *Eur. J. Biochem.* 229, 754–760.
6. Raus, J. C M, en *Multiple Sclerosis: Encyclopedia of Immunology* 2$^{nd}$ edn. Vol. 3 (eds. Delves, P. J., & Roitt, I. M.) 1786–1789 (Academic Press Ltd., London, 1998).
7. Pette, M., Fujita, K., Wilkinson, D., Altmann, D. M., Trowsdale, J., Giegerich, G., Hinkkanen, A., Epplen, J. T., Kappos, L., and Wekerle, H. (1994) *Proc. Natl. Acad. Sci. USA* 87, 7968–7972
8. Tschida, T., Parker, K. C., Turner, R. V., McFarland, H. F., Coligan, J. E., and Biddison, W. E.(1994) *Proc. Natl. Acad. Sci. USA* 91, 10859–10863.
9. Campagnoni, A. T. (1988) *J. Neurochem.* 51, 1–14.
10. Henderson, R. D., Saltissi, D., and Pender, M. P. (1998) *Acta Neurol. Scand.* 98, 134–135.
11. U.S. Provisional Patent Application, Serial No. to be assigned, filed Feb. 11, 2000 (Case number 98, 723-C).
12. Raya, A., Revert, F., Navarro, S., and Saus, J. (1999). *J. Biol. Chem.* 274,12642–12649.

The present invention is not limited by the aforementioned particular preferred embodiments. It will occur to those ordinarily skilled in the art that various modifications may be made to the disclosed preferred embodiments without diverting from the concept of the invention. All such modifications are intended to be within the scope of the present invention.

---

I claim:

1. A substantially purified polypeptide, comprising an amino acid sequence selected from the group consisting of SEQ ID NO:2 and SEQ ID NO:8.

2. The substantially purified polypeptide of claim 1, comprising the amino acid sequence of SEQ ID NO:2.

3. The substantially purified polypeptide of claim 1, comprising the amino acid sequence of SEQ ID NO:8.

4. A substantially purified polypeptide, consisting of an amino acid sequence selected from the group consisting of SEQ ID NO:2, SEQ ID NO:8, and SEQ ID NO:14.

5. The substantially purified polypeptide of claim 4, consisting of the amino acid sequence of SEQ ID NO:2.

6. The substantially purified polypeptide of claim 4, consisting of the amino acid sequence of SEQ ID NO:8.

7. The substantially purified polypeptide of claim 4, consisting of the amino acid sequence of SEQ ID NO:14.

8. The substantially purified polypeptide of any one of claim 1 or 2–7 wherein the substantially purified polypeptide is recombinantly expressed.

9. The substantially purified polypeptide of claim 8, wherein the substantially purified polypeptide is recombinantly expressed in mammalian cells.

10. The substantially purified polypeptide of claim 8, wherein the substantially purified polypeptide is recombinantly expressed in bacterial cells.

11. The substantially purified polypeptide of claim 8, wherein the substantially purified polypeptide is recombinantly expressed in yeast cells.

12. The substantially purified polypeptide of claim 8, wherein the substantially purified polypeptide is recombinantly expressed in *Pichia pastoris*.

13. The substantially purified polypeptide of any one of claim 1 or 2–7 wherein the substantially purified polypeptide is phosphorylated.

14. The substantially purified polypeptide of any one of claim 1 or 2–3 wherein the substantially purified polypeptide comprises oligomers of the substantially purified polypeptide.

15. An oligomer consisting of the substantially purified polypeptide of any one of claim 4–7.

* * * * *

SEQUENCE LISTING

<160> NUMBER OF SEQ ID NOS: 63

<210> SEQ ID NO 1
<211> LENGTH: 2389
<212> TYPE: DNA
<213> ORGANISM: Homo sapiens
<220> FEATURE:
<221> NAME/KEY: CDS
<222> LOCATION: (409)..(2280)

<400> SEQUENCE: 1
gcaggaagat ggcggcggta gcggaggtgt gagtggacgc gggactcagc ggccggattt    60

-continued

```
tctcttccct tcttttccct tttccttccc tatttgaaat tggcatcgag ggggctaagt      120
tcgggtggca gcgccgggcg caacgcaggg gtcacggcga cggcggcggc ggctgacggc      180
tggaagggta ggcttcattc accgctcgtc ctccttcctc gctccgctcg gtgtcaggcg      240
cggcggcggc gcggcgggcg gacttcgtcc ctcctcctgc tcccccccac accggagcgg      300
gcactcttcg cttcgccatc ccccgaccct tcaccccgag gactgggcgc ctcctccggc      360
gcagctgagg gagcggggc cggtctcctg ctcggttgtc gagcctcc atg tcg gat        417
                                                    Met Ser Asp
                                                     1 aat cag agc tgg aac tcg tcg ggc tcg gag gag gat cca gag acg gag        465
Asn Gln Ser Trp Asn Ser Ser Gly Ser Glu Glu Asp Pro Glu Thr Glu
 5                  10                  15 tct ggg ccg cct gtg gag cgc tgc ggg gtc ctc agt aag tgg aca aac        513
Ser Gly Pro Pro Val Glu Arg Cys Gly Val Leu Ser Lys Trp Thr Asn
 20                  25                  30                  35 tac att cat ggg tgg cag gat cgt tgg gta gtt ttg aaa aat aat gct        561
Tyr Ile His Gly Trp Gln Asp Arg Trp Val Val Leu Lys Asn Asn Ala
             40                  45                  50 ctg agt tac tac aaa tct gaa gat gaa aca gag tat ggc tgc aga gga        609
Leu Ser Tyr Tyr Lys Ser Glu Asp Glu Thr Glu Tyr Gly Cys Arg Gly
         55                  60                  65 tcc atc tgt ctt agc aag gct gtc atc aca cct cac gat ttt gat gaa        657
Ser Ile Cys Leu Ser Lys Ala Val Ile Thr Pro His Asp Phe Asp Glu
     70                  75                  80 tgt cga ttt gat att agt gta aat gat agt gtt tgg tat ctt cgt gct        705
Cys Arg Phe Asp Ile Ser Val Asn Asp Ser Val Trp Tyr Leu Arg Ala
 85                  90                  95 cag gat cca gat cat aga cag caa tgg ata gat gcc att gaa cag cac        753
Gln Asp Pro Asp His Arg Gln Gln Trp Ile Asp Ala Ile Glu Gln His
100                 105                 110                 115 aag act gaa tct gga tat gga tct gaa tcc agc ttg cgt cga cat ggc        801
Lys Thr Glu Ser Gly Tyr Gly Ser Glu Ser Ser Leu Arg Arg His Gly
                120                 125                 130 tca atg gtg tcc ctg gtg tct gga gca agt ggc tac tct gca aca tcc        849
Ser Met Val Ser Leu Val Ser Gly Ala Ser Gly Tyr Ser Ala Thr Ser
            135                 140                 145 acc tct tca ttc aag aaa ggc cac agt tta cgt gag aag ttg gct gaa        897
Thr Ser Ser Phe Lys Lys Gly His Ser Leu Arg Glu Lys Leu Ala Glu
        150                 155                 160 atg gaa aca ttt aga gac atc tta tgt aga caa gtt gac acg cta cag        945
Met Glu Thr Phe Arg Asp Ile Leu Cys Arg Gln Val Asp Thr Leu Gln
165                 170                 175 aag tac ttt gat gcc tgt gct gat gct gtc tct aag gat gaa ctt caa        993
Lys Tyr Phe Asp Ala Cys Ala Asp Ala Val Ser Lys Asp Glu Leu Gln
180                 185                 190                 195 agg gat aaa gtg gta gaa gat gat gaa gat gac ttt cct aca acg cgt       1041
Arg Asp Lys Val Val Glu Asp Asp Glu Asp Asp Phe Pro Thr Thr Arg
                200                 205                 210 tct gat ggt gac ttc ttg cat agt acc aac ggc aat aaa gaa aag tta       1089
Ser Asp Gly Asp Phe Leu His Ser Thr Asn Gly Asn Lys Glu Lys Leu
            215                 220                 225 ttt cca cat gtg aca cca aaa gga att aat ggt ata gac ttt aaa ggg       1137
Phe Pro His Val Thr Pro Lys Gly Ile Asn Gly Ile Asp Phe Lys Gly
        230                 235                 240 gaa gcg ata act ttt aaa gca act act gct gga atc ctt gca aca ctt       1185
Glu Ala Ile Thr Phe Lys Ala Thr Thr Ala Gly Ile Leu Ala Thr Leu
245                 250                 255
```

-continued

| | | |
|---|---|---|
| tct cat tgt att gaa cta atg gtt aaa cgt gag gac agc tgg cag aag<br>Ser His Cys Ile Glu Leu Met Val Lys Arg Glu Asp Ser Trp Gln Lys<br>260                265                270                275 | 1233 |
| aga ctg gat aag gaa act gag aag aaa aga aga aca gag gaa gca tat<br>Arg Leu Asp Lys Glu Thr Glu Lys Lys Arg Arg Thr Glu Glu Ala Tyr<br>                280                285                290 | 1281 |
| aaa aat gca atg aca gaa ctt aag aaa aaa tcc cac ttt gga gga cca<br>Lys Asn Ala Met Thr Glu Leu Lys Lys Lys Ser His Phe Gly Gly Pro<br>295                300                305 | 1329 |
| gat tat gaa gaa ggc cct aac agt ctg att aat gaa gaa gag ttc ttt<br>Asp Tyr Glu Glu Gly Pro Asn Ser Leu Ile Asn Glu Glu Glu Phe Phe<br>                310                315                320 | 1377 |
| gat gct gtt gaa gct gct ctt gac aga caa gat aaa ata gaa gaa cag<br>Asp Ala Val Glu Ala Ala Leu Asp Arg Gln Asp Lys Ile Glu Glu Gln<br>325                330                335 | 1425 |
| tca cag agt gaa aag gtg aga tta cat tgg cct aca tcc ttg ccc tct<br>Ser Gln Ser Glu Lys Val Arg Leu His Trp Pro Thr Ser Leu Pro Ser<br>340                345                350                355 | 1473 |
| gga gat gcc ttt tct tct gtg ggg aca cat aga ttt gtc caa aag ccc<br>Gly Asp Ala Phe Ser Ser Val Gly Thr His Arg Phe Val Gln Lys Pro<br>                360                365                370 | 1521 |
| tat agt cgc tct tcc tcc atg tct tcc att gat cta gtc agt gcc tct<br>Tyr Ser Arg Ser Ser Ser Met Ser Ser Ile Asp Leu Val Ser Ala Ser<br>375                380                385 | 1569 |
| gat gat gtt cac aga ttc agc tcc cag gtt gaa gag atg gtg cag aac<br>Asp Asp Val His Arg Phe Ser Ser Gln Val Glu Glu Met Val Gln Asn<br>                390                395                400 | 1617 |
| cac atg act tac tca tta cag gat gta ggc gga gat gcc aat tgg cag<br>His Met Thr Tyr Ser Leu Gln Asp Val Gly Gly Asp Ala Asn Trp Gln<br>405                410                415 | 1665 |
| ttg gtt gta gaa gaa gga gaa atg aag gta tac aga aga gaa gta gaa<br>Leu Val Val Glu Glu Gly Glu Met Lys Val Tyr Arg Arg Glu Val Glu<br>420                425                430                435 | 1713 |
| gaa aat ggg att gtt ctg gat cct tta aaa gct acc cat gca gtt aaa<br>Glu Asn Gly Ile Val Leu Asp Pro Leu Lys Ala Thr His Ala Val Lys<br>                440                445                450 | 1761 |
| ggc gtc aca gga cat gaa gtc tgc aat tat ttc tgg aat gtt gac gtt<br>Gly Val Thr Gly His Glu Val Cys Asn Tyr Phe Trp Asn Val Asp Val<br>455                460                465 | 1809 |
| cgc aat gac tgg gaa aca act ata gaa aac ttt cat gtg gtg gaa aca<br>Arg Asn Asp Trp Glu Thr Thr Ile Glu Asn Phe His Val Val Glu Thr<br>                470                475                480 | 1857 |
| tta gct gat aat gca atc atc att tat caa aca cac aag agg gtg tgg<br>Leu Ala Asp Asn Ala Ile Ile Ile Tyr Gln Thr His Lys Arg Val Trp<br>485                490                495 | 1905 |
| cct gct tct cag cga gac gta tta tat ctt tct gtc att cga aag ata<br>Pro Ala Ser Gln Arg Asp Val Leu Tyr Leu Ser Val Ile Arg Lys Ile<br>500                505                510                515 | 1953 |
| cca gcc ttg act gaa aat gac cct gaa act tgg ata gtt tgt aat ttt<br>Pro Ala Leu Thr Glu Asn Asp Pro Glu Thr Trp Ile Val Cys Asn Phe<br>                520                525                530 | 2001 |
| tct gtg gat cat gac agt gct cct cta aac aac cga tgt gtc cgt gcc<br>Ser Val Asp His Asp Ser Ala Pro Leu Asn Asn Arg Cys Val Arg Ala<br>535                540                545 | 2049 |
| aaa ata aat gtt gct atg att tgt caa acc ttg gta agc cca cca gag<br>Lys Ile Asn Val Ala Met Ile Cys Gln Thr Leu Val Ser Pro Pro Glu<br>                550                555                560 | 2097 |
| gga aac cag gaa att agc agg gac aac att cta tgc aag att aca tat<br>Gly Asn Gln Glu Ile Ser Arg Asp Asn Ile Leu Cys Lys Ile Thr Tyr<br>565                570                575 | 2145 |

```
gta gct aat gtg aac cct gga gga tgg gca cca gcc tca gtg tta agg      2193
Val Ala Asn Val Asn Pro Gly Gly Trp Ala Pro Ala Ser Val Leu Arg
580             585                 590                 595 gca gtg gca aag cga gag tat cct aaa ttt cta aaa cgt ttt act tct      2241
Ala Val Ala Lys Arg Glu Tyr Pro Lys Phe Leu Lys Arg Phe Thr Ser
                600                 605                 610 tac gtc caa gaa aaa act gca gga aag cct att ttg ttc tagtattaac       2290
Tyr Val Gln Glu Lys Thr Ala Gly Lys Pro Ile Leu Phe
            615                 620 aggtactaga agatatgttt tatcttttt taacttatt tgactaatat gactgtcaat      2350
actaaaattt agttgttgaa agtatttact atgtttttt                           2389

<210> SEQ ID NO 2
<211> LENGTH: 624
<212> TYPE: PRT
<213> ORGANISM: Homo sapiens

<400> SEQUENCE: 2

Met Ser Asp Asn Gln Ser Trp Asn Ser Ser Gly Ser Glu Glu Asp Pro
1               5                   10                  15

Glu Thr Glu Ser Gly Pro Pro Val Glu Arg Cys Gly Val Leu Ser Lys
                20                  25                  30

Trp Thr Asn Tyr Ile His Gly Trp Gln Asp Arg Trp Val Val Leu Lys
            35                  40                  45

Asn Asn Ala Leu Ser Tyr Tyr Lys Ser Glu Asp Glu Thr Glu Tyr Gly
        50                  55                  60

Cys Arg Gly Ser Ile Cys Leu Ser Lys Ala Val Ile Thr Pro His Asp
65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
                100                 105                 110

Glu Gln His Lys Thr Glu Ser Gly Tyr Gly Ser Glu Ser Ser Leu Arg
            115                 120                 125

Arg His Gly Ser Met Val Ser Leu Val Ser Gly Ala Ser Gly Tyr Ser
        130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Ala Cys Ala Asp Ala Val Ser Lys Asp
            180                 185                 190

Glu Leu Gln Arg Asp Lys Val Val Glu Asp Asp Glu Asp Asp Phe Pro
        195                 200                 205

Thr Thr Arg Ser Asp Gly Asp Phe Leu His Ser Thr Asn Gly Asn Lys
210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
            260                 265                 270

Trp Gln Lys Arg Leu Asp Lys Glu Thr Glu Lys Lys Arg Arg Thr Glu
        275                 280                 285
```

-continued

Glu Ala Tyr Lys Asn Ala Met Thr Glu Leu Lys Lys Lys Ser His Phe
      290                 295                 300

Gly Gly Pro Asp Tyr Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                    325                 330                 335

Glu Glu Gln Ser Gln Ser Glu Lys Val Arg Leu His Trp Pro Thr Ser
                340                 345                 350

Leu Pro Ser Gly Asp Ala Phe Ser Val Gly Thr His Arg Phe Val
            355                 360                 365

Gln Lys Pro Tyr Ser Arg Ser Ser Met Ser Ser Ile Asp Leu Val
        370                 375                 380

Ser Ala Ser Asp Asp Val His Arg Phe Ser Ser Gln Val Glu Glu Met
385                 390                 395                 400

Val Gln Asn His Met Thr Tyr Ser Leu Gln Asp Val Gly Gly Asp Ala
                405                 410                 415

Asn Trp Gln Leu Val Val Glu Glu Gly Glu Met Lys Val Tyr Arg Arg
            420                 425                 430

Glu Val Glu Glu Asn Gly Ile Val Leu Asp Pro Leu Lys Ala Thr His
        435                 440                 445

Ala Val Lys Gly Val Thr Gly His Glu Val Cys Asn Tyr Phe Trp Asn
        450                 455                 460

Val Asp Val Arg Asn Asp Trp Glu Thr Thr Ile Glu Asn Phe His Val
465                 470                 475                 480

Val Glu Thr Leu Ala Asp Asn Ala Ile Ile Ile Tyr Gln Thr His Lys
                485                 490                 495

Arg Val Trp Pro Ala Ser Gln Arg Asp Val Leu Tyr Leu Ser Val Ile
            500                 505                 510

Arg Lys Ile Pro Ala Leu Thr Glu Asn Asp Pro Glu Thr Trp Ile Val
        515                 520                 525

Cys Asn Phe Ser Val Asp His Asp Ser Ala Pro Leu Asn Asn Arg Cys
530                 535                 540

Val Arg Ala Lys Ile Asn Val Ala Met Ile Cys Gln Thr Leu Val Ser
545                 550                 555                 560

Pro Pro Glu Gly Asn Gln Glu Ile Ser Arg Asp Asn Ile Leu Cys Lys
                565                 570                 575

Ile Thr Tyr Val Ala Asn Val Asn Pro Gly Gly Trp Ala Pro Ala Ser
            580                 585                 590

Val Leu Arg Ala Val Ala Lys Arg Glu Tyr Pro Lys Phe Leu Lys Arg
        595                 600                 605

Phe Thr Ser Tyr Val Gln Glu Lys Thr Ala Gly Lys Pro Ile Leu Phe
        610                 615                 620

<210> SEQ ID NO 3
<211> LENGTH: 2762
<212> TYPE: DNA
<213> ORGANISM: Mus musculus
<220> FEATURE:
<221> NAME/KEY: CDS
<222> LOCATION: (444)..(2315)

<400> SEQUENCE: 3
cgggccacca cgtgtaaata gtatcggacc cggcaggaag atggcggctg tagcggaggt        60
gtgagtgagt ggatctgggt ctctgccgtt ggcttggctc ttcccgtctt cctcccctcc       120
tccctccctg actgaggttg gcatctaggg ggccgagttc aggtggcggc gccgggcgca       180

-continued

```
gcgcaggggt cacggccacg gcggctgacg gctggaaggg caggctttct tcgccgctcg      240
tcctccttcc ccggtccgct cggtgtcagg cgcggcggcg cgcggcgcggc gggcgcgctt      300 cgtccctctt cctgttccct cactcccggg agcgggctct cttggcggtg ccatccccg       360 accccttcacc ccagggacta ggcgcctgca ctggcgcagc tcgcggagcg ggggccggtc     420
tcctgctcgg ctgtcgcgtc tcc atg tcg gat aac cag agc tgg aac tcg tcg      473
                        Met Ser Asp Asn Gln Ser Trp Asn Ser Ser
                         1               5                  10 ggc tcg gag gag gat ccg gag acg gag tcc ggg ccg cct gtg gag cgc       521
Gly Ser Glu Glu Asp Pro Glu Thr Glu Ser Gly Pro Pro Val Glu Arg
                15                  20                  25 tgc ggg gtc ctc agc aag tgg aca aac tat att cat gga tgg cag gat       569
Cys Gly Val Leu Ser Lys Trp Thr Asn Tyr Ile His Gly Trp Gln Asp
            30                  35                  40 cgt tgg gta gtt ttg aaa aat aat act ttg agt tac tac aaa tct gaa       617
Arg Trp Val Val Leu Lys Asn Asn Thr Leu Ser Tyr Tyr Lys Ser Glu
        45                  50                  55 gat gaa aca gaa tat ggc tgt agg gga tcc atc tgt ctt agc aag gct       665
Asp Glu Thr Glu Tyr Gly Cys Arg Gly Ser Ile Cys Leu Ser Lys Ala
    60                  65                  70 gtg atc acg cct cac gat ttt gat gaa tgc cgg ttt gat atc agt gta       713
Val Ile Thr Pro His Asp Phe Asp Glu Cys Arg Phe Asp Ile Ser Val
75                  80                  85                  90 aat gat agt gtt tgg tac ctt cga gct cag gac ccg gag cac aga cag       761
Asn Asp Ser Val Trp Tyr Leu Arg Ala Gln Asp Pro Glu His Arg Gln
                95                  100                 105 caa tgg gta gac gcc att gaa cag cac aag act gaa tcg gga tat gga       809
Gln Trp Val Asp Ala Ile Glu Gln His Lys Thr Glu Ser Gly Tyr Gly
            110                 115                 120 tct gag tcc agc ttg cgt aga cat ggc tca atg gtg tca ctg gtg tct       857
Ser Glu Ser Ser Leu Arg Arg His Gly Ser Met Val Ser Leu Val Ser
        125                 130                 135 gga gcg agt ggc tat tct gct acg tcc acc tct tct ttc aag aaa ggc       905
Gly Ala Ser Gly Tyr Ser Ala Thr Ser Thr Ser Ser Phe Lys Lys Gly
    140                 145                 150 cac agt tta cgt gag aaa ctg gct gaa atg gag aca ttt cgg gac atc       953
His Ser Leu Arg Glu Lys Leu Ala Glu Met Glu Thr Phe Arg Asp Ile
155                 160                 165                 170 ctg tgc cgg cag gtt gat act ctc cag aag tac ttt gat gtc tgt gct      1001
Leu Cys Arg Gln Val Asp Thr Leu Gln Lys Tyr Phe Asp Val Cys Ala
                175                 180                 185 gac gct gtc tcc aag gat gag ctt cag agg gat aaa gtc gta gaa gat      1049
Asp Ala Val Ser Lys Asp Glu Leu Gln Arg Asp Lys Val Val Glu Asp
            190                 195                 200 gat gaa gat gac ttc cct aca act cgt tct gat gga gac ttt ttg cac      1097
Asp Glu Asp Asp Phe Pro Thr Thr Arg Ser Asp Gly Asp Phe Leu His
        205                 210                 215 aat acc aat ggt aat aaa gaa aaa tta ttt cca cat gta aca cca aaa      1145
Asn Thr Asn Gly Asn Lys Glu Lys Leu Phe Pro His Val Thr Pro Lys
    220                 225                 230 gga att aat ggc ata gac ttt aaa ggg gaa gca ata act ttt aaa gca      1193
Gly Ile Asn Gly Ile Asp Phe Lys Gly Glu Ala Ile Thr Phe Lys Ala
235                 240                 245                 250 act act gct gga atc ctt gct aca ctt tct cat tgt att gaa tta atg      1241
Thr Thr Ala Gly Ile Leu Ala Thr Leu Ser His Cys Ile Glu Leu Met
                255                 260                 265 gta aaa cgg gaa gag agc tgg caa aaa aga cac gat agg gaa gtg gaa      1289
Val Lys Arg Glu Glu Ser Trp Gln Lys Arg His Asp Arg Glu Val Glu
```

```
                       270                     275                     280
aag agg aga cga gtg gag gaa gcg tac aag aat gtg atg gaa gaa ctt         1337
Lys Arg Arg Arg Val Glu Glu Ala Tyr Lys Asn Val Met Glu Glu Leu
            285                     290                     295 aag aag aaa ccc cgt ttc gga ggg ccg gat tat gaa gaa ggt cca aac         1385
Lys Lys Lys Pro Arg Phe Gly Gly Pro Asp Tyr Glu Glu Gly Pro Asn
    300                     305                     310 agt ctg att aat gag gaa gag ttc ttt gat gct gtt gaa gct gct ctt         1433
Ser Leu Ile Asn Glu Glu Glu Phe Phe Asp Ala Val Glu Ala Ala Leu
315                     320                     325                 330 gac aga caa gat aaa ata gag gaa cag tca cag agt gaa aag gtc agg         1481
Asp Arg Gln Asp Lys Ile Glu Glu Gln Ser Gln Ser Glu Lys Val Arg
                335                     340                     345 tta cac tgg ccc aca tca ttg cca tct gga gac acc ttt tct tct gtc         1529
Leu His Trp Pro Thr Ser Leu Pro Ser Gly Asp Thr Phe Ser Ser Val
            350                     355                     360 ggg acg cat aga ttt gta caa aag ccc tat agt cgc tct tcc tcc atg         1577
Gly Thr His Arg Phe Val Gln Lys Pro Tyr Ser Arg Ser Ser Ser Met
        365                     370                     375 tct tcc att gat cta gtc agt gcc tct gac gat gtt cac aga ttc agc         1625
Ser Ser Ile Asp Leu Val Ser Ala Ser Asp Asp Val His Arg Phe Ser
380                     385                     390 tcc cag gtt gaa gaa atg gta cag aac cac atg aac tat tca tta cag         1673
Ser Gln Val Glu Glu Met Val Gln Asn His Met Asn Tyr Ser Leu Gln
395                     400                     405                 410 gat gta ggt ggt gat gca aat tgg caa ctg gtt gtt gaa gaa gga gaa         1721
Asp Val Gly Gly Asp Ala Asn Trp Gln Leu Val Val Glu Glu Gly Glu
                415                     420                     425 atg aag gta tac aga aga gaa gtg gaa gaa aat gga att gtt ctg gat         1769
Met Lys Val Tyr Arg Arg Glu Val Glu Glu Asn Gly Ile Val Leu Asp
            430                     435                     440 cct ttg aaa gct act cat gca gtt aaa ggt gtt aca gga cat gag gtc         1817
Pro Leu Lys Ala Thr His Ala Val Lys Gly Val Thr Gly His Glu Val
        445                     450                     455 tgc aat tac ttt tgg aat gtt gat gtt cgc aat gac tgg gaa act act         1865
Cys Asn Tyr Phe Trp Asn Val Asp Val Arg Asn Asp Trp Glu Thr Thr
    460                     465                     470 ata gaa aac ttt cat gtg gtg gaa aca tta gct gat aat gca atc atc         1913
Ile Glu Asn Phe His Val Val Glu Thr Leu Ala Asp Asn Ala Ile Ile
475                     480                     485                 490 gtt tat caa acg cac aag aga gta tgg ccc gct tct cag aga gac gta         1961
Val Tyr Gln Thr His Lys Arg Val Trp Pro Ala Ser Gln Arg Asp Val
                495                     500                     505 ctg tat ctt tct gct att cga aag atc cca gcc ttg act gaa aat gat         2009
Leu Tyr Leu Ser Ala Ile Arg Lys Ile Pro Ala Leu Thr Glu Asn Asp
            510                     515                     520 cct gaa act tgg ata gtt tgt aat ttt tct gtg gat cat gat agt gct         2057
Pro Glu Thr Trp Ile Val Cys Asn Phe Ser Val Asp His Asp Ser Ala
        525                     530                     535 cct ctg aac aat cga tgt gtc cgt gcc aaa atc aat att gct atg att         2105
Pro Leu Asn Asn Arg Cys Val Arg Ala Lys Ile Asn Ile Ala Met Ile
    540                     545                     550 tgt caa act tta gta agc cca cca gag gga gac cag gag ata agc aga         2153
Cys Gln Thr Leu Val Ser Pro Pro Glu Gly Asp Gln Glu Ile Ser Arg
555                     560                     565                 570 gac aac att ctg tgc aag atc acg tat gta gct aat gtg aac cca gga         2201
Asp Asn Ile Leu Cys Lys Ile Thr Tyr Val Ala Asn Val Asn Pro Gly
                575                     580                     585 gga tgg gcg cca gct tcg gtc tta aga gca gtg gca aag cga gaa tac         2249
```

```
Gly Trp Ala Pro Ala Ser Val Leu Arg Ala Val Ala Lys Arg Glu Tyr
                590                 595                 600 cct aag ttt cta aaa cgt ttt act tct tat gtc caa gaa aaa act gca      2297
Pro Lys Phe Leu Lys Arg Phe Thr Ser Tyr Val Gln Glu Lys Thr Ala
            605                 610                 615 gga aaa cca att ttg ttt tagtattaac agtgactgaa gcaaggctgc             2345
Gly Lys Pro Ile Leu Phe
        620 gtgacgttcc atgttggaga aggagggaa aaaataaaaa gaatcctcta agctggaacg     2405 taggatctac agccttgtct gtggcccaag aagaaacatt gcaatcgtaa agctgggtat    2465 ccagcactag ccatctcctg ctaggcctcc tcgctcagcg tgtaactata aatacatgta    2525 gaatcacatg gatatggcta tattttatt tgcttgctcc ttggagtgaa acaaataac      2585 tttgaattac aactaggaat taaccgatgc tttaattttg aggaactttt tcagaatttt    2645 ttatttacca tggtccaacc taagatcctc agttgtatca agttttgtg cacaaaagaa     2705 aagcacaaaa gttgaacgca cctgaaggca tgtgctctct gtgcaacaaa tactcag       2762

<210> SEQ ID NO 4
<211> LENGTH: 624
<212> TYPE: PRT
<213> ORGANISM: Mus musculus

<400> SEQUENCE: 4

Met Ser Asp Asn Gln Ser Trp Asn Ser Gly Ser Glu Glu Asp Pro
  1               5                  10                  15

Glu Thr Glu Ser Gly Pro Pro Val Glu Arg Cys Gly Val Leu Ser Lys
                20                  25                  30

Trp Thr Asn Tyr Ile His Gly Trp Gln Asp Arg Trp Val Val Leu Lys
            35                  40                  45

Asn Asn Thr Leu Ser Tyr Tyr Lys Ser Glu Asp Glu Thr Glu Tyr Gly
        50                  55                  60

Cys Arg Gly Ser Ile Cys Leu Ser Lys Ala Val Ile Thr Pro His Asp
 65                  70                  75                  80

Phe Asp Glu Cys Arg Phe Asp Ile Ser Val Asn Asp Ser Val Trp Tyr
                 85                  90                  95

Leu Arg Ala Gln Asp Pro Glu His Arg Gln Gln Trp Val Asp Ala Ile
                100                 105                 110

Glu Gln His Lys Thr Glu Ser Gly Tyr Gly Ser Glu Ser Ser Leu Arg
            115                 120                 125

Arg His Gly Ser Met Val Ser Leu Val Ser Gly Ala Ser Gly Tyr Ser
        130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Val Cys Ala Asp Ala Val Ser Lys Asp
            180                 185                 190

Glu Leu Gln Arg Asp Lys Val Val Glu Asp Asp Glu Asp Phe Pro
        195                 200                 205

Thr Thr Arg Ser Asp Gly Asp Phe Leu His Asn Thr Asn Gly Asn Lys
    210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
```

```
                   245                 250                  255
Ala Thr Leu Ser His Cys Ile Glu Leu Met Val Lys Arg Glu Glu Ser
                260                 265                 270

Trp Gln Lys Arg His Asp Arg Glu Val Glu Lys Arg Arg Val Glu
            275                 280                 285

Glu Ala Tyr Lys Asn Val Met Glu Glu Leu Lys Lys Pro Arg Phe
        290                 295                 300

Gly Gly Pro Asp Tyr Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Pro Thr Ser
            340                 345                 350

Leu Pro Ser Gly Asp Thr Phe Ser Ser Val Gly Thr His Arg Phe Val
        355                 360                 365

Gln Lys Pro Tyr Ser Arg Ser Ser Met Ser Ser Ile Asp Leu Val
    370                 375                 380

Ser Ala Ser Asp Asp Val His Arg Phe Ser Ser Gln Val Glu Glu Met
385                 390                 395                 400

Val Gln Asn His Met Asn Tyr Ser Leu Gln Asp Val Gly Gly Asp Ala
                405                 410                 415

Asn Trp Gln Leu Val Val Glu Glu Gly Glu Met Lys Val Tyr Arg Arg
            420                 425                 430

Glu Val Glu Glu Asn Gly Ile Val Leu Asp Pro Leu Lys Ala Thr His
        435                 440                 445

Ala Val Lys Gly Val Thr Gly His Glu Val Cys Asn Tyr Phe Trp Asn
    450                 455                 460

Val Asp Val Arg Asn Asp Trp Glu Thr Thr Ile Glu Asn Phe His Val
465                 470                 475                 480

Val Glu Thr Leu Ala Asp Asn Ala Ile Ile Val Tyr Gln Thr His Lys
                485                 490                 495

Arg Val Trp Pro Ala Ser Gln Arg Asp Val Leu Tyr Leu Ser Ala Ile
            500                 505                 510

Arg Lys Ile Pro Ala Leu Thr Glu Asn Asp Pro Glu Thr Trp Ile Val
        515                 520                 525

Cys Asn Phe Ser Val Asp His Asp Ser Ala Pro Leu Asn Asn Arg Cys
    530                 535                 540

Val Arg Ala Lys Ile Asn Ile Ala Met Ile Cys Gln Thr Leu Val Ser
545                 550                 555                 560

Pro Pro Glu Gly Asp Gln Glu Ile Ser Arg Asp Asn Ile Leu Cys Lys
                565                 570                 575

Ile Thr Tyr Val Ala Asn Val Asn Pro Gly Gly Trp Ala Pro Ala Ser
            580                 585                 590

Val Leu Arg Ala Val Ala Lys Arg Glu Tyr Pro Lys Phe Leu Lys Arg
        595                 600                 605

Phe Thr Ser Tyr Val Gln Glu Lys Thr Ala Gly Lys Pro Ile Leu Phe
    610                 615                 620

<210> SEQ ID NO 5
<211> LENGTH: 2361
<212> TYPE: DNA
<213> ORGANISM: Bos taurus
<220> FEATURE:
<221> NAME/KEY: CDS
<222> LOCATION: (421)..(2292)
```

-continued

```
<400> SEQUENCE: 5
cggcaggaag atggcggcct agcggaggtg tgagtggacc tgggtctctg cagctgggtt      60
ttccctcttc ccgtctttct cctcttttcc tctcccccga ggttggcatc gagggggcca     120
aattcgggcg gcggcgccgg gcgcagcgca ggggtcacaa cgacggcgac ggctgacggt     180
tggaagggca ggcttccttc gccctcgac ctccttcccc ggtccgcttg gtgtcaggcg      240
cggcggcggc ggcggcggcg gcgcggcggg cggactccat ccctcctccc gctccctcct     300
gcaccggagc gggcactcct tccttcgcca tcccccgacc cttcacccg gggactgggc      360 gcctccaccg gcgcagctca gggagcgggg gccggtctcc tgctcggctg tcgcgcctcc     420 atg tcg gat aac cag agc tgg aac tcg tcg ggc tcg gag gag gat ccg       468
Met Ser Asp Asn Gln Ser Trp Asn Ser Ser Gly Ser Glu Glu Asp Pro
  1               5                  10                  15 gag acg gag tcc ggg ccg ccg gtg gag cgc tgc gga gtc ctc aac aag       516
Glu Thr Glu Ser Gly Pro Pro Val Glu Arg Cys Gly Val Leu Asn Lys
             20                  25                  30 tgg aca aac tat att cat ggg tgg cag gat cgc tgg gta gtt ttg aaa       564
Trp Thr Asn Tyr Ile His Gly Trp Gln Asp Arg Trp Val Val Leu Lys
         35                  40                  45 aat aac act ctg agt tac tac aaa tct gaa gat gag aca gag tat ggc       612
Asn Asn Thr Leu Ser Tyr Tyr Lys Ser Glu Asp Glu Thr Glu Tyr Gly
     50                  55                  60 tgc aga gga tcc atc tgt ctt agc aag gct gtc atc acg cct cat gat       660
Cys Arg Gly Ser Ile Cys Leu Ser Lys Ala Val Ile Thr Pro His Asp
 65                  70                  75                  80 ttt gat gaa tgc cga ttt gat att agt gta aat gat agt gtt tgg tat       708
Phe Asp Glu Cys Arg Phe Asp Ile Ser Val Asn Asp Ser Val Trp Tyr
                 85                  90                  95 ctt cgt gct caa gat cca gat cac aga cag cag tgg ata gat gcc att       756
Leu Arg Ala Gln Asp Pro Asp His Arg Gln Gln Trp Ile Asp Ala Ile
            100                 105                 110 gaa cag cac aag act gaa tct gga tat gga tct gaa tcc agc ttg cgt       804
Glu Gln His Lys Thr Glu Ser Gly Tyr Gly Ser Glu Ser Ser Leu Arg
        115                 120                 125 cga cat ggc tcc atg gta tca ttg gta tcc gga gca agt ggc tat tct       852
Arg His Gly Ser Met Val Ser Leu Val Ser Gly Ala Ser Gly Tyr Ser
    130                 135                 140 gca aca tcc acc tcc tca ttc aag aag ggc cac agt tta cgt gag aaa       900
Ala Thr Ser Thr Ser Ser Phe Lys Lys Gly His Ser Leu Arg Glu Lys
145                 150                 155                 160 ctg gct gaa atg gaa acc ttt aga gat ata ctg tgt aga caa gtt gat       948
Leu Ala Glu Met Glu Thr Phe Arg Asp Ile Leu Cys Arg Gln Val Asp
                165                 170                 175 acc cta cag aag ttc ttt gat gcc tgt gct gat gct gtc tcc aag gat       996
Thr Leu Gln Lys Phe Phe Asp Ala Cys Ala Asp Ala Val Ser Lys Asp
            180                 185                 190 gaa ttt caa agg gat aaa gtg gta gaa gat gat gaa gat gac ttt cct      1044
Glu Phe Gln Arg Asp Lys Val Val Glu Asp Asp Glu Asp Asp Phe Pro
        195                 200                 205 acg aca cgt tct gat gga gac ttc ttg cat aat acc aat ggc aat aag      1092
Thr Thr Arg Ser Asp Gly Asp Phe Leu His Asn Thr Asn Gly Asn Lys
    210                 215                 220 gaa aag gta ttt cca cat gta aca cca aaa gga att aat ggt ata gac      1140
Glu Lys Val Phe Pro His Val Thr Pro Lys Gly Ile Asn Gly Ile Asp
225                 230                 235                 240 ttt aaa ggt gag gcg ata act ttt aaa gca act act gcc gga atc ctt      1188
Phe Lys Gly Glu Ala Ile Thr Phe Lys Ala Thr Thr Ala Gly Ile Leu
```

```
                    245                 250                 255
gct aca ctt tct cat tgt att gag ctg atg gta aaa cgt gag gac agc     1236
Ala Thr Leu Ser His Cys Ile Glu Leu Met Val Lys Arg Glu Asp Ser
            260                 265                 270 tgg caa aag aga atg gac aag gaa act gag aag aga aga gtg gag         1284
Trp Gln Lys Arg Met Asp Lys Glu Thr Glu Lys Arg Arg Val Glu
        275                 280                 285 gaa gca tac aaa aat gcc atg aca gaa ctt aag aaa aaa tcc cac ttt     1332
Glu Ala Tyr Lys Asn Ala Met Thr Glu Leu Lys Lys Lys Ser His Phe
        290                 295                 300 gga gga cca gat tat gag gaa ggc cca aac agt ttg att aat gaa gag     1380
Gly Gly Pro Asp Tyr Glu Glu Gly Pro Asn Ser Leu Ile Asn Glu Glu
305                 310                 315                 320 gag ttc ttt gat gct gtt gaa gct gct ctt gac aga caa gat aaa ata     1428
Glu Phe Phe Asp Ala Val Glu Ala Ala Leu Asp Arg Gln Asp Lys Ile
                325                 330                 335 gaa gaa cag tcg cag agt gaa aag gtc agg tta cat tgg tct act tca     1476
Glu Glu Gln Ser Gln Ser Glu Lys Val Arg Leu His Trp Ser Thr Ser
            340                 345                 350 atg cca tct gga gat gcc ttt tct tct gtg ggg act cat aga ttt gtc     1524
Met Pro Ser Gly Asp Ala Phe Ser Ser Val Gly Thr His Arg Phe Val
        355                 360                 365 caa aag ccc tat agt cgc tct tcc tcc atg tct tcc att gat cta gtc     1572
Gln Lys Pro Tyr Ser Arg Ser Ser Ser Met Ser Ser Ile Asp Leu Val
        370                 375                 380 agt gcc tct gac ggt gtt cac aga ttc agc tcc cag gtt gaa gag atg     1620
Ser Ala Ser Asp Gly Val His Arg Phe Ser Ser Gln Val Glu Glu Met
385                 390                 395                 400 gtg cag aac cac atg acc tat tca ttg cag gat gta ggt ggg gac gcc     1668
Val Gln Asn His Met Thr Tyr Ser Leu Gln Asp Val Gly Gly Asp Ala
                405                 410                 415 aac tgg cag ttg gtt gta gaa gaa ggg gag atg aag gta tat aga aga     1716
Asn Trp Gln Leu Val Val Glu Glu Gly Glu Met Lys Val Tyr Arg Arg
            420                 425                 430 gaa gta gaa gaa aat ggg att gtt ctg gat cct ttg aaa gct acc cat     1764
Glu Val Glu Glu Asn Gly Ile Val Leu Asp Pro Leu Lys Ala Thr His
        435                 440                 445 gca gtt aaa ggc gtt aca gga cac gag gtc tgc aat tac ttc tgg aat     1812
Ala Val Lys Gly Val Thr Gly His Glu Val Cys Asn Tyr Phe Trp Asn
        450                 455                 460 gtt gat gtt cgc aat gat tgg gaa aca act ata gaa aac ttt cat gtg     1860
Val Asp Val Arg Asn Asp Trp Glu Thr Thr Ile Glu Asn Phe His Val
465                 470                 475                 480 gtg gaa aca tta gct gat aat gca atc atc att tat caa acg cac aag     1908
Val Glu Thr Leu Ala Asp Asn Ala Ile Ile Ile Tyr Gln Thr His Lys
                485                 490                 495 aga gtg tgg cca gcc tct cag cgg gat gtc tta tat ctg tct gcc att     1956
Arg Val Trp Pro Ala Ser Gln Arg Asp Val Leu Tyr Leu Ser Ala Ile
            500                 505                 510 cga aag ata cca gct ttg aat gaa aat gac ccg gag act tgg ata gtt     2004
Arg Lys Ile Pro Ala Leu Asn Glu Asn Asp Pro Glu Thr Trp Ile Val
        515                 520                 525 tgt aat ttt tct gta gat cac agc agt gct cct cta aac aat cga tgt     2052
Cys Asn Phe Ser Val Asp His Ser Ser Ala Pro Leu Asn Asn Arg Cys
        530                 535                 540 gtc cgt gcc aaa ata aac gtt gct atg att tgt cag acc ttg gtg agc     2100
Val Arg Ala Lys Ile Asn Val Ala Met Ile Cys Gln Thr Leu Val Ser
545                 550                 555                 560 ccc cca gag gga aac cag gag att agc agg gac aac att cta tgc aag     2148
Pro Pro Glu Gly Asn Gln Glu Ile Ser Arg Asp Asn Ile Leu Cys Lys
```

```
Pro Pro Glu Gly Asn Gln Glu Ile Ser Arg Asp Asn Ile Leu Cys Lys
                565                 570                 575 att aca tac gtg gcc aat gta aac cct gga gga tgg gcc cca gcc tca    2196
Ile Thr Tyr Val Ala Asn Val Asn Pro Gly Gly Trp Ala Pro Ala Ser
                580                 585                 590 gtg tta cgg gca gtg gca aag cga gaa tat cca aag ttt cta aag cgt    2244
Val Leu Arg Ala Val Ala Lys Arg Glu Tyr Pro Lys Phe Leu Lys Arg
            595                 600                 605 ttt act tct tac gta caa gaa aaa act gca gga aaa cct att ttg ttc    2292
Phe Thr Ser Tyr Val Gln Glu Lys Thr Ala Gly Lys Pro Ile Leu Phe
        610                 615                 620 tagtattaac agtgactgaa gcaaggctgt gtgacattcc atgttggagg aaaaaaaaaa    2352
aaaaaaaaa                                                            2361

<210> SEQ ID NO 6
<211> LENGTH: 624
<212> TYPE: PRT
<213> ORGANISM: Bos taurus

<400> SEQUENCE: 6

Met Ser Asp Asn Gln Ser Trp Asn Ser Ser Gly Ser Glu Glu Asp Pro
 1               5                  10                  15

Glu Thr Glu Ser Gly Pro Pro Val Glu Arg Cys Gly Val Leu Asn Lys
             20                  25                  30

Trp Thr Asn Tyr Ile His Gly Trp Gln Asp Arg Trp Val Val Leu Lys
         35                  40                  45

Asn Asn Thr Leu Ser Tyr Tyr Lys Ser Glu Asp Glu Thr Glu Tyr Gly
     50                  55                  60

Cys Arg Gly Ser Ile Cys Leu Ser Lys Ala Val Ile Thr Pro His Asp
 65                  70                  75                  80

Phe Asp Glu Cys Arg Phe Asp Ile Ser Val Asn Asp Ser Val Trp Tyr
                 85                  90                  95

Leu Arg Ala Gln Asp Pro Asp His Arg Gln Gln Trp Ile Asp Ala Ile
            100                 105                 110

Glu Gln His Lys Thr Glu Ser Gly Tyr Gly Ser Glu Ser Ser Leu Arg
        115                 120                 125

Arg His Gly Ser Met Val Ser Leu Val Ser Gly Ala Ser Gly Tyr Ser
    130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Phe Phe Asp Ala Cys Ala Asp Ala Val Ser Lys Asp
            180                 185                 190

Glu Phe Gln Arg Asp Lys Val Val Glu Asp Asp Glu Asp Asp Phe Pro
        195                 200                 205

Thr Thr Arg Ser Asp Gly Asp Phe Leu His Asn Thr Asn Gly Asn Lys
    210                 215                 220

Glu Lys Val Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
            260                 265                 270

Trp Gln Lys Arg Met Asp Lys Glu Thr Glu Lys Arg Arg Arg Val Glu
```

-continued

```
                   275                 280                 285
Glu Ala Tyr Lys Asn Ala Met Thr Glu Leu Lys Lys Lys Ser His Phe
    290                 295                 300
Gly Gly Pro Asp Tyr Glu Gly Pro Asn Ser Leu Ile Asn Glu Glu
305                 310                 315                 320
Glu Phe Phe Asp Ala Val Glu Ala Leu Asp Arg Gln Asp Lys Ile
                325                 330                 335
Glu Glu Gln Ser Gln Ser Glu Lys Val Arg Leu His Trp Ser Thr Ser
                340                 345                 350
Met Pro Ser Gly Asp Ala Phe Ser Ser Val Gly Thr His Arg Phe Val
            355                 360                 365
Gln Lys Pro Tyr Ser Arg Ser Ser Met Ser Ile Asp Leu Val
    370                 375                 380
Ser Ala Ser Asp Gly Val His Arg Phe Ser Ser Gln Val Glu Glu Met
385                 390                 395                 400
Val Gln Asn His Met Thr Tyr Ser Leu Gln Asp Val Gly Gly Asp Ala
                405                 410                 415
Asn Trp Gln Leu Val Val Glu Glu Gly Glu Met Lys Val Tyr Arg Arg
            420                 425                 430
Glu Val Glu Glu Asn Gly Ile Val Leu Asp Pro Leu Lys Ala Thr His
                435                 440                 445
Ala Val Lys Gly Val Thr Gly His Glu Val Cys Asn Tyr Phe Trp Asn
450                 455                 460
Val Asp Val Arg Asn Asp Trp Glu Thr Thr Ile Glu Asn Phe His Val
465                 470                 475                 480
Val Glu Thr Leu Ala Asp Asn Ala Ile Ile Ile Tyr Gln Thr His Lys
                485                 490                 495
Arg Val Trp Pro Ala Ser Gln Arg Asp Val Leu Tyr Leu Ser Ala Ile
            500                 505                 510
Arg Lys Ile Pro Ala Leu Asn Glu Asn Asp Pro Glu Thr Trp Ile Val
            515                 520                 525
Cys Asn Phe Ser Val Asp His Ser Ser Ala Pro Leu Asn Asn Arg Cys
    530                 535                 540
Val Arg Ala Lys Ile Asn Val Ala Met Ile Cys Gln Thr Leu Val Ser
545                 550                 555                 560
Pro Pro Glu Gly Asn Gln Glu Ile Ser Arg Asp Asn Ile Leu Cys Lys
                565                 570                 575
Ile Thr Tyr Val Ala Asn Val Asn Pro Gly Gly Trp Ala Pro Ala Ser
                580                 585                 590
Val Leu Arg Ala Val Ala Lys Arg Glu Tyr Pro Lys Phe Leu Lys Arg
            595                 600                 605
Phe Thr Ser Tyr Val Gln Glu Lys Thr Ala Gly Lys Pro Ile Leu Phe
    610                 615                 620
```

<210> SEQ ID NO 7
<211> LENGTH: 2187
<212> TYPE: DNA
<213> ORGANISM: Artificial Sequence
<220> FEATURE:
<223> OTHER INFORMATION: Description of Artificial Sequence: Human GPBP26
<221> NAME/KEY: CDS
<222> LOCATION: (391)..(2184)

<400> SEQUENCE: 7
tagcggaggt gtgagtggac gcgggactca gcggccggat tttctcttcc cttctttcc     60

-continued

```
ctttctcctc cctatttgaa attggcatcg agggggctaa gttcgggtgg cagcgccggg      120
cgcaacgcag gggtcacggc gacggcggcg gcggctgacg gctggaaggg taggcttcat      180
tcaccgctcg tcctccttcc tcgctccgct cggtgtcagg cgcggcggcg gcgcggcggg      240
cggacttcgt ccctcctcct gctcccccc acaccggagc gggcactctt cgcttcgcca       300
tcccccgacc cttcaccccg aggactgggc gcctcctccg cgcagctga gggagcgggg       360 gccggtctcc tgctcggttg tcgagcctcc atg tcg gat aat cag agc tgg aac      414
                                  Met Ser Asp Asn Gln Ser Trp Asn
                                   1               5 tcg tcg ggc tcg gag gag gat cca gag acg gag tct ggg ccg cct gtg       462
Ser Ser Gly Ser Glu Glu Asp Pro Glu Thr Glu Ser Gly Pro Pro Val
    10              15                  20 gag cgc tgc ggg gtc ctc agt aag tgg aca aac tac att cat ggg tgg       510
Glu Arg Cys Gly Val Leu Ser Lys Trp Thr Asn Tyr Ile His Gly Trp
 25              30                  35                  40 cag gat cgt tgg gta gtt ttg aaa aat aat gct ctg agt tac tac aaa       558
Gln Asp Arg Trp Val Val Leu Lys Asn Asn Ala Leu Ser Tyr Tyr Lys
            45                  50                  55 tct gaa gat gaa aca gag tat ggc tgc aga gga tcc atc tgt ctt agc       606
Ser Glu Asp Glu Thr Glu Tyr Gly Cys Arg Gly Ser Ile Cys Leu Ser
60                  65                  70 aag gct gtc atc aca cct cac gat ttt gat gaa tgt cga ttt gat att       654
Lys Ala Val Ile Thr Pro His Asp Phe Asp Glu Cys Arg Phe Asp Ile
    75                  80                  85 agt gta aat gat agt gtt tgg tat ctt cgt gct cag gat cca gat cat       702
Ser Val Asn Asp Ser Val Trp Tyr Leu Arg Ala Gln Asp Pro Asp His
 90                  95                 100 aga cag caa tgg ata gat gcc att gaa cag cac aag act gaa tct gga       750
Arg Gln Gln Trp Ile Asp Ala Ile Glu Gln His Lys Thr Glu Ser Gly
105                 110                 115                 120 tat gga tct gaa tcc agc ttg cgt cga cat ggc tca atg gtg tcc ctg       798
Tyr Gly Ser Glu Ser Ser Leu Arg Arg His Gly Ser Met Val Ser Leu
                125                 130                 135 gtg tct gga gca agt ggc tac tct gca aca tcc acc tct tca ttc aag       846
Val Ser Gly Ala Ser Gly Tyr Ser Ala Thr Ser Thr Ser Ser Phe Lys
                140                 145                 150 aaa ggc cac agt tta cgt gag aag ttg gct gaa atg gaa aca ttt aga       894
Lys Gly His Ser Leu Arg Glu Lys Leu Ala Glu Met Glu Thr Phe Arg
                155                 160                 165 gac atc tta tgt aga caa gtt gac acg cta cag aag tac ttt gat gcc      942
Asp Ile Leu Cys Arg Gln Val Asp Thr Leu Gln Lys Tyr Phe Asp Ala
170                 175                 180 tgt gct gat gct gtc tct aag gat gaa ctt caa agg gat aaa gtg gta       990
Cys Ala Asp Ala Val Ser Lys Asp Glu Leu Gln Arg Asp Lys Val Val
185                 190                 195                 200 gaa gat gat gaa gat gac ttt cct aca acg cgt tct gat ggt gac ttc      1038
Glu Asp Asp Glu Asp Asp Phe Pro Thr Thr Arg Ser Asp Gly Asp Phe
                205                 210                 215 ttg cat agt acc aac ggc aat aaa gaa aag tta ttt cca cat gtg aca      1086
Leu His Ser Thr Asn Gly Asn Lys Glu Lys Leu Phe Pro His Val Thr
                220                 225                 230 cca aaa gga att aat ggt ata gac ttt aaa ggg gaa gcg ata act ttt      1134
Pro Lys Gly Ile Asn Gly Ile Asp Phe Lys Gly Glu Ala Ile Thr Phe
                235                 240                 245 aaa gca act act gct gga atc ctt gca aca ctt tct cat tgt att gaa      1182
Lys Ala Thr Thr Ala Gly Ile Leu Ala Thr Leu Ser His Cys Ile Glu
                250                 255                 260
```

-continued

| | |
|---|---|
| cta atg gtt aaa cgt gag gac agc tgg cag aag aga ctg gat aag gaa<br>Leu Met Val Lys Arg Glu Asp Ser Trp Gln Lys Arg Leu Asp Lys Glu<br>265                             270                     275                     280 | 1230 |
| act gag aag aaa aga aga aca gag gaa gca tat aaa aat gca atg aca<br>Thr Glu Lys Lys Arg Arg Thr Glu Glu Ala Tyr Lys Asn Ala Met Thr<br>285                     290                     295 | 1278 |
| gaa ctt aag aaa aaa tcc cac ttt gga gga cca gat tat gaa gaa ggc<br>Glu Leu Lys Lys Lys Ser His Phe Gly Gly Pro Asp Tyr Glu Glu Gly<br>300                     305                     310 | 1326 |
| cct aac agt ctg att aat gaa gaa gag ttc ttt gat gct gtt gaa gct<br>Pro Asn Ser Leu Ile Asn Glu Glu Glu Phe Phe Asp Ala Val Glu Ala<br>               315                     320                     325 | 1374 |
| gct ctt gac aga caa gat aaa ata gaa gaa cag tca cag agt gaa aag<br>Ala Leu Asp Arg Gln Asp Lys Ile Glu Glu Gln Ser Gln Ser Glu Lys<br>330                     335                     340 | 1422 |
| gtg aga tta cat tgg cct aca tcc ttg ccc tct gga gat gcc ttt tct<br>Val Arg Leu His Trp Pro Thr Ser Leu Pro Ser Gly Asp Ala Phe Ser<br>345                     350                     355                     360 | 1470 |
| tct gtg ggg aca cat aga ttt gtc caa aag gtt gaa gag atg gtg cag<br>Ser Val Gly Thr His Arg Phe Val Gln Lys Val Glu Glu Met Val Gln<br>               365                     370                     375 | 1518 |
| aac cac atg act tac tca tta cag gat gta ggc gga gat gcc aat tgg<br>Asn His Met Thr Tyr Ser Leu Gln Asp Val Gly Gly Asp Ala Asn Trp<br>380                     385                     390 | 1566 |
| cag ttg gtt gta gaa gaa gga gaa atg aag gta tac aga aga gaa gta<br>Gln Leu Val Val Glu Glu Gly Glu Met Lys Val Tyr Arg Arg Glu Val<br>395                     400                     405 | 1614 |
| gaa gaa aat ggg att gtt ctg gat cct tta aaa gct acc cat gca gtt<br>Glu Glu Asn Gly Ile Val Leu Asp Pro Leu Lys Ala Thr His Ala Val<br>410                     415                     420 | 1662 |
| aaa ggc gtc aca gga cat gaa gtc tgc aat tat ttc tgg aat gtt gac<br>Lys Gly Val Thr Gly His Glu Val Cys Asn Tyr Phe Trp Asn Val Asp<br>425                     430                     435                     440 | 1710 |
| gtt cgc aat gac tgg gaa aca act ata gaa aac ttt cat gtg gtg gaa<br>Val Arg Asn Asp Trp Glu Thr Thr Ile Glu Asn Phe His Val Val Glu<br>               445                     450                     455 | 1758 |
| aca tta gct gat aat gca atc atc att tat caa aca cac aag agg gtg<br>Thr Leu Ala Asp Asn Ala Ile Ile Ile Tyr Gln Thr His Lys Arg Val<br>460                     465                     470 | 1806 |
| tgg cct gct tct cag cga gac gta tta tat ctt tct gtc att cga aag<br>Trp Pro Ala Ser Gln Arg Asp Val Leu Tyr Leu Ser Val Ile Arg Lys<br>475                     480                     485 | 1854 |
| ata cca gcc ttg act gaa aat gac cct gaa act tgg ata gtt tgt aat<br>Ile Pro Ala Leu Thr Glu Asn Asp Pro Glu Thr Trp Ile Val Cys Asn<br>490                     495                     500 | 1902 |
| ttt tct gtg gat cat gac agt gct cct cta aac aac cga tgt gtc cgt<br>Phe Ser Val Asp His Asp Ser Ala Pro Leu Asn Asn Arg Cys Val Arg<br>505                     510                     515                     520 | 1950 |
| gcc aaa ata aat gtt gct atg att tgt caa acc ttg gta agc cca cca<br>Ala Lys Ile Asn Val Ala Met Ile Cys Gln Thr Leu Val Ser Pro Pro<br>               525                     530                     535 | 1998 |
| gag gga aac cag gaa att agc agg gac aac att cta tgc aag att aca<br>Glu Gly Asn Gln Glu Ile Ser Arg Asp Asn Ile Leu Cys Lys Ile Thr<br>540                     545                     550 | 2046 |
| tat gta gct aat gtg aac cct gga gga tgg gca cca gcc tca gtg tta<br>Tyr Val Ala Asn Val Asn Pro Gly Gly Trp Ala Pro Ala Ser Val Leu<br>555                     560                     565 | 2094 |
| agg gca gtg gca aag cga gag tat cct aaa ttt cta aaa cgt ttt act<br>Arg Ala Val Ala Lys Arg Glu Tyr Pro Lys Phe Leu Lys Arg Phe Thr<br>570                     575                     580 | 2142 |

```
                tct tac gtc caa gaa aaa act gca gga aag cct att ttg ttc tag    2187
                Ser Tyr Val Gln Glu Lys Thr Ala Gly Lys Pro Ile Leu Phe
                585                 590                 595
```

<210> SEQ ID NO 8
<211> LENGTH: 598
<212> TYPE: PRT
<213> ORGANISM: Artificial Sequence
<220> FEATURE:
<223> OTHER INFORMATION: Description of Artificial Sequence: Human
      GPBP26

<400> SEQUENCE: 8

```
Met Ser Asp Asn Gln Ser Trp Asn Ser Gly Ser Glu Glu Asp Pro
 1               5                  10                  15

Glu Thr Glu Ser Gly Pro Pro Val Glu Arg Cys Gly Val Leu Ser Lys
                20                  25                  30

Trp Thr Asn Tyr Ile His Gly Trp Gln Asp Arg Trp Val Leu Lys
             35                  40                  45

Asn Asn Ala Leu Ser Tyr Tyr Lys Ser Glu Asp Glu Thr Glu Tyr Gly
 50                  55                  60

Cys Arg Gly Ser Ile Cys Leu Ser Lys Ala Val Ile Thr Pro His Asp
 65                      70                  75                  80

Phe Asp Glu Cys Arg Phe Asp Ile Ser Val Asn Asp Ser Val Trp Tyr
                 85                  90                  95

Leu Arg Ala Gln Asp Pro Asp His Arg Gln Gln Trp Ile Asp Ala Ile
                100                 105                 110

Glu Gln His Lys Thr Glu Ser Gly Tyr Gly Ser Glu Ser Ser Leu Arg
            115                 120                 125

Arg His Gly Ser Met Val Ser Leu Val Ser Gly Ala Ser Gly Tyr Ser
130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Ala Cys Ala Asp Ala Val Ser Lys Asp
            180                 185                 190

Glu Leu Gln Arg Asp Lys Val Val Glu Asp Asp Glu Asp Phe Pro
        195                 200                 205

Thr Thr Arg Ser Asp Gly Asp Phe Leu His Ser Thr Asn Gly Asn Lys
            210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
                260                 265                 270

Trp Gln Lys Arg Leu Asp Lys Thr Glu Lys Lys Arg Arg Thr Glu
            275                 280                 285

Glu Ala Tyr Lys Asn Ala Met Thr Glu Leu Lys Lys Lys Ser His Phe
            290                 295                 300

Gly Gly Pro Asp Tyr Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335
```

```
Glu Glu Gln Ser Gln Ser Glu Lys Val Arg Leu His Trp Pro Thr Ser
            340                 345                 350
Leu Pro Ser Gly Asp Ala Phe Ser Ser Val Gly Thr His Arg Phe Val
            355                 360                 365
Gln Lys Val Glu Glu Met Val Gln Asn His Met Thr Tyr Ser Leu Gln
            370                 375                 380
Asp Val Gly Gly Asp Ala Asn Trp Gln Leu Val Val Glu Glu Gly Glu
385                 390                 395                 400
Met Lys Val Tyr Arg Arg Glu Val Glu Asn Gly Ile Val Leu Asp
                405                 410                 415
Pro Leu Lys Ala Thr His Ala Val Lys Gly Val Thr Gly His Glu Val
            420                 425                 430
Cys Asn Tyr Phe Trp Asn Val Asp Val Arg Asn Asp Trp Glu Thr Thr
            435                 440                 445
Ile Glu Asn Phe His Val Val Glu Thr Leu Ala Asp Asn Ala Ile Ile
            450                 455                 460
Ile Tyr Gln Thr His Lys Arg Val Trp Pro Ala Ser Gln Arg Asp Val
465                 470                 475                 480
Leu Tyr Leu Ser Val Ile Arg Lys Ile Pro Ala Leu Thr Glu Asn Asp
                485                 490                 495
Pro Glu Thr Trp Ile Val Cys Asn Phe Ser Val Asp His Asp Ser Ala
            500                 505                 510
Pro Leu Asn Asn Arg Cys Val Arg Ala Lys Ile Asn Val Ala Met Ile
            515                 520                 525
Cys Gln Thr Leu Val Ser Pro Pro Glu Gly Asn Gln Glu Ile Ser Arg
            530                 535                 540
Asp Asn Ile Leu Cys Lys Ile Thr Tyr Val Ala Asn Val Asn Pro Gly
545                 550                 555                 560
Gly Trp Ala Pro Ala Ser Val Leu Arg Ala Val Ala Lys Arg Glu Tyr
                565                 570                 575
Pro Lys Phe Leu Lys Arg Phe Thr Ser Tyr Val Gln Glu Lys Thr Ala
            580                 585                 590
Gly Lys Pro Ile Leu Phe
        595

<210> SEQ ID NO 9
<211> LENGTH: 2684
<212> TYPE: DNA
<213> ORGANISM: Artificial Sequence
<220> FEATURE:
<223> OTHER INFORMATION: Description of Artificial Sequence: Murine
      GPBP26
<221> NAME/KEY: CDS
<222> LOCATION: (444)..(2237)

<400> SEQUENCE: 9
cgggccacca cgtgtaaata gtatcggacc cggcaggaag atggcggctg tagcggaggt      60
gtgagtgagt ggatctgggt ctctgccgtt ggcttggctc ttccccgtctt cctcccctcc   120 tccctccctg actgaggttg gcatctaggg ggccgagttc aggtggcggc gccgggcgca   180
gcgcagggtc acggccacg gcggctgacg gctggaaggg caggcttct tcgccgctcg    240 tcctccttcc ccggtccgct cggtgtcagg gcgcggcggcg gcggcgcggc gggcgcgctt   300
cgtccctctt cctgttccct cactccccgg agcgggctct cttggcggtg ccatcccccg    360
acccttcacc ccagggacta ggcgcctgca ctggcgcagc tcgcggagcg ggggccggtc    420
tcctgctcgg ctgtcgcgtc tcc atg tcg gat aac cag agc tgg aac tcg tcg    473
```

```
                Met Ser Asp Asn Gln Ser Trp Asn Ser Ser
                 1               5                   10 ggc tcg gag gag gat ccg gag acg gag tcc ggg ccg cct gtg gag cgc       521
Gly Ser Glu Glu Asp Pro Glu Thr Glu Ser Gly Pro Pro Val Glu Arg
             15                  20                  25 tgc ggg gtc ctc agc aag tgg aca aac tat att cat gga tgg cag gat       569
Cys Gly Val Leu Ser Lys Trp Thr Asn Tyr Ile His Gly Trp Gln Asp
             30                  35                  40 cgt tgg gta gtt ttg aaa aat aat act ttg agt tac tac aaa tct gaa       617
Arg Trp Val Val Leu Lys Asn Asn Thr Leu Ser Tyr Tyr Lys Ser Glu
             45                  50                  55 gat gaa aca gaa tat ggc tgt agg gga tcc atc tgt ctt agc aag gct       665
Asp Glu Thr Glu Tyr Gly Cys Arg Gly Ser Ile Cys Leu Ser Lys Ala
    60                  65                  70 gtg atc acg cct cac gat ttt gat gaa tgc cgg ttt gat atc agt gta       713
Val Ile Thr Pro His Asp Phe Asp Glu Cys Arg Phe Asp Ile Ser Val
    75                  80                  85                  90 aat gat agt gtt tgg tac ctt cga gct cag gac ccg gag cac aga cag       761
Asn Asp Ser Val Trp Tyr Leu Arg Ala Gln Asp Pro Glu His Arg Gln
                 95                 100                 105 caa tgg gta gac gcc att gaa cag cac aag act gaa tcg gga tat gga       809
Gln Trp Val Asp Ala Ile Glu Gln His Lys Thr Glu Ser Gly Tyr Gly
                110                 115                 120 tct gag tcc agc ttg cgt aga cat ggc tca atg gtg tca ctg gtg tct       857
Ser Glu Ser Ser Leu Arg Arg His Gly Ser Met Val Ser Leu Val Ser
            125                 130                 135 gga gcg agt ggc tat tct gct acg tcc acc tct tct ttc aag aaa ggc       905
Gly Ala Ser Gly Tyr Ser Ala Thr Ser Thr Ser Ser Phe Lys Lys Gly
        140                 145                 150 cac agt tta cgt gag aaa ctg gct gaa atg gag aca ttt cgg gac atc       953
His Ser Leu Arg Glu Lys Leu Ala Glu Met Glu Thr Phe Arg Asp Ile
155                 160                 165                 170 ctg tgc cgg cag gtt gat act ctc cag aag tac ttt gat gtc tgt gct      1001
Leu Cys Arg Gln Val Asp Thr Leu Gln Lys Tyr Phe Asp Val Cys Ala
                175                 180                 185 gac gct gtc tcc aag gat gag ctt cag agg gat aaa gtc gta gaa gat      1049
Asp Ala Val Ser Lys Asp Glu Leu Gln Arg Asp Lys Val Val Glu Asp
            190                 195                 200 gat gaa gat gac ttc cct aca act cgt tct gat gga gac ttt ttg cac      1097
Asp Glu Asp Asp Phe Pro Thr Thr Arg Ser Asp Gly Asp Phe Leu His
        205                 210                 215 aat acc aat ggt aat aaa gaa aaa tta ttt cca cat gta aca cca aaa      1145
Asn Thr Asn Gly Asn Lys Glu Lys Leu Phe Pro His Val Thr Pro Lys
    220                 225                 230 gga att aat ggc ata gac ttt aaa ggg gaa gca ata act ttt aaa gca      1193
Gly Ile Asn Gly Ile Asp Phe Lys Gly Glu Ala Ile Thr Phe Lys Ala
235                 240                 245                 250 act act gct gga atc ctt gct aca ctt tct cat tgt att gaa tta atg      1241
Thr Thr Ala Gly Ile Leu Ala Thr Leu Ser His Cys Ile Glu Leu Met
                255                 260                 265 gta aaa cgg gaa gag agc tgg caa aaa aga cac gat agg gaa gtg gaa      1289
Val Lys Arg Glu Glu Ser Trp Gln Lys Arg His Asp Arg Glu Val Glu
            270                 275                 280 aag agg aga cga gtg gag gaa gcg tac aag aat gtg atg gaa gaa ctt      1337
Lys Arg Arg Arg Val Glu Glu Ala Tyr Lys Asn Val Met Glu Glu Leu
        285                 290                 295 aag aag aaa ccc cgt ttc gga ggg ccg gat tat gaa gaa ggt cca aac      1385
Lys Lys Lys Pro Arg Phe Gly Gly Pro Asp Tyr Glu Glu Gly Pro Asn
    300                 305                 310
```

-continued

```
agt ctg att aat gag gaa gag ttc ttt gat gct gtt gaa gct gct ctt    1433
Ser Leu Ile Asn Glu Glu Glu Phe Phe Asp Ala Val Glu Ala Ala Leu
315             320                 325                 330 gac aga caa gat aaa ata gag gaa cag tca cag agt gaa aag gtc agg    1481
Asp Arg Gln Asp Lys Ile Glu Glu Gln Ser Gln Ser Glu Lys Val Arg
            335                 340                 345 tta cac tgg ccc aca tca ttg cca tct gga gac acc ttt tct tct gtc    1529
Leu His Trp Pro Thr Ser Leu Pro Ser Gly Asp Thr Phe Ser Ser Val
        350                 355                 360 ggg acg cat aga ttt gta caa aag gtt gaa gaa atg gta cag aac cac    1577
Gly Thr His Arg Phe Val Gln Lys Val Glu Glu Met Val Gln Asn His
    365                 370                 375 atg aac tat tca tta cag gat gta ggt ggt gat gca aat tgg caa ctg    1625
Met Asn Tyr Ser Leu Gln Asp Val Gly Gly Asp Ala Asn Trp Gln Leu
380             385                 390 gtt gtt gaa gaa gga gaa atg aag gta tac aga aga gaa gtg gaa gaa    1673
Val Val Glu Glu Gly Glu Met Lys Val Tyr Arg Arg Glu Val Glu Glu
395             400                 405                 410 aat gga att gtt ctg gat cct ttg aaa gct act cat gca gtt aaa ggt    1721
Asn Gly Ile Val Leu Asp Pro Leu Lys Ala Thr His Ala Val Lys Gly
            415                 420                 425 gtt aca gga cat gag gtc tgc aat tac ttt tgg aat gtt gat gtt cgc    1769
Val Thr Gly His Glu Val Cys Asn Tyr Phe Trp Asn Val Asp Val Arg
        430                 435                 440 aat gac tgg gaa act act ata gaa aac ttt cat gtg gtg gaa aca tta    1817
Asn Asp Trp Glu Thr Thr Ile Glu Asn Phe His Val Val Glu Thr Leu
    445                 450                 455 gct gat aat gca atc atc gtt tat caa acg cac aag aga gta tgg ccc    1865
Ala Asp Asn Ala Ile Ile Val Tyr Gln Thr His Lys Arg Val Trp Pro
460             465                 470 gct tct cag aga gac gta ctg tat ctt tct gct att cga aag atc cca    1913
Ala Ser Gln Arg Asp Val Leu Tyr Leu Ser Ala Ile Arg Lys Ile Pro
475             480                 485                 490 gcc ttg act gaa aat gat cct gaa act tgg ata gtt tgt aat ttt tct    1961
Ala Leu Thr Glu Asn Asp Pro Glu Thr Trp Ile Val Cys Asn Phe Ser
            495                 500                 505 gtg gat cat gat agt gct cct ctg aac aat cga tgt gtc cgt gcc aaa    2009
Val Asp His Asp Ser Ala Pro Leu Asn Asn Arg Cys Val Arg Ala Lys
        510                 515                 520 atc aat att gct atg att tgt caa act tta gta agc cca cca gag gga    2057
Ile Asn Ile Ala Met Ile Cys Gln Thr Leu Val Ser Pro Pro Glu Gly
    525                 530                 535 gac cag gag ata agc aga gac aac att ctg tgc aag atc acg tat gta    2105
Asp Gln Glu Ile Ser Arg Asp Asn Ile Leu Cys Lys Ile Thr Tyr Val
540             545                 550 gct aat gtg aac cca gga gga tgg gcg cca gct tcg gtc tta aga gca    2153
Ala Asn Val Asn Pro Gly Gly Trp Ala Pro Ala Ser Val Leu Arg Ala
555             560                 565                 570 gtg gca aag cga gaa tac cct aag ttt cta aaa cgt ttt act tct tat    2201
Val Ala Lys Arg Glu Tyr Pro Lys Phe Leu Lys Arg Phe Thr Ser Tyr
            575                 580                 585 gtc caa gaa aaa act gca gga aaa cca att ttg ttt tagtattaac         2247
Val Gln Glu Lys Thr Ala Gly Lys Pro Ile Leu Phe
                590                 595 agtgactgaa gcaaggctgc gtgacgttcc atgttggaga aggagggaa aaaataaaaa    2307 gaatcctcta agctggaacg taggatctac agccttgtct gtgcccaag aagaaacatt    2367 gcaatcgtaa agctgggtat ccagcactag ccatctcctg ctaggcctcc tcgctcagcg   2427
tgtaactata aatacatgta gaatcacatg gatatggcta tattttatt tgcttgctcc    2487
```

```
ttggagtgaa acaaataac tttgaattac aactaggaat taaccgatgc tttaattttg    2547
aggaactttt tcagaatttt ttatttacca tggtccaacc taagatcctc agttgtatca    2607
agtttttgtg cacaaaagaa aagcacaaaa gttgaacgca cctgaaggca tgtgctctct    2667
gtgcaacaaa tactcag                                                   2684
```

<210> SEQ ID NO 10
<211> LENGTH: 598
<212> TYPE: PRT
<213> ORGANISM: Artificial Sequence
<220> FEATURE:
<223> OTHER INFORMATION: Description of Artificial Sequence: Murine GPBP26

<400> SEQUENCE: 10

```
Met Ser Asp Asn Gln Ser Trp Asn Ser Gly Ser Glu Glu Asp Pro
 1               5                  10                  15

Glu Thr Glu Ser Gly Pro Pro Val Glu Arg Cys Gly Val Leu Ser Lys
                20                  25                  30

Trp Thr Asn Tyr Ile His Gly Trp Gln Asp Arg Trp Val Val Leu Lys
            35                  40                  45

Asn Asn Thr Leu Ser Tyr Tyr Lys Ser Glu Asp Glu Thr Glu Tyr Gly
        50                  55                  60

Cys Arg Gly Ser Ile Cys Leu Ser Lys Ala Val Ile Thr Pro His Asp
 65                  70                  75                  80

Phe Asp Glu Cys Arg Phe Asp Ile Ser Val Asn Asp Ser Val Trp Tyr
                85                  90                  95

Leu Arg Ala Gln Asp Pro Glu His Arg Gln Gln Trp Val Asp Ala Ile
            100                 105                 110

Glu Gln His Lys Thr Glu Ser Gly Tyr Gly Ser Glu Ser Ser Leu Arg
        115                 120                 125

Arg His Gly Ser Met Val Ser Leu Val Ser Gly Ala Ser Gly Tyr Ser
130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Val Cys Ala Asp Ala Val Ser Lys Asp
            180                 185                 190

Glu Leu Gln Arg Asp Lys Val Val Glu Asp Asp Glu Asp Phe Pro
        195                 200                 205

Thr Thr Arg Ser Asp Gly Asp Phe Leu His Asn Thr Asn Gly Asn Lys
        210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Glu Ser
            260                 265                 270

Trp Gln Lys Arg His Asp Arg Glu Val Glu Lys Arg Arg Arg Val Glu
        275                 280                 285

Glu Ala Tyr Lys Asn Val Met Glu Glu Leu Lys Lys Lys Pro Arg Phe
        290                 295                 300

Gly Gly Pro Asp Tyr Glu Gly Pro Asn Ser Leu Ile Asn Glu Glu
305                 310                 315                 320
```

```
Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Pro Thr Ser
            340                 345                 350

Leu Pro Ser Gly Asp Thr Phe Ser Ser Val Gly Thr His Arg Phe Val
        355                 360                 365

Gln Lys Val Glu Glu Met Val Gln Asn His Met Asn Tyr Ser Leu Gln
    370                 375                 380

Asp Val Gly Gly Asp Ala Asn Trp Gln Leu Val Val Glu Glu Gly Glu
385                 390                 395                 400

Met Lys Val Tyr Arg Arg Glu Val Glu Asn Gly Ile Val Leu Asp
                405                 410                 415

Pro Leu Lys Ala Thr His Ala Val Lys Gly Val Thr Gly His Glu Val
                420                 425                 430

Cys Asn Tyr Phe Trp Asn Val Asp Val Arg Asn Asp Trp Glu Thr Thr
                435                 440                 445

Ile Glu Asn Phe His Val Val Glu Thr Leu Ala Asp Asn Ala Ile Ile
            450                 455                 460

Val Tyr Gln Thr His Lys Arg Val Trp Pro Ala Ser Gln Arg Asp Val
465                 470                 475                 480

Leu Tyr Leu Ser Ala Ile Arg Lys Ile Pro Ala Leu Thr Glu Asn Asp
                485                 490                 495

Pro Glu Thr Trp Ile Val Cys Asn Phe Ser Val Asp His Asp Ser Ala
            500                 505                 510

Pro Leu Asn Asn Arg Cys Val Arg Ala Lys Ile Asn Ile Ala Met Ile
        515                 520                 525

Cys Gln Thr Leu Val Ser Pro Pro Glu Gly Asp Gln Glu Ile Ser Arg
    530                 535                 540

Asp Asn Ile Leu Cys Lys Ile Thr Tyr Val Ala Asn Val Asn Pro Gly
545                 550                 555                 560

Gly Trp Ala Pro Ala Ser Val Leu Arg Ala Val Ala Lys Arg Glu Tyr
                565                 570                 575

Pro Lys Phe Leu Lys Arg Phe Thr Ser Tyr Val Gln Glu Lys Thr Ala
                580                 585                 590

Gly Lys Pro Ile Leu Phe
        595

<210> SEQ ID NO 11
<211> LENGTH: 2283
<212> TYPE: DNA
<213> ORGANISM: Artificial Sequence
<220> FEATURE:
<223> OTHER INFORMATION: Description of Artificial Sequence: Bovine
      GPBP26
<221> NAME/KEY: CDS
<222> LOCATION: (421)..(2214)

<400> SEQUENCE: 11
cggcaggaag atggcggcct agcggaggtg tgagtggacc tgggtctctg cagctgggtt      60
ttccctcttc ccgtctttct cctctttttcc tctcccccga ggttggcatc gaggggggcca    120 aattcgggcg gcggcgccgg gcgcagcgca ggggtcacaa cgacggcgac ggctgacggt    180
tggaagggca ggcttccttc gcccctcgac ctccttcccc ggtccgcttg gtgtcaggcg      240
cggcggcggc ggcggcggcg gcgcggcggg cggactccat ccctcctccc gctccctcct    300
gcaccggagc gggcactcct tcctccgcca tcccccgacc cttcaccccg gggactgggc    360
```

```
                                                             -continued gcctccaccg gcgcagctca gggagcgggg gccggtctcc tgctcggctg tcgcgcctcc     420 atg tcg gat aac cag agc tgg aac tcg tcg ggc tcg gag gag gat ccg       468
Met Ser Asp Asn Gln Ser Trp Asn Ser Ser Gly Ser Glu Glu Asp Pro
1               5                   10                  15 gag acg gag tcc ggg ccg ccg gtg gag cgc tgc gga gtc ctc aac aag       516
Glu Thr Glu Ser Gly Pro Pro Val Glu Arg Cys Gly Val Leu Asn Lys
                20                  25                  30 tgg aca aac tat att cat ggg tgg cag gat cgc tgg gta gtt ttg aaa       564
Trp Thr Asn Tyr Ile His Gly Trp Gln Asp Arg Trp Val Val Leu Lys
            35                  40                  45 aat aac act ctg agt tac tac aaa tct gaa gat gag aca gag tat ggc       612
Asn Asn Thr Leu Ser Tyr Tyr Lys Ser Glu Asp Glu Thr Glu Tyr Gly
    50                  55                  60 tgc aga gga tcc atc tgt ctt agc aag gct gtc atc acg cct cat gat       660
Cys Arg Gly Ser Ile Cys Leu Ser Lys Ala Val Ile Thr Pro His Asp
65                  70                  75                  80 ttt gat gaa tgc cga ttt gat att agt gta aat gat agt gtt tgg tat       708
Phe Asp Glu Cys Arg Phe Asp Ile Ser Val Asn Asp Ser Val Trp Tyr
                85                  90                  95 ctt cgt gct caa gat cca gat cac aga cag cag tgg ata gat gcc att       756
Leu Arg Ala Gln Asp Pro Asp His Arg Gln Gln Trp Ile Asp Ala Ile
                100                 105                 110 gaa cag cac aag act gaa tct gga tat gga tct gaa tcc agc ttg cgt       804
Glu Gln His Lys Thr Glu Ser Gly Tyr Gly Ser Glu Ser Ser Leu Arg
            115                 120                 125 cga cat ggc tcc atg gta tca ttg gta tcc gga gca agt ggc tat tct       852
Arg His Gly Ser Met Val Ser Leu Val Ser Gly Ala Ser Gly Tyr Ser
        130                 135                 140 gca aca tcc acc tcc tca ttc aag aag ggc cac agt tta cgt gag aaa       900
Ala Thr Ser Thr Ser Ser Phe Lys Lys Gly His Ser Leu Arg Glu Lys
145                 150                 155                 160 ctg gct gaa atg gaa acc ttt aga gat ata ctg tgt aga caa gtt gat       948
Leu Ala Glu Met Glu Thr Phe Arg Asp Ile Leu Cys Arg Gln Val Asp
                165                 170                 175 acc cta cag aag ttc ttt gat gcc tgt gct gat gct gtc tcc aag gat       996
Thr Leu Gln Lys Phe Phe Asp Ala Cys Ala Asp Ala Val Ser Lys Asp
            180                 185                 190 gaa ttt caa agg gat aaa gtg gta gaa gat gat gaa gat gac ttt cct      1044
Glu Phe Gln Arg Asp Lys Val Val Glu Asp Asp Glu Asp Asp Phe Pro
        195                 200                 205 acg aca cgt tct gat gga gac ttc ttg cat aat acc aat ggc aat aag      1092
Thr Thr Arg Ser Asp Gly Asp Phe Leu His Asn Thr Asn Gly Asn Lys
    210                 215                 220 gaa aag gta ttt cca cat gta aca cca aaa gga att aat ggt ata gac      1140
Glu Lys Val Phe Pro His Val Thr Pro Lys Gly Ile Asn Gly Ile Asp
225                 230                 235                 240 ttt aaa ggt gag gcg ata act ttt aaa gca act act gcc gga atc ctt      1188
Phe Lys Gly Glu Ala Ile Thr Phe Lys Ala Thr Thr Ala Gly Ile Leu
                245                 250                 255 gct aca ctt tct cat tgt att gag ctg atg gta aaa cgt gag gac agc      1236
Ala Thr Leu Ser His Cys Ile Glu Leu Met Val Lys Arg Glu Asp Ser
            260                 265                 270 tgg caa aag aga atg gac aag gaa act gag aag aga aga gtg gag         1284
Trp Gln Lys Arg Met Asp Lys Glu Thr Glu Lys Arg Arg Val Glu
        275                 280                 285 gaa gca tac aaa aat gcc atg aca gaa ctt aag aaa aaa tcc cac ttt      1332
Glu Ala Tyr Lys Asn Ala Met Thr Glu Leu Lys Lys Lys Ser His Phe
        290                 295                 300
```

```
gga gga cca gat tat gag gaa ggc cca aac agt ttg att aat gaa gag      1380
Gly Gly Pro Asp Tyr Glu Glu Gly Pro Asn Ser Leu Ile Asn Glu Glu
305                 310                 315                 320 gag ttc ttt gat gct gtt gaa gct gct ctt gac aga caa gat aaa ata      1428
Glu Phe Phe Asp Ala Val Glu Ala Ala Leu Asp Arg Gln Asp Lys Ile
                325                 330                 335 gaa gaa cag tcg cag agt gaa aag gtc agg tta cat tgg tct act tca      1476
Glu Glu Gln Ser Gln Ser Glu Lys Val Arg Leu His Trp Ser Thr Ser
            340                 345                 350 atg cca tct gga gat gcc ttt tct tct gtg ggg act cat aga ttt gtc      1524
Met Pro Ser Gly Asp Ala Phe Ser Ser Val Gly Thr His Arg Phe Val
        355                 360                 365 caa aag gtt gaa gag atg gtg cag aac cac atg acc tat tca ttg cag      1572
Gln Lys Val Glu Glu Met Val Gln Asn His Met Thr Tyr Ser Leu Gln
    370                 375                 380 gat gta ggt ggg gac gcc aac tgg cag ttg gtt gta gaa gaa ggg gag      1620
Asp Val Gly Gly Asp Ala Asn Trp Gln Leu Val Val Glu Glu Gly Glu
385                 390                 395                 400 atg aag gta tat aga aga gaa gta gaa gaa aat ggg att gtt ctg gat      1668
Met Lys Val Tyr Arg Arg Glu Val Glu Glu Asn Gly Ile Val Leu Asp
                405                 410                 415 cct ttg aaa gct acc cat gca gtt aaa ggc gtt aca gga cac gag gtc      1716
Pro Leu Lys Ala Thr His Ala Val Lys Gly Val Thr Gly His Glu Val
            420                 425                 430 tgc aat tac ttc tgg aat gtt gat gtt cgc aat gat tgg gaa aca act      1764
Cys Asn Tyr Phe Trp Asn Val Asp Val Arg Asn Asp Trp Glu Thr Thr
        435                 440                 445 ata gaa aac ttt cat gtg gtg gaa aca tta gct gat aat gca atc atc      1812
Ile Glu Asn Phe His Val Val Glu Thr Leu Ala Asp Asn Ala Ile Ile
450                 455                 460 att tat caa acg cac aag aga gtg tgg cca gcc tct cag cgg gat gtc      1860
Ile Tyr Gln Thr His Lys Arg Val Trp Pro Ala Ser Gln Arg Asp Val
465                 470                 475                 480 tta tat ctg tct gcc att cga aag ata cca gct ttg aat gaa aat gac      1908
Leu Tyr Leu Ser Ala Ile Arg Lys Ile Pro Ala Leu Asn Glu Asn Asp
                485                 490                 495 ccg gag act tgg ata gtt tgt aat ttt tct gta gat cac agc agt gct      1956
Pro Glu Thr Trp Ile Val Cys Asn Phe Ser Val Asp His Ser Ser Ala
            500                 505                 510 cct cta aac aat cga tgt gtc cgt gcc aaa ata aac gtt gct atg att      2004
Pro Leu Asn Asn Arg Cys Val Arg Ala Lys Ile Asn Val Ala Met Ile
        515                 520                 525 tgt cag acc ttg gtg agc ccc cca gag gga aac cag gag att agc agg      2052
Cys Gln Thr Leu Val Ser Pro Pro Glu Gly Asn Gln Glu Ile Ser Arg
    530                 535                 540 gac aac att cta tgc aag att aca tac gtg gcc aat gta aac cct gga      2100
Asp Asn Ile Leu Cys Lys Ile Thr Tyr Val Ala Asn Val Asn Pro Gly
545                 550                 555                 560 gga tgg gcc cca gcc tca gtg tta cgg gca gtg gca aag cga gaa tat      2148
Gly Trp Ala Pro Ala Ser Val Leu Arg Ala Val Ala Lys Arg Glu Tyr
                565                 570                 575 cca aag ttt cta aag cgt ttt act tct tac gta caa gaa aaa act gca      2196
Pro Lys Phe Leu Lys Arg Phe Thr Ser Tyr Val Gln Glu Lys Thr Ala
            580                 585                 590 gga aaa cct att ttg ttc tagtattaac agtgactgaa gcaaggctgt             2244
Gly Lys Pro Ile Leu Phe
        595 gtgacattcc atgttggagg aaaaaaaaaa aaaaaaaa                            2283
```

```
<210> SEQ ID NO 12
<211> LENGTH: 598
<212> TYPE: PRT
<213> ORGANISM: Artificial Sequence
<220> FEATURE:
<223> OTHER INFORMATION: Description of Artificial Sequence: Bovine
      GPBP26

<400> SEQUENCE: 12

Met Ser Asp Asn Gln Ser Trp Asn Ser Ser Gly Ser Glu Glu Asp Pro
 1               5                  10                  15

Glu Thr Glu Ser Gly Pro Pro Val Glu Arg Cys Gly Val Leu Asn Lys
            20                  25                  30

Trp Thr Asn Tyr Ile His Gly Trp Gln Asp Arg Trp Val Val Leu Lys
        35                  40                  45

Asn Asn Thr Leu Ser Tyr Tyr Lys Ser Glu Asp Glu Thr Glu Tyr Gly
 50                  55                  60

Cys Arg Gly Ser Ile Cys Leu Ser Lys Ala Val Ile Thr Pro His Asp
 65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
            100                 105                 110

Glu Gln His Lys Thr Glu Ser Gly Tyr Gly Ser Glu Ser Ser Leu Arg
        115                 120                 125

Arg His Gly Ser Met Val Ser Leu Val Ser Gly Ala Ser Gly Tyr Ser
130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Phe Phe Asp Ala Cys Ala Asp Ala Val Ser Lys Asp
            180                 185                 190

Glu Phe Gln Arg Asp Lys Val Val Glu Asp Asp Glu Asp Phe Pro
        195                 200                 205

Thr Thr Arg Ser Asp Gly Asp Phe Leu His Asn Thr Asn Gly Asn Lys
    210                 215                 220

Glu Lys Val Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
            260                 265                 270

Trp Gln Lys Arg Met Asp Lys Glu Thr Glu Lys Arg Arg Val Glu
        275                 280                 285

Glu Ala Tyr Lys Asn Ala Met Thr Glu Leu Lys Lys Lys Ser His Phe
    290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Ser Thr Ser
            340                 345                 350

Met Pro Ser Gly Asp Ala Phe Ser Val Gly Thr His Arg Phe Val
        355                 360                 365
```

```
Gln Lys Val Glu Glu Met Val Gln Asn His Met Thr Tyr Ser Leu Gln
    370                 375                 380
Asp Val Gly Gly Asp Ala Asn Trp Gln Leu Val Val Glu Glu Gly Glu
385                 390                 395                 400
Met Lys Val Tyr Arg Arg Glu Val Glu Glu Asn Gly Ile Val Leu Asp
                405                 410                 415
Pro Leu Lys Ala Thr His Ala Val Lys Gly Val Thr Gly His Glu Val
            420                 425                 430
Cys Asn Tyr Phe Trp Asn Val Asp Val Arg Asn Asp Trp Glu Thr Thr
        435                 440                 445
Ile Glu Asn Phe His Val Val Glu Thr Leu Ala Asp Asn Ala Ile Ile
    450                 455                 460
Ile Tyr Gln Thr His Lys Arg Val Trp Pro Ala Ser Gln Arg Asp Val
465                 470                 475                 480
Leu Tyr Leu Ser Ala Ile Arg Lys Ile Pro Ala Leu Asn Glu Asn Asp
                485                 490                 495
Pro Glu Thr Trp Ile Val Cys Asn Phe Ser Val Asp His Ser Ser Ala
            500                 505                 510
Pro Leu Asn Asn Arg Cys Val Arg Ala Lys Ile Asn Val Ala Met Ile
        515                 520                 525
Cys Gln Thr Leu Val Ser Pro Pro Glu Gly Asn Gln Glu Ile Ser Arg
    530                 535                 540
Asp Asn Ile Leu Cys Lys Ile Thr Tyr Val Ala Asn Val Asn Pro Gly
545                 550                 555                 560
Gly Trp Ala Pro Ala Ser Val Leu Arg Ala Val Ala Lys Arg Glu Tyr
                565                 570                 575
Pro Lys Phe Leu Lys Arg Phe Thr Ser Tyr Val Gln Glu Lys Thr Ala
            580                 585                 590
Gly Lys Pro Ile Leu Phe
        595

<210> SEQ ID NO 13
<211> LENGTH: 78
<212> TYPE: DNA
<213> ORGANISM: Homo sapiens
<220> FEATURE:
<221> NAME/KEY: CDS
<222> LOCATION: (1)..(78)

<400> SEQUENCE: 13 ccc tat agt cgc tct tcc tcc atg tct tcc att gat cta gtc agt gcc    48
Pro Tyr Ser Arg Ser Ser Ser Met Ser Ser Ile Asp Leu Val Ser Ala
  1               5                  10                  15 tct gat gat gtt cac aga ttc agc tcc cag                            78
Ser Asp Asp Val His Arg Phe Ser Ser Gln
             20                  25

<210> SEQ ID NO 14
<211> LENGTH: 26
<212> TYPE: PRT
<213> ORGANISM: Homo sapiens

<400> SEQUENCE: 14

Pro Tyr Ser Arg Ser Ser Ser Met Ser Ser Ile Asp Leu Val Ser Ala
  1               5                  10                  15

Ser Asp Asp Val His Arg Phe Ser Ser Gln
             20                  25
```

-continued

```
<210> SEQ ID NO 15
<211> LENGTH: 2034
<212> TYPE: DNA
<213> ORGANISM: Artificial Sequence
<220> FEATURE:
<223> OTHER INFORMATION: Description of Artificial Sequence: GPBPR3
<221> NAME/KEY: CDS
<222> LOCATION: (10)..(990)

<400> SEQUENCE: 15 gaattcacc atg gcc cca cta gcc gac tac aag gac gac gat gac aag atg        51
          Met Ala Pro Leu Ala Asp Tyr Lys Asp Asp Asp Asp Lys Met
          1               5                   10 tcg gat aat cag agc tgg aac tcg tcg ggc tcg gag gag gat cca gag         99
Ser Asp Asn Gln Ser Trp Asn Ser Ser Gly Ser Glu Glu Asp Pro Glu
15                  20                  25                  30 acg gag tct ggg ccg cct gtg gag cgc tgc ggg gtc ctc agt aag tgg        147
Thr Glu Ser Gly Pro Pro Val Glu Arg Cys Gly Val Leu Ser Lys Trp
                35                  40                  45 aca aac tac att cat ggg tgg cag gat cgt tgg gta gtt ttg aaa aat        195
Thr Asn Tyr Ile His Gly Trp Gln Asp Arg Trp Val Val Leu Lys Asn
            50                  55                  60 aat gct ctg agt tac tac aaa tct gaa gat gaa aca gag tat ggc tgc        243
Asn Ala Leu Ser Tyr Tyr Lys Ser Glu Asp Glu Thr Glu Tyr Gly Cys
        65                  70                  75 aga gga tcc atc tgt ctt agc aag gct gtc atc aca cct cac gat ttt        291
Arg Gly Ser Ile Cys Leu Ser Lys Ala Val Ile Thr Pro His Asp Phe
    80                  85                  90 gat gaa tgt cga ttt gat att agt gta aat gat agt gtt tgg tat ctt        339
Asp Glu Cys Arg Phe Asp Ile Ser Val Asn Asp Ser Val Trp Tyr Leu
95                  100                 105                 110 cgt gct cag gat cca gat cat aga cag caa tgg ata gat gcc att gaa        387
Arg Ala Gln Asp Pro Asp His Arg Gln Gln Trp Ile Asp Ala Ile Glu
                115                 120                 125 cag cac aag act gaa tct gga tat gga tct gaa tcc agc ttg cgt cga        435
Gln His Lys Thr Glu Ser Gly Tyr Gly Ser Glu Ser Ser Leu Arg Arg
            130                 135                 140 cat ggc tca atg gtg tcc ctg gtg tct gga gca agt ggc tac tct gca        483
His Gly Ser Met Val Ser Leu Val Ser Gly Ala Ser Gly Tyr Ser Ala
        145                 150                 155 aca tcc acc tct tca ttc aag aaa ggc cac agt tta cgt gag aag ttg        531
Thr Ser Thr Ser Ser Phe Lys Lys Gly His Ser Leu Arg Glu Lys Leu
    160                 165                 170 gct gaa atg gaa aca ttt aga gac atc tta tgt aga caa gtt gac acg        579
Ala Glu Met Glu Thr Phe Arg Asp Ile Leu Cys Arg Gln Val Asp Thr
175                 180                 185                 190 cta cag aag tac ttt gat gcc tgt gct gat gct gtc tct aag gat gaa        627
Leu Gln Lys Tyr Phe Asp Ala Cys Ala Asp Ala Val Ser Lys Asp Glu
                195                 200                 205 ctt caa agg gat aaa gtg gta gaa gat gat gaa gat gac ttt cct aca        675
Leu Gln Arg Asp Lys Val Val Glu Asp Asp Glu Asp Asp Phe Pro Thr
            210                 215                 220 acg cgt tct gat ggt gac ttc ttg cat agt acc aac ggc aat aaa gaa        723
Thr Arg Ser Asp Gly Asp Phe Leu His Ser Thr Asn Gly Asn Lys Glu
        225                 230                 235 aag tta ttt cca cat gtg aca cca aaa gga att aat ggt ata gac ttt        771
Lys Leu Phe Pro His Val Thr Pro Lys Gly Ile Asn Gly Ile Asp Phe
    240                 245                 250 aaa ggg gaa gcg ata act ttt aaa gca act act gct gga atc ctt gca        819
Lys Gly Glu Ala Ile Thr Phe Lys Ala Thr Thr Ala Gly Ile Leu Ala
255                 260                 265                 270
```

```
aca ctt tct cat tgt att gaa cta atg gtt aaa cgt gag gac agc tgg      867
Thr Leu Ser His Cys Ile Glu Leu Met Val Lys Arg Glu Asp Ser Trp
            275                 280                 285 cag aag aga ctg gat aag gaa act gag aag aaa aga aga aca gag gaa      915
Gln Lys Arg Leu Asp Lys Glu Thr Glu Lys Lys Arg Arg Thr Glu Glu
        290                 295                 300 gca tat aaa aat gca atg aca gaa cga aaa aat ccc act ttg gag gac      963
Ala Tyr Lys Asn Ala Met Thr Glu Arg Lys Asn Pro Thr Leu Glu Asp
            305                 310                 315 cag att atg aag aag gcc cta aca gtc tgattaatga agaagagttc            1010
Gln Ile Met Lys Lys Ala Leu Thr Val
        320                 325 tttgatgctg ttgaagctgc tcttgacaga caagataaaa tagaagaaca gtcacagagt   1070
gaaaaggtga gattacattg gcctacatcc ttgccctctg gagatgcctt ttcttctgtg   1130
gggacacata gatttgtcca aaagccctat agtcgctctt cctccatgtc ttccattgat   1190
ctagtcagtg cctctgatga tgttcacaga ttcagctccc aggttgaaga gatggtgcag   1250
aaccacatga cttactcatt acaggatgta ggcggagatg ccaattggca gttggttgta   1310
gaagaaggag aaatgaaggt atacagaaga gaagtagaag aaaatgggat tgttctggat   1370
cctttaaaag ctacccatgc agttaaaggc gtcacaggac atgaagtctg caattatttc   1430
tggaatgttg acgttcgcaa tgactgggaa acaactatag aaaactttca tgtggtggaa   1490
acattagctg ataatgcaat catcatttat caaacacaca gagggtgtg gcctgcttct    1550
cagcgagacg tattatatct ttctgtcatt cgaaagatac cagccttgac tgaaaatgac   1610
cctgaaactt ggatagtttg taattttct gtggatcatg acagtgctcc tctaaacaac    1670
cgatgtgtcc gtgccaaaat aaatgttgct atgatttgtc aaaccttggt aagcccacca   1730
gagggaaacc aggaaattag cagggacaac attctatgca agattacata tgtagctaat   1790
gtgaaccctg gaggatgggc accagcctca gtgttaaggg cagtggcaaa gcgagagtat   1850
cctaaatttc taaaacgttt tacttcttac gtccaagaaa aaactgcagg aaagcctatt   1910
ttgttctagt attaacaggt actagaagat atgttttatc tttttttaac tttatttgac   1970
taatatgact gtcaatacta aaatttagtt gttgaaagta tttactatgt tttttccgga   2030
attc                                                                2034

<210> SEQ ID NO 16
<211> LENGTH: 327
<212> TYPE: PRT
<213> ORGANISM: Artificial Sequence
<220> FEATURE:
<223> OTHER INFORMATION: Description of Artificial Sequence: GPBPR3

<400> SEQUENCE: 16

Met Ala Pro Leu Ala Asp Tyr Lys Asp Asp Asp Lys Met Ser Asp
 1               5                  10                  15

Asn Gln Ser Trp Asn Ser Ser Gly Ser Glu Glu Asp Pro Glu Thr Glu
            20                  25                  30

Ser Gly Pro Val Glu Arg Cys Gly Val Leu Ser Lys Trp Thr Asn
        35                  40                  45

Tyr Ile His Gly Trp Gln Asp Arg Trp Val Val Leu Lys Asn Asn Ala
    50                  55                  60

Leu Ser Tyr Tyr Lys Ser Glu Asp Glu Thr Glu Tyr Gly Cys Arg Gly
65                  70                  75                  80

Ser Ile Cys Leu Ser Lys Ala Val Ile Thr Pro His Asp Phe Asp Glu
                85                  90                  95
```

```
Cys Arg Phe Asp Ile Ser Val Asn Asp Ser Val Trp Tyr Leu Arg Ala
            100                 105                 110

Gln Asp Pro Asp His Arg Gln Gln Trp Ile Asp Ala Ile Glu Gln His
        115                 120                 125

Lys Thr Glu Ser Gly Tyr Gly Ser Glu Ser Ser Leu Arg Arg His Gly
    130                 135                 140

Ser Met Val Ser Leu Val Ser Gly Ala Ser Gly Tyr Ser Ala Thr Ser
145                 150                 155                 160

Thr Ser Ser Phe Lys Lys Gly His Ser Leu Arg Glu Lys Leu Ala Glu
                165                 170                 175

Met Glu Thr Phe Arg Asp Ile Leu Cys Arg Gln Val Asp Thr Leu Gln
            180                 185                 190

Lys Tyr Phe Asp Ala Cys Ala Asp Ala Val Ser Lys Asp Glu Leu Gln
        195                 200                 205

Arg Asp Lys Val Val Glu Asp Glu Asp Phe Pro Thr Thr Arg
    210                 215                 220

Ser Asp Gly Asp Phe Leu His Ser Thr Asn Gly Asn Lys Glu Lys Leu
225                 230                 235                 240

Phe Pro His Val Thr Pro Lys Gly Ile Asn Gly Ile Asp Phe Lys Gly
                245                 250                 255

Glu Ala Ile Thr Phe Lys Ala Thr Thr Ala Gly Ile Leu Ala Thr Leu
            260                 265                 270

Ser His Cys Ile Glu Leu Met Val Lys Arg Glu Asp Ser Trp Gln Lys
                275                 280                 285

Arg Leu Asp Lys Glu Thr Glu Lys Lys Arg Arg Thr Glu Glu Ala Tyr
    290                 295                 300

Lys Asn Ala Met Thr Glu Arg Lys Asn Pro Thr Leu Glu Asp Gln Ile
305                 310                 315                 320

Met Lys Lys Ala Leu Thr Val
                325

<210> SEQ ID NO 17
<211> LENGTH: 1978
<212> TYPE: DNA
<213> ORGANISM: Artificial Sequence
<220> FEATURE:
<223> OTHER INFORMATION: Description of Artificial Sequence:
      FLAG-GPBPDNLS
<221> NAME/KEY: CDS
<222> LOCATION: (10)..(1860)

<400> SEQUENCE: 17 gaattcacc atg gcc cca cta gcc gac tac aag gac gac gat gac aag atg     51
          Met Ala Pro Leu Ala Asp Tyr Lys Asp Asp Asp Asp Lys Met
           1               5                  10 tcg gat aat cag agc tgg aac tcg tcg ggc tcg gag gag gat cca gag     99
Ser Asp Asn Gln Ser Trp Asn Ser Ser Gly Ser Glu Glu Asp Pro Glu
 15                  20                  25                  30 acg gag tct ggg ccg cct gtg gag cgc tgc ggg gtc ctc agt aag tgg    147
Thr Glu Ser Gly Pro Pro Val Glu Arg Cys Gly Val Leu Ser Lys Trp
                 35                  40                  45 aca aac tac att cat ggg tgg cag gat cgt tgg gta gtt ttg aaa aat    195
Thr Asn Tyr Ile His Gly Trp Gln Asp Arg Trp Val Val Leu Lys Asn
             50                  55                  60 aat gct ctg agt tac tac aaa tct gaa gat gaa aca gag tat ggc tgc    243
Asn Ala Leu Ser Tyr Tyr Lys Ser Glu Asp Glu Thr Glu Tyr Gly Cys
         65                  70                  75
```

```
aga gga tcc atc tgt ctt agc aag gct gtc atc aca cct cac gat ttt      291
Arg Gly Ser Ile Cys Leu Ser Lys Ala Val Ile Thr Pro His Asp Phe
     80                  85                  90 gat gaa tgt cga ttt gat att agt gta aat gat agt gtt tgg tat ctt      339
Asp Glu Cys Arg Phe Asp Ile Ser Val Asn Asp Ser Val Trp Tyr Leu
 95                 100                 105                 110 cgt gct cag gat cca gat cat aga cag caa tgg ata gat gcc att gaa      387
Arg Ala Gln Asp Pro Asp His Arg Gln Gln Trp Ile Asp Ala Ile Glu
                    115                 120                 125 cag cac aag act gaa tct gga tat gga tct gaa tcc agc ttg cgt cga      435
Gln His Lys Thr Glu Ser Gly Tyr Gly Ser Glu Ser Ser Leu Arg Arg
                130                 135                 140 cat ggc tca atg gtg tcc ctg gtg tct gga gca agt ggc tac tct gca      483
His Gly Ser Met Val Ser Leu Val Ser Gly Ala Ser Gly Tyr Ser Ala
            145                 150                 155 aca tcc acc tct tca ttc aag aaa ggc cac agt tta cgt gag aag ttg      531
Thr Ser Thr Ser Ser Phe Lys Lys Gly His Ser Leu Arg Glu Lys Leu
        160                 165                 170 gct gaa atg gaa aca ttt aga gac atc tta tgt aga caa gtt gac acg      579
Ala Glu Met Glu Thr Phe Arg Asp Ile Leu Cys Arg Gln Val Asp Thr
175                 180                 185                 190 cta cag aag tac ttt gat gcc tgt gct gat gct gtc tct aag gat gaa      627
Leu Gln Lys Tyr Phe Asp Ala Cys Ala Asp Ala Val Ser Lys Asp Glu
                    195                 200                 205 ctt caa agg gat aaa gtg gta gaa gat gat gaa gat gac ttt cct aca      675
Leu Gln Arg Asp Lys Val Val Glu Asp Asp Glu Asp Asp Phe Pro Thr
                210                 215                 220 acg cgt tct gat ggt gac ttc ttg cat agt acc aac ggc aat aaa gaa      723
Thr Arg Ser Asp Gly Asp Phe Leu His Ser Thr Asn Gly Asn Lys Glu
            225                 230                 235 aag tta ttt cca cat gtg aca cca aaa gga att aat ggt ata gac ttt      771
Lys Leu Phe Pro His Val Thr Pro Lys Gly Ile Asn Gly Ile Asp Phe
        240                 245                 250 aaa ggg gaa gcg ata act ttt aaa gca act act gct gga atc ctt gca      819
Lys Gly Glu Ala Ile Thr Phe Lys Ala Thr Thr Ala Gly Ile Leu Ala
255                 260                 265                 270 aca ctt tct cat tgt att gaa cta atg gtt aaa cgt gag gac agc tgg      867
Thr Leu Ser His Cys Ile Glu Leu Met Val Lys Arg Glu Asp Ser Trp
                    275                 280                 285 cag aag aga ctg gat aag gaa act gag cac ttt gga gga cca gat tat      915
Gln Lys Arg Leu Asp Lys Glu Thr Glu His Phe Gly Gly Pro Asp Tyr
                290                 295                 300 gaa gaa ggc cct aac agt ctg att aat gaa gaa gag ttc ttt gat gct      963
Glu Glu Gly Pro Asn Ser Leu Ile Asn Glu Glu Glu Phe Phe Asp Ala
            305                 310                 315 gtt gaa gct gct ctt gac aga caa gat aaa ata gaa gaa cag tca cag     1011
Val Glu Ala Ala Leu Asp Arg Gln Asp Lys Ile Glu Glu Gln Ser Gln
        320                 325                 330 agt gaa aag gtg aga tta cat tgg cct aca tcc ttg ccc tct gga gat     1059
Ser Glu Lys Val Arg Leu His Trp Pro Thr Ser Leu Pro Ser Gly Asp
335                 340                 345                 350 gcc ttt tct tct gtg ggg aca cat aga ttt gtc caa aag ccc tat agt     1107
Ala Phe Ser Ser Val Gly Thr His Arg Phe Val Gln Lys Pro Tyr Ser
                    355                 360                 365 cgc tct tcc tcc atg tct tcc att gat cta gtc agt gcc tct gat gat     1155
Arg Ser Ser Ser Met Ser Ser Ile Asp Leu Val Ser Ala Ser Asp Asp
                370                 375                 380 gtt cac aga ttc agc tcc cag gtt gaa gag atg gtg cag aac cac atg     1203
Val His Arg Phe Ser Ser Gln Val Glu Glu Met Val Gln Asn His Met
            385                 390                 395
```

```
act tac tca tta cag gat gta ggc gga gat gcc aat tgg cag ttg gtt      1251
Thr Tyr Ser Leu Gln Asp Val Gly Gly Asp Ala Asn Trp Gln Leu Val
        400                 405                 410 gta gaa gaa gga gaa atg aag gta tac aga aga gaa gta gaa gaa aat      1299
Val Glu Glu Gly Glu Met Lys Val Tyr Arg Arg Glu Val Glu Glu Asn
415                 420                 425                 430 ggg att gtt ctg gat cct tta aaa gct acc cat gca gtt aaa ggc gtc      1347
Gly Ile Val Leu Asp Pro Leu Lys Ala Thr His Ala Val Lys Gly Val
                435                 440                 445 aca gga cat gaa gtc tgc aat tat ttc tgg aat gtt gac gtt cgc aat      1395
Thr Gly His Glu Val Cys Asn Tyr Phe Trp Asn Val Asp Val Arg Asn
            450                 455                 460 gac tgg gaa aca act ata gaa aac ttt cat gtg gtg gaa aca tta gct      1443
Asp Trp Glu Thr Thr Ile Glu Asn Phe His Val Val Glu Thr Leu Ala
        465                 470                 475 gat aat gca atc atc att tat caa aca cac aag agg gtg tgg cct gct      1491
Asp Asn Ala Ile Ile Ile Tyr Gln Thr His Lys Arg Val Trp Pro Ala
    480                 485                 490 tct cag cga gac gta tta tat ctt tct gtc att cga aag ata cca gcc      1539
Ser Gln Arg Asp Val Leu Tyr Leu Ser Val Ile Arg Lys Ile Pro Ala
495                 500                 505                 510 ttg act gaa aat gac cct gaa act tgg ata gtt tgt aat ttt tct gtg      1587
Leu Thr Glu Asn Asp Pro Glu Thr Trp Ile Val Cys Asn Phe Ser Val
                515                 520                 525 gat cat gac agt gct cct cta aac aac cga tgt gtc cgt gcc aaa ata      1635
Asp His Asp Ser Ala Pro Leu Asn Asn Arg Cys Val Arg Ala Lys Ile
            530                 535                 540 aat gtt gct atg att tgt caa acc ttg gta agc cca cca gag gga aac      1683
Asn Val Ala Met Ile Cys Gln Thr Leu Val Ser Pro Pro Glu Gly Asn
        545                 550                 555 cag gaa att agc agg gac aac att cta tgc aag att aca tat gta gct      1731
Gln Glu Ile Ser Arg Asp Asn Ile Leu Cys Lys Ile Thr Tyr Val Ala
    560                 565                 570 aat gtg aac cct gga gga tgg gca cca gcc tca gtg tta agg gca gtg      1779
Asn Val Asn Pro Gly Gly Trp Ala Pro Ala Ser Val Leu Arg Ala Val
575                 580                 585                 590 gca aag cga gag tat cct aaa ttt cta aaa cgt ttt act tct tac gtc      1827
Ala Lys Arg Glu Tyr Pro Lys Phe Leu Lys Arg Phe Thr Ser Tyr Val
                595                 600                 605 caa gaa aaa act gca gga aag cct att ttg ttc tagtattaac aggtactaga    1880
Gln Glu Lys Thr Ala Gly Lys Pro Ile Leu Phe
            610                 615 agatatgttt tatcttttt taactttatt tgactaatat gactgtcaat actaaaattt    1940
agttgttgaa agtatttact atgtttttc cggaattc                             1978

<210> SEQ ID NO 18
<211> LENGTH: 617
<212> TYPE: PRT
<213> ORGANISM: Artificial Sequence
<220> FEATURE:
<223> OTHER INFORMATION: Description of Artificial Sequence:
      FLAG-GPBPDNLS

<400> SEQUENCE: 18

Met Ala Pro Leu Ala Asp Tyr Lys Asp Asp Asp Asp Lys Met Ser Asp
 1               5                  10                  15

Asn Gln Ser Trp Asn Ser Ser Gly Ser Glu Glu Asp Pro Glu Thr Glu
            20                  25                  30

Ser Gly Pro Pro Val Glu Arg Cys Gly Val Leu Ser Lys Trp Thr Asn
```

-continued

```
                35                  40                  45
        Tyr Ile His Gly Trp Gln Asp Arg Trp Val Leu Lys Asn Asn Ala
                    50                  55                  60
        Leu Ser Tyr Tyr Lys Ser Glu Asp Glu Thr Glu Tyr Gly Cys Arg Gly
         65                  70                  75                  80
        Ser Ile Cys Leu Ser Lys Ala Val Ile Thr Pro His Asp Phe Asp Glu
                        85                  90                  95
        Cys Arg Phe Asp Ile Ser Val Asn Asp Ser Val Trp Tyr Leu Arg Ala
                    100                 105                 110
        Gln Asp Pro Asp His Arg Gln Gln Trp Ile Asp Ala Ile Glu Gln His
                    115                 120                 125
        Lys Thr Glu Ser Gly Tyr Gly Ser Glu Ser Ser Leu Arg Arg His Gly
                    130                 135                 140
        Ser Met Val Ser Leu Val Ser Gly Ala Ser Gly Tyr Ser Ala Thr Ser
        145                 150                 155                 160
        Thr Ser Ser Phe Lys Lys Gly His Ser Leu Arg Glu Lys Leu Ala Glu
                        165                 170                 175
        Met Glu Thr Phe Arg Asp Ile Leu Cys Arg Gln Val Asp Thr Leu Gln
                    180                 185                 190
        Lys Tyr Phe Asp Ala Cys Ala Asp Ala Val Ser Lys Asp Glu Leu Gln
                    195                 200                 205
        Arg Asp Lys Val Val Glu Asp Glu Asp Asp Phe Pro Thr Thr Arg
                    210                 215                 220
        Ser Asp Gly Asp Phe Leu His Ser Thr Asn Gly Asn Lys Glu Lys Leu
        225                 230                 235                 240
        Phe Pro His Val Thr Pro Lys Gly Ile Asn Gly Ile Asp Phe Lys Gly
                        245                 250                 255
        Glu Ala Ile Thr Phe Lys Ala Thr Thr Ala Gly Ile Leu Ala Thr Leu
                    260                 265                 270
        Ser His Cys Ile Glu Leu Met Val Lys Arg Glu Asp Ser Trp Gln Lys
                    275                 280                 285
        Arg Leu Asp Lys Glu Thr Glu His Phe Gly Gly Pro Asp Tyr Glu Glu
                    290                 295                 300
        Gly Pro Asn Ser Leu Ile Asn Glu Glu Glu Phe Phe Asp Ala Val Glu
        305                 310                 315                 320
        Ala Ala Leu Asp Arg Gln Asp Lys Ile Glu Glu Gln Ser Gln Ser Glu
                        325                 330                 335
        Lys Val Arg Leu His Trp Pro Thr Ser Leu Pro Ser Gly Asp Ala Phe
                    340                 345                 350
        Ser Ser Val Gly Thr His Arg Phe Val Gln Lys Pro Tyr Ser Arg Ser
                    355                 360                 365
        Ser Ser Met Ser Ser Ile Asp Leu Val Ser Ala Ser Asp Val His
                    370                 375                 380
        Arg Phe Ser Ser Gln Val Glu Met Val Gln Asn His Met Thr Tyr
        385                 390                 395                 400
        Ser Leu Gln Asp Val Gly Gly Asp Ala Asn Trp Gln Leu Val Val Glu
                        405                 410                 415
        Glu Gly Glu Met Lys Val Tyr Arg Arg Glu Val Glu Glu Asn Gly Ile
                    420                 425                 430
        Val Leu Asp Pro Leu Lys Ala Thr His Ala Val Lys Gly Val Thr Gly
                    435                 440                 445
        His Glu Val Cys Asn Tyr Phe Trp Asn Val Asp Val Arg Asn Asp Trp
        450                 455                 460
```

Glu Thr Thr Ile Glu Asn Phe His Val Val Glu Thr Leu Ala Asp Asn
465                 470                 475                 480

Ala Ile Ile Ile Tyr Gln Thr His Lys Arg Val Trp Pro Ala Ser Gln
            485                 490                 495

Arg Asp Val Leu Tyr Leu Ser Val Ile Arg Lys Ile Pro Ala Leu Thr
                500                 505                 510

Glu Asn Asp Pro Glu Thr Trp Ile Val Cys Asn Phe Ser Val Asp His
            515                 520                 525

Asp Ser Ala Pro Leu Asn Asn Arg Cys Val Arg Ala Lys Ile Asn Val
        530                 535                 540

Ala Met Ile Cys Gln Thr Leu Val Ser Pro Pro Glu Gly Asn Gln Glu
545                 550                 555                 560

Ile Ser Arg Asp Asn Ile Leu Cys Lys Ile Thr Tyr Val Ala Asn Val
                565                 570                 575

Asn Pro Gly Gly Trp Ala Pro Ala Ser Val Leu Arg Ala Val Ala Lys
            580                 585                 590

Arg Glu Tyr Pro Lys Phe Leu Lys Arg Phe Thr Ser Tyr Val Gln Glu
        595                 600                 605

Lys Thr Ala Gly Lys Pro Ile Leu Phe
610                 615

<210> SEQ ID NO 19
<211> LENGTH: 1975
<212> TYPE: DNA
<213> ORGANISM: Artificial Sequence
<220> FEATURE:
<223> OTHER INFORMATION: Description of Artificial Sequence:
      FLAG-GPBPDSXY
<221> NAME/KEY: CDS
<222> LOCATION: (10)..(1857)

<400> SEQUENCE: 19

```
gaattcacc atg gcc cca cta gcc gac tac aag gac gac gat gac aag atg      51
          Met Ala Pro Leu Ala Asp Tyr Lys Asp Asp Asp Asp Lys Met
           1               5                  10 tcg gat aat cag agc tgg aac tcg tcg ggc tcg gag gag gat cca gag      99
Ser Asp Asn Gln Ser Trp Asn Ser Ser Gly Ser Glu Glu Asp Pro Glu
 15                  20                  25                  30 acg gag tct ggg ccg cct gtg gag cgc tgc ggg gtc ctc agt aag tgg     147
Thr Glu Ser Gly Pro Pro Val Glu Arg Cys Gly Val Leu Ser Lys Trp
                 35                  40                  45 aca aac tac att cat ggg tgg cag gat cgt tgg gta gtt ttg aaa aat     195
Thr Asn Tyr Ile His Gly Trp Gln Asp Arg Trp Val Val Leu Lys Asn
             50                  55                  60 aat gct ctg agt tac tac aaa tct gaa gat gaa aca gag tat ggc tgc     243
Asn Ala Leu Ser Tyr Tyr Lys Ser Glu Asp Glu Thr Glu Tyr Gly Cys
         65                  70                  75 aga gga tcc atc tgt ctt agc aag gct gtc atc aca cct cac gat ttt     291
Arg Gly Ser Ile Cys Leu Ser Lys Ala Val Ile Thr Pro His Asp Phe
     80                  85                  90 gat gaa tgt cga ttt gat att agt gta aat gat agt gtt tgg tat ctt     339
Asp Glu Cys Arg Phe Asp Ile Ser Val Asn Asp Ser Val Trp Tyr Leu
 95                 100                 105                 110 cgt gct cag gat cca gat cat aga cag caa tgg ata gat gcc att gaa     387
Arg Ala Gln Asp Pro Asp His Arg Gln Gln Trp Ile Asp Ala Ile Glu
                115                 120                 125 cag cac aag act gaa tct gga tat gga tct gaa tcc agc ttg cgt cga     435
Gln His Lys Thr Glu Ser Gly Tyr Gly Ser Glu Ser Ser Leu Arg Arg
            130                 135                 140
```

-continued

| | | | | | | | | | | | | | | | |
|---|---|---|---|---|---|---|---|---|---|---|---|---|---|---|---|
| cat | ggc | aaa | ggc | cac | agt | tta | cgt | gag | aag | ttg | gct | gaa | atg | gaa | aca | 483 |
| His | Gly | Lys | Gly | His | Ser | Leu | Arg | Glu | Lys | Leu | Ala | Glu | Met | Glu | Thr |
| | | 145 | | | | 150 | | | | | 155 | | | | |
| ttt | aga | gac | atc | tta | tgt | aga | caa | gtt | gac | acg | cta | cag | aag | tac | ttt | 531 |
| Phe | Arg | Asp | Ile | Leu | Cys | Arg | Gln | Val | Asp | Thr | Leu | Gln | Lys | Tyr | Phe |
| | 160 | | | | | 165 | | | | | 170 | | | | |
| gat | gcc | tgt | gct | gat | gct | gtc | tct | aag | gat | gaa | ctt | caa | agg | gat | aaa | 579 |
| Asp | Ala | Cys | Ala | Asp | Ala | Val | Ser | Lys | Asp | Glu | Leu | Gln | Arg | Asp | Lys |
| 175 | | | | | 180 | | | | | 185 | | | | | 190 |
| gtg | gta | gaa | gat | gat | gaa | gat | gac | ttt | cct | aca | acg | cgt | tct | gat | ggt | 627 |
| Val | Val | Glu | Asp | Asp | Glu | Asp | Asp | Phe | Pro | Thr | Thr | Arg | Ser | Asp | Gly |
| | | | | 195 | | | | | 200 | | | | | 205 | |
| gac | ttc | ttg | cat | agt | acc | aac | ggc | aat | aaa | gaa | aag | tta | ttt | cca | cat | 675 |
| Asp | Phe | Leu | His | Ser | Thr | Asn | Gly | Asn | Lys | Glu | Lys | Leu | Phe | Pro | His |
| | | | | 210 | | | | | 215 | | | | | 220 | |
| gtg | aca | cca | aaa | gga | att | aat | ggt | ata | gac | ttt | aaa | ggg | gaa | gcg | ata | 723 |
| Val | Thr | Pro | Lys | Gly | Ile | Asn | Gly | Ile | Asp | Phe | Lys | Gly | Glu | Ala | Ile |
| | | 225 | | | | | 230 | | | | | 235 | | | |
| act | ttt | aaa | gca | act | act | gct | gga | atc | ctt | gca | aca | ctt | tct | cat | tgt | 771 |
| Thr | Phe | Lys | Ala | Thr | Thr | Ala | Gly | Ile | Leu | Ala | Thr | Leu | Ser | His | Cys |
| | 240 | | | | | 245 | | | | | 250 | | | | |
| att | gaa | cta | atg | gtt | aaa | cgt | gag | gac | agc | tgg | cag | aag | aga | ctg | gat | 819 |
| Ile | Glu | Leu | Met | Val | Lys | Arg | Glu | Asp | Ser | Trp | Gln | Lys | Arg | Leu | Asp |
| 255 | | | | | 260 | | | | | 265 | | | | | 270 |
| aag | gaa | act | gag | aag | aaa | aga | aga | aca | gag | gaa | gca | tat | aaa | aat | gca | 867 |
| Lys | Glu | Thr | Glu | Lys | Lys | Arg | Arg | Thr | Glu | Glu | Ala | Tyr | Lys | Asn | Ala |
| | | | | 275 | | | | | 280 | | | | | 285 | |
| atg | aca | gaa | ctt | aag | aaa | aaa | tcc | cac | ttt | gga | gga | cca | gat | tat | gaa | 915 |
| Met | Thr | Glu | Leu | Lys | Lys | Lys | Ser | His | Phe | Gly | Gly | Pro | Asp | Tyr | Glu |
| | | | | 290 | | | | | 295 | | | | | 300 | |
| gaa | ggc | cct | aac | agt | ctg | att | aat | gaa | gaa | gag | ttc | ttt | gat | gct | gtt | 963 |
| Glu | Gly | Pro | Asn | Ser | Leu | Ile | Asn | Glu | Glu | Glu | Phe | Phe | Asp | Ala | Val |
| | | | 305 | | | | | 310 | | | | | 315 | | |
| gaa | gct | gct | ctt | gac | aga | caa | gat | aaa | ata | gaa | gaa | cag | tca | cag | agt | 1011 |
| Glu | Ala | Ala | Leu | Asp | Arg | Gln | Asp | Lys | Ile | Glu | Glu | Gln | Ser | Gln | Ser |
| | | 320 | | | | | 325 | | | | | 330 | | | |
| gaa | aag | gtg | aga | tta | cat | tgg | cct | aca | tcc | ttg | ccc | tct | gga | gat | gcc | 1059 |
| Glu | Lys | Val | Arg | Leu | His | Trp | Pro | Thr | Ser | Leu | Pro | Ser | Gly | Asp | Ala |
| 335 | | | | | 340 | | | | | 345 | | | | | 350 |
| ttt | tct | tct | gtg | ggg | aca | cat | aga | ttt | gtc | caa | aag | ccc | tat | agt | cgc | 1107 |
| Phe | Ser | Ser | Val | Gly | Thr | His | Arg | Phe | Val | Gln | Lys | Pro | Tyr | Ser | Arg |
| | | | | 355 | | | | | 360 | | | | | 365 | |
| tct | tcc | tcc | atg | tct | tcc | att | gat | cta | gtc | agt | gcc | tct | gat | gat | gtt | 1155 |
| Ser | Ser | Ser | Met | Ser | Ser | Ile | Asp | Leu | Val | Ser | Ala | Ser | Asp | Asp | Val |
| | | | 370 | | | | | 375 | | | | | 380 | | |
| cac | aga | ttc | agc | tcc | cag | gtt | gaa | gag | atg | gtg | cag | aac | cac | atg | act | 1203 |
| His | Arg | Phe | Ser | Ser | Gln | Val | Glu | Glu | Met | Val | Gln | Asn | His | Met | Thr |
| | | 385 | | | | | 390 | | | | | 395 | | | |
| tac | tca | tta | cag | gat | gta | ggc | gga | gat | gcc | aat | tgg | cag | ttg | gtt | gta | 1251 |
| Tyr | Ser | Leu | Gln | Asp | Val | Gly | Gly | Asp | Ala | Asn | Trp | Gln | Leu | Val | Val |
| | 400 | | | | | 405 | | | | | 410 | | | | |
| gaa | gaa | gga | gaa | atg | aag | gta | tac | aga | aga | gaa | gta | gaa | gaa | aat | ggg | 1299 |
| Glu | Glu | Gly | Glu | Met | Lys | Val | Tyr | Arg | Arg | Glu | Val | Glu | Glu | Asn | Gly |
| 415 | | | | | 420 | | | | | 425 | | | | | 430 |
| att | gtt | ctg | gat | cct | tta | aaa | gct | acc | cat | gca | gtt | aaa | ggc | gtc | aca | 1347 |
| Ile | Val | Leu | Asp | Pro | Leu | Lys | Ala | Thr | His | Ala | Val | Lys | Gly | Val | Thr |
| | | | | 435 | | | | | 440 | | | | | 445 | |
| gga | cat | gaa | gtc | tgc | aat | tat | ttc | tgg | aat | gtt | gac | gtt | cgc | aat | gac | 1395 |
| Gly | His | Glu | Val | Cys | Asn | Tyr | Phe | Trp | Asn | Val | Asp | Val | Arg | Asn | Asp |

```
tgg gaa aca act ata gaa aac ttt cat gtg gtg gaa aca tta gct gat      1443
Trp Glu Thr Thr Ile Glu Asn Phe His Val Val Glu Thr Leu Ala Asp
            465                 470                 475 aat gca atc atc att tat caa aca cac aag agg gtg tgg cct gct tct      1491
Asn Ala Ile Ile Ile Tyr Gln Thr His Lys Arg Val Trp Pro Ala Ser
480                 485                 490 cag cga gac gta tta tat ctt tct gtc att cga aag ata cca gcc ttg      1539
Gln Arg Asp Val Leu Tyr Leu Ser Val Ile Arg Lys Ile Pro Ala Leu
495                 500                 505                 510 act gaa aat gac cct gaa act tgg ata gtt tgt aat ttt tct gtg gat      1587
Thr Glu Asn Asp Pro Glu Thr Trp Ile Val Cys Asn Phe Ser Val Asp
                515                 520                 525 cat gac agt gct cct cta aac aac cga tgt gtc cgt gcc aaa ata aat      1635
His Asp Ser Ala Pro Leu Asn Asn Arg Cys Val Arg Ala Lys Ile Asn
            530                 535                 540 gtt gct atg att tgt caa acc ttg gta agc cca cca gag gga aac cag      1683
Val Ala Met Ile Cys Gln Thr Leu Val Ser Pro Pro Glu Gly Asn Gln
        545                 550                 555 gaa att agc agg gac aac att cta tgc aag att aca tat gta gct aat      1731
Glu Ile Ser Arg Asp Asn Ile Leu Cys Lys Ile Thr Tyr Val Ala Asn
    560                 565                 570 gtg aac cct gga gga tgg gca cca gcc tca gtg tta agg gca gtg gca      1779
Val Asn Pro Gly Gly Trp Ala Pro Ala Ser Val Leu Arg Ala Val Ala
575                 580                 585                 590 aag cga gag tat cct aaa ttt cta aaa cgt ttt act tct tac gtc caa      1827
Lys Arg Glu Tyr Pro Lys Phe Leu Lys Arg Phe Thr Ser Tyr Val Gln
                595                 600                 605 gaa aaa act gca gga aag cct att ttg ttc tagtattaac aggtactaga        1877
Glu Lys Thr Ala Gly Lys Pro Ile Leu Phe
            610                 615 agatatgttt tatctttttt taactttatt tgactaatat gactgtcaat actaaaattt   1937
agttgttgaa agtatttact atgttttttc cggaattc                           1975

<210> SEQ ID NO 20
<211> LENGTH: 616
<212> TYPE: PRT
<213> ORGANISM: Artificial Sequence
<220> FEATURE:
<223> OTHER INFORMATION: Description of Artificial Sequence:
      FLAG-GPBPDSXY

<400> SEQUENCE: 20

Met Ala Pro Leu Ala Asp Tyr Lys Asp Asp Asp Lys Met Ser Asp
 1               5                  10                  15

Asn Gln Ser Trp Asn Ser Ser Gly Ser Glu Glu Asp Pro Glu Thr Glu
                20                  25                  30

Ser Gly Pro Pro Val Glu Arg Cys Gly Val Leu Ser Lys Trp Thr Asn
            35                  40                  45

Tyr Ile His Gly Trp Gln Asp Arg Trp Val Val Leu Lys Asn Asn Ala
        50                  55                  60

Leu Ser Tyr Tyr Lys Ser Glu Asp Glu Thr Glu Tyr Gly Cys Arg Gly
65                  70                  75                  80

Ser Ile Cys Leu Ser Lys Ala Val Ile Thr Pro His Asp Phe Asp Glu
                85                  90                  95

Cys Arg Phe Asp Ile Ser Val Asn Asp Ser Val Trp Tyr Leu Arg Ala
                100                 105                 110

Gln Asp Pro Asp His Arg Gln Gln Trp Ile Asp Ala Ile Glu Gln His
```

```
            115                 120                 125
Lys Thr Glu Ser Gly Tyr Gly Ser Glu Ser Ser Leu Arg Arg His Gly
    130                 135                 140

Lys Gly His Ser Leu Arg Glu Lys Leu Ala Met Glu Thr Phe Arg
145                 150                 155                 160

Asp Ile Leu Cys Arg Gln Val Asp Thr Leu Gln Lys Tyr Phe Asp Ala
                165                 170                 175

Cys Ala Asp Ala Val Ser Lys Asp Glu Leu Gln Arg Asp Lys Val Val
                180                 185                 190

Glu Asp Glu Asp Asp Phe Pro Thr Thr Arg Ser Asp Gly Asp Phe
                195                 200                 205

Leu His Ser Thr Asn Gly Asn Lys Glu Lys Leu Phe Pro His Val Thr
    210                 215                 220

Pro Lys Gly Ile Asn Gly Ile Asp Phe Lys Gly Glu Ala Ile Thr Phe
225                 230                 235                 240

Lys Ala Thr Thr Ala Gly Ile Leu Ala Thr Leu Ser His Cys Ile Glu
                245                 250                 255

Leu Met Val Lys Arg Glu Asp Ser Trp Gln Lys Arg Leu Asp Lys Glu
                260                 265                 270

Thr Glu Lys Lys Arg Arg Thr Glu Glu Ala Tyr Lys Asn Ala Met Thr
    275                 280                 285

Glu Leu Lys Lys Lys Ser His Phe Gly Gly Pro Asp Tyr Glu Glu Gly
    290                 295                 300

Pro Asn Ser Leu Ile Asn Glu Glu Glu Phe Phe Asp Ala Val Glu Ala
305                 310                 315                 320

Ala Leu Asp Arg Gln Asp Lys Ile Glu Glu Gln Ser Gln Ser Glu Lys
                325                 330                 335

Val Arg Leu His Trp Pro Thr Ser Leu Pro Ser Gly Asp Ala Phe Ser
                340                 345                 350

Ser Val Gly Thr His Arg Phe Val Gln Lys Pro Tyr Ser Arg Ser Ser
    355                 360                 365

Ser Met Ser Ser Ile Asp Leu Val Ser Ala Ser Asp Asp Val His Arg
    370                 375                 380

Phe Ser Ser Gln Val Glu Glu Met Val Gln Asn His Met Thr Tyr Ser
385                 390                 395                 400

Leu Gln Asp Val Gly Gly Asp Ala Asn Trp Gln Leu Val Val Glu Glu
                405                 410                 415

Gly Glu Met Lys Val Tyr Arg Arg Glu Val Glu Glu Asn Gly Ile Val
                420                 425                 430

Leu Asp Pro Leu Lys Ala Thr His Ala Val Lys Gly Val Thr Gly His
                435                 440                 445

Glu Val Cys Asn Tyr Phe Trp Asn Val Asp Val Arg Asn Asp Trp Glu
    450                 455                 460

Thr Thr Ile Glu Asn Phe His Val Val Glu Thr Leu Ala Asp Asn Ala
465                 470                 475                 480

Ile Ile Ile Tyr Gln Thr His Lys Arg Val Trp Pro Ala Ser Gln Arg
                485                 490                 495

Asp Val Leu Tyr Leu Ser Val Ile Arg Lys Ile Pro Ala Leu Thr Glu
                500                 505                 510

Asn Asp Pro Glu Thr Trp Ile Val Cys Asn Phe Ser Val Asp His Asp
                515                 520                 525

Ser Ala Pro Leu Asn Asn Arg Cys Val Arg Ala Lys Ile Asn Val Ala
    530                 535                 540
```

-continued

```
Met Ile Cys Gln Thr Leu Val Ser Pro Glu Gly Asn Gln Glu Ile
545                 550                 555                 560

Ser Arg Asp Asn Ile Leu Cys Lys Ile Thr Tyr Val Ala Asn Val Asn
                565                 570                 575

Pro Gly Gly Trp Ala Pro Ala Ser Val Leu Arg Ala Val Ala Lys Arg
            580                 585                 590

Glu Tyr Pro Lys Phe Leu Lys Arg Phe Thr Ser Tyr Val Gln Glu Lys
        595                 600                 605

Thr Ala Gly Lys Pro Ile Leu Phe
    610                 615
```

<210> SEQ ID NO 21
<211> LENGTH: 1915
<212> TYPE: DNA
<213> ORGANISM: Artificial Sequence
<220> FEATURE:
<223> OTHER INFORMATION: Description of Artificial Sequence: FLAG-GPBPDSXY/NLS
<221> NAME/KEY: CDS
<222> LOCATION: (10)..(1797)

<400> SEQUENCE: 21

```
gaattcacc atg gcc cca cta gcc gac tac aag gac gac gat gac aag atg    51
          Met Ala Pro Leu Ala Asp Tyr Lys Asp Asp Asp Asp Lys Met
          1               5                   10 tcg gat aat cag agc tgg aac tcg tcg ggc tcg gag gag gat cca gag     99
Ser Asp Asn Gln Ser Trp Asn Ser Ser Gly Ser Glu Glu Asp Pro Glu
 15                  20                  25                  30 acg gag tct ggg ccg cct gtg gag cgc tgc ggg gtc ctc agt aag tgg    147
Thr Glu Ser Gly Pro Pro Val Glu Arg Cys Gly Val Leu Ser Lys Trp
                 35                  40                  45 aca aac tac att cat ggg tgg cag gat cgt tgg gta gtt ttg aaa aat    195
Thr Asn Tyr Ile His Gly Trp Gln Asp Arg Trp Val Val Leu Lys Asn
             50                  55                  60 aat gct ctg agt tac tac aaa tct gaa gat gaa aca gag tat ggc tgc    243
Asn Ala Leu Ser Tyr Tyr Lys Ser Glu Asp Glu Thr Glu Tyr Gly Cys
 65                  70                  75 aga gga tcc atc tgt ctt agc aag gct gtc atc aca cct cac gat ttt    291
Arg Gly Ser Ile Cys Leu Ser Lys Ala Val Ile Thr Pro His Asp Phe
         80                  85                  90 gat gaa tgt cga ttt gat att agt gta aat gat agt gtt tgg tat ctt    339
Asp Glu Cys Arg Phe Asp Ile Ser Val Asn Asp Ser Val Trp Tyr Leu
 95                 100                 105                 110 cgt gct cag gat cca gat cat aga cag caa tgg ata gat gcc att gaa    387
Arg Ala Gln Asp Pro Asp His Arg Gln Gln Trp Ile Asp Ala Ile Glu
                115                 120                 125 cag cac aag act gaa tct gga tat gga tct gaa tcc agc ttg cgt cga    435
Gln His Lys Thr Glu Ser Gly Tyr Gly Ser Glu Ser Ser Leu Arg Arg
            130                 135                 140 cat ggc aaa ggc cac agt tta cgt gag aag ttg gct gaa atg gaa aca    483
His Gly Lys Gly His Ser Leu Arg Glu Lys Leu Ala Glu Met Glu Thr
        145                 150                 155 ttt aga gac atc tta tgt aga caa gtt gac acg cta cag aag tac ttt    531
Phe Arg Asp Ile Leu Cys Arg Gln Val Asp Thr Leu Gln Lys Tyr Phe
    160                 165                 170 gat gcc tgt gct gat gct gtc tct aag gat gaa ctt caa agg gat aaa    579
Asp Ala Cys Ala Asp Ala Val Ser Lys Asp Glu Leu Gln Arg Asp Lys
175                 180                 185                 190 gtg gta gaa gat gat gaa gat gac ttt cct aca acg cgt tct gat ggt    627
Val Val Glu Asp Asp Glu Asp Asp Phe Pro Thr Thr Arg Ser Asp Gly
```

```
                        195                     200                     205
gac ttc ttg cat agt acc aac ggc aat aaa gaa aag tta ttt cca cat         675
Asp Phe Leu His Ser Thr Asn Gly Asn Lys Glu Lys Leu Phe Pro His
                210                     215                     220 gtg aca cca aaa gga att aat ggt ata gac ttt aaa ggg gaa gcg ata         723
Val Thr Pro Lys Gly Ile Asn Gly Ile Asp Phe Lys Gly Glu Ala Ile
            225                     230                     235 act ttt aaa gca act act gct gga atc ctt gca aca ctt tct cat tgt        771
Thr Phe Lys Ala Thr Thr Ala Gly Ile Leu Ala Thr Leu Ser His Cys
        240                     245                     250 att gaa cta atg gtt aaa cgt gag gac agc tgg cag aag aga ctg gat        819
Ile Glu Leu Met Val Lys Arg Glu Asp Ser Trp Gln Lys Arg Leu Asp
255                     260                     265                     270 aag gaa act gag cac ttt gga gga cca gat tat gaa gaa ggc cct aac        867
Lys Glu Thr Glu His Phe Gly Gly Pro Asp Tyr Glu Glu Gly Pro Asn
                275                     280                     285 agt ctg att aat gaa gaa gag ttc ttt gat gct gtt gaa gct gct ctt        915
Ser Leu Ile Asn Glu Glu Glu Phe Phe Asp Ala Val Glu Ala Ala Leu
            290                     295                     300 gac aga caa gat aaa ata gaa gaa cag tca cag agt gaa aag gtg aga        963
Asp Arg Gln Asp Lys Ile Glu Glu Gln Ser Gln Ser Glu Lys Val Arg
        305                     310                     315 tta cat tgg cct aca tcc ttg ccc tct gga gat gcc ttt tct tct gtg       1011
Leu His Trp Pro Thr Ser Leu Pro Ser Gly Asp Ala Phe Ser Ser Val
320                     325                     330 ggg aca cat aga ttt gtc caa aag ccc tat agt cgc tct tcc tcc atg       1059
Gly Thr His Arg Phe Val Gln Lys Pro Tyr Ser Arg Ser Ser Ser Met
335                     340                     345                     350 tct tcc att gat cta gtc agt gcc tct gat gat gtt cac aga ttc agc       1107
Ser Ser Ile Asp Leu Val Ser Ala Ser Asp Asp Val His Arg Phe Ser
                355                     360                     365 tcc cag gtt gaa gag atg gtg cag aac cac atg act tac tca tta cag       1155
Ser Gln Val Glu Glu Met Val Gln Asn His Met Thr Tyr Ser Leu Gln
            370                     375                     380 gat gta ggc gga gat gcc aat tgg cag ttg gtt gta gaa gaa gga gaa       1203
Asp Val Gly Gly Asp Ala Asn Trp Gln Leu Val Val Glu Glu Gly Glu
        385                     390                     395 atg aag gta tac aga aga gaa gta gaa gaa aat ggg att gtt ctg gat       1251
Met Lys Val Tyr Arg Arg Glu Val Glu Glu Asn Gly Ile Val Leu Asp
400                     405                     410 cct tta aaa gct acc cat gca gtt aaa ggc gtc aca gga cat gaa gtc       1299
Pro Leu Lys Ala Thr His Ala Val Lys Gly Val Thr Gly His Glu Val
415                     420                     425                     430 tgc aat tat ttc tgg aat gtt gac gtt cgc aat gac tgg gaa aca act       1347
Cys Asn Tyr Phe Trp Asn Val Asp Val Arg Asn Asp Trp Glu Thr Thr
                435                     440                     445 ata gaa aac ttt cat gtg gtg gaa aca tta gct gat aat gca atc atc       1395
Ile Glu Asn Phe His Val Val Glu Thr Leu Ala Asp Asn Ala Ile Ile
            450                     455                     460 att tat caa aca cac aag agg gtg tgg cct gct tct cag cga gac gta       1443
Ile Tyr Gln Thr His Lys Arg Val Trp Pro Ala Ser Gln Arg Asp Val
        465                     470                     475 tta tat ctt tct gtc att cga aag ata cca gcc ttg act gaa aat gac       1491
Leu Tyr Leu Ser Val Ile Arg Lys Ile Pro Ala Leu Thr Glu Asn Asp
480                     485                     490 cct gaa act tgg ata gtt tgt aat ttt tct gtg gat cat gac agt gct       1539
Pro Glu Thr Trp Ile Val Cys Asn Phe Ser Val Asp His Asp Ser Ala
495                     500                     505                     510 cct cta aac aac cga tgt gtc cgt gcc aaa ata aat gtt gct atg att       1587
```

```
                                                                              -continued Pro Leu Asn Asn Arg Cys Val Arg Ala Lys Ile Asn Val Ala Met Ile
            515                 520                 525 tgt caa acc ttg gta agc cca cca gag gga aac cag gaa att agc agg      1635
Cys Gln Thr Leu Val Ser Pro Pro Glu Gly Asn Gln Glu Ile Ser Arg
            530                 535                 540 gac aac att cta tgc aag att aca tat gta gct aat gtg aac cct gga      1683
Asp Asn Ile Leu Cys Lys Ile Thr Tyr Val Ala Asn Val Asn Pro Gly
            545                 550                 555 gga tgg gca cca gcc tca gtg tta agg gca gtg gca aag cga gag tat      1731
Gly Trp Ala Pro Ala Ser Val Leu Arg Ala Val Ala Lys Arg Glu Tyr
        560                 565                 570 cct aaa ttt cta aaa cgt ttt act tct tac gtc caa gaa aaa act gca      1779
Pro Lys Phe Leu Lys Arg Phe Thr Ser Tyr Val Gln Glu Lys Thr Ala
575                 580                 585                 590 gga aag cct att ttg ttc tagtattaac aggtactaga agatatgttt             1827
Gly Lys Pro Ile Leu Phe
                595 tatcttttt taactttatt tgactaatat gactgtcaat actaaaattt agttgttgaa     1887
agtatttact atgttttttc cggaattc                                       1915

<210> SEQ ID NO 22
<211> LENGTH: 596
<212> TYPE: PRT
<213> ORGANISM: Artificial Sequence
<220> FEATURE:
<223> OTHER INFORMATION: Description of Artificial Sequence:
      FLAG-GPBPDSXY/NLS

<400> SEQUENCE: 22

Met Ala Pro Leu Ala Asp Tyr Lys Asp Asp Asp Asp Lys Met Ser Asp
  1               5                  10                  15

Asn Gln Ser Trp Asn Ser Ser Gly Ser Glu Glu Asp Pro Glu Thr Glu
                20                  25                  30

Ser Gly Pro Pro Val Glu Arg Cys Gly Val Leu Ser Lys Trp Thr Asn
            35                  40                  45

Tyr Ile His Gly Trp Gln Asp Arg Trp Val Val Leu Lys Asn Asn Ala
        50                  55                  60

Leu Ser Tyr Tyr Lys Ser Glu Asp Glu Thr Glu Tyr Gly Cys Arg Gly
 65                  70                  75                  80

Ser Ile Cys Leu Ser Lys Ala Val Ile Thr Pro His Asp Phe Asp Glu
                85                  90                  95

Cys Arg Phe Asp Ile Ser Val Asn Asp Ser Val Trp Tyr Leu Arg Ala
               100                 105                 110

Gln Asp Pro Asp His Arg Gln Gln Trp Ile Asp Ala Ile Glu Gln His
           115                 120                 125

Lys Thr Glu Ser Gly Tyr Gly Ser Glu Ser Ser Leu Arg Arg His Gly
       130                 135                 140

Lys Gly His Ser Leu Arg Glu Lys Leu Ala Glu Met Glu Thr Phe Arg
145                 150                 155                 160

Asp Ile Leu Cys Arg Gln Val Asp Thr Leu Gln Lys Tyr Phe Asp Ala
               165                 170                 175

Cys Ala Asp Ala Val Ser Lys Asp Glu Leu Gln Arg Asp Lys Val Val
           180                 185                 190

Glu Asp Asp Glu Asp Asp Phe Pro Thr Thr Arg Ser Asp Gly Asp Phe
       195                 200                 205

Leu His Ser Thr Asn Gly Asn Lys Glu Lys Leu Phe Pro His Val Thr
   210                 215                 220
```

Pro Lys Gly Ile Asn Gly Ile Asp Phe Lys Gly Glu Ala Ile Thr Phe
225                 230                 235                 240

Lys Ala Thr Thr Ala Gly Ile Leu Ala Thr Leu Ser His Cys Ile Glu
        245                 250                 255

Leu Met Val Lys Arg Glu Asp Ser Trp Gln Lys Arg Leu Asp Lys Glu
            260                 265                 270

Thr Glu His Phe Gly Gly Pro Asp Tyr Glu Glu Gly Pro Asn Ser Leu
        275                 280                 285

Ile Asn Glu Glu Glu Phe Phe Asp Ala Val Ala Ala Leu Asp Arg
    290                 295                 300

Gln Asp Lys Ile Glu Glu Gln Ser Gln Ser Glu Lys Val Arg Leu His
305                 310                 315                 320

Trp Pro Thr Ser Leu Pro Ser Gly Asp Ala Phe Ser Ser Val Gly Thr
                325                 330                 335

His Arg Phe Val Gln Lys Pro Tyr Ser Arg Ser Ser Met Ser Ser
            340                 345                 350

Ile Asp Leu Val Ser Ala Ser Asp Asp Val His Arg Phe Ser Ser Gln
        355                 360                 365

Val Glu Glu Met Val Gln Asn His Met Thr Tyr Ser Leu Gln Asp Val
    370                 375                 380

Gly Gly Asp Ala Asn Trp Gln Leu Val Val Glu Gly Glu Met Lys
385                 390                 395                 400

Val Tyr Arg Arg Glu Val Glu Glu Asn Gly Ile Val Leu Asp Pro Leu
                405                 410                 415

Lys Ala Thr His Ala Val Lys Gly Val Thr Gly His Glu Val Cys Asn
            420                 425                 430

Tyr Phe Trp Asn Val Asp Val Arg Asn Asp Trp Glu Thr Thr Ile Glu
        435                 440                 445

Asn Phe His Val Val Glu Thr Leu Ala Asp Asn Ala Ile Ile Ile Tyr
    450                 455                 460

Gln Thr His Lys Arg Val Trp Pro Ala Ser Gln Arg Asp Val Leu Tyr
465                 470                 475                 480

Leu Ser Val Ile Arg Lys Ile Pro Ala Leu Thr Glu Asn Asp Pro Glu
                485                 490                 495

Thr Trp Ile Val Cys Asn Phe Ser Val Asp His Asp Ser Ala Pro Leu
            500                 505                 510

Asn Asn Arg Cys Val Arg Ala Lys Ile Asn Val Ala Met Ile Cys Gln
        515                 520                 525

Thr Leu Val Ser Pro Pro Glu Gly Asn Gln Glu Ile Ser Arg Asp Asn
    530                 535                 540

Ile Leu Cys Lys Ile Thr Tyr Val Ala Asn Val Asn Pro Gly Gly Trp
545                 550                 555                 560

Ala Pro Ala Ser Val Leu Arg Ala Val Ala Lys Arg Glu Tyr Pro Lys
                565                 570                 575

Phe Leu Lys Arg Phe Thr Ser Tyr Val Gln Glu Lys Thr Ala Gly Lys
            580                 585                 590

Pro Ile Leu Phe
        595

<210> SEQ ID NO 23
<211> LENGTH: 2038
<212> TYPE: DNA
<213> ORGANISM: Artificial Sequence
<220> FEATURE:

<223> OTHER INFORMATION: Description of Artificial Sequence: GPBP-D169A
<221> NAME/KEY: CDS
<222> LOCATION: (10)..(1920)

<400> SEQUENCE: 23

```
gaattcacc atg gcc cca cta gcc gac tac aag gac gac gat gac aag atg        51
         Met Ala Pro Leu Ala Asp Tyr Lys Asp Asp Asp Asp Lys Met
           1               5                  10 tcg gat aat cag agc tgg aac tcg tcg ggc tcg gag gag gat cca gag          99
Ser Asp Asn Gln Ser Trp Asn Ser Ser Gly Ser Glu Glu Asp Pro Glu
 15                  20                  25                  30 acg gag tct ggg ccg cct gtg gag cgc tgc ggg gtc ctc agt aag tgg         147
Thr Glu Ser Gly Pro Pro Val Glu Arg Cys Gly Val Leu Ser Lys Trp
                 35                  40                  45 aca aac tac att cat ggg tgg cag gat cgt tgg gta gtt ttg aaa aat         195
Thr Asn Tyr Ile His Gly Trp Gln Asp Arg Trp Val Val Leu Lys Asn
             50                  55                  60 aat gct ctg agt tac tac aaa tct gaa gat gaa aca gag tat ggc tgc         243
Asn Ala Leu Ser Tyr Tyr Lys Ser Glu Asp Glu Thr Glu Tyr Gly Cys
         65                  70                  75 aga gga tcc atc tgt ctt agc aag gct gtc atc aca cct cac gat ttt         291
Arg Gly Ser Ile Cys Leu Ser Lys Ala Val Ile Thr Pro His Asp Phe
 80                  85                  90 gat gaa tgt cga ttt gat att agt gta aat gat agt gtt tgg tat ctt         339
Asp Glu Cys Arg Phe Asp Ile Ser Val Asn Asp Ser Val Trp Tyr Leu
 95                 100                 105                 110 cgt gct cag gat cca gat cat aga cag caa tgg ata gat gcc att gaa         387
Arg Ala Gln Asp Pro Asp His Arg Gln Gln Trp Ile Asp Ala Ile Glu
                115                 120                 125 cag cac aag act gaa tct gga tat gga tct gaa tcc agc ttg cgt cga         435
Gln His Lys Thr Glu Ser Gly Tyr Gly Ser Glu Ser Ser Leu Arg Arg
            130                 135                 140 cat ggc tca atg gtg tcc ctg gtg tct gga gca agt ggc tac tct gca         483
His Gly Ser Met Val Ser Leu Val Ser Gly Ala Ser Gly Tyr Ser Ala
145                 150                 155 aca tcc acc tct tca ttc aag aaa ggc cac agt tta cgt gag aag ttg         531
Thr Ser Thr Ser Ser Phe Lys Lys Gly His Ser Leu Arg Glu Lys Leu
        160                 165                 170 gct gaa atg gaa aca ttt aga gcc atc tta tgt aga caa gtt gac acg         579
Ala Glu Met Glu Thr Phe Arg Ala Ile Leu Cys Arg Gln Val Asp Thr
175                 180                 185                 190 cta cag aag tac ttt gat gcc tgt gct gat gct gtc tct aag gat gaa         627
Leu Gln Lys Tyr Phe Asp Ala Cys Ala Asp Ala Val Ser Lys Asp Glu
                195                 200                 205 ctt caa agg gat aaa gtg gta gaa gat gat gaa gat gac ttt cct aca         675
Leu Gln Arg Asp Lys Val Val Glu Asp Asp Glu Asp Asp Phe Pro Thr
            210                 215                 220 acg cgt tct gat ggt gac ttc ttg cat agt acc aac ggc aat aaa gaa         723
Thr Arg Ser Asp Gly Asp Phe Leu His Ser Thr Asn Gly Asn Lys Glu
        225                 230                 235 aag tta ttt cca cat gtg aca cca aaa gga att aat ggt ata gac ttt         771
Lys Leu Phe Pro His Val Thr Pro Lys Gly Ile Asn Gly Ile Asp Phe
    240                 245                 250 aaa ggg gaa gcg ata act ttt aaa gca act act gct gga atc ctt gca         819
Lys Gly Glu Ala Ile Thr Phe Lys Ala Thr Thr Ala Gly Ile Leu Ala
255                 260                 265                 270 aca ctt tct cat tgt att gaa cta atg gtt aaa cgt gag gac agc tgg         867
Thr Leu Ser His Cys Ile Glu Leu Met Val Lys Arg Glu Asp Ser Trp
                275                 280                 285 cag aag aga ctg gat aag gaa act gag aag aaa aga aga aca gag gaa         915
```

```
                Gln Lys Arg Leu Asp Lys Glu Thr Glu Lys Lys Arg Thr Glu Glu
                            290                 295                 300 gca tat aaa aat gca atg aca gaa ctt aag aaa aaa tcc cac ttt gga           963
Ala Tyr Lys Asn Ala Met Thr Glu Leu Lys Lys Lys Ser His Phe Gly
305                 310                 315 gga cca gat tat gaa gaa ggc cct aac agt ctg att aat gaa gaa gag          1011
Gly Pro Asp Tyr Glu Glu Gly Pro Asn Ser Leu Ile Asn Glu Glu Glu
    320                 325                 330 ttc ttt gat gct gtt gaa gct gct ctt gac aga caa gat aaa ata gaa          1059
Phe Phe Asp Ala Val Glu Ala Ala Leu Asp Arg Gln Asp Lys Ile Glu
335                 340                 345                 350 gaa cag tca cag agt gaa aag gtg aga tta cat tgg cct aca tcc ttg          1107
Glu Gln Ser Gln Ser Glu Lys Val Arg Leu His Trp Pro Thr Ser Leu
                355                 360                 365 ccc tct gga gat gcc ttt tct tct gtg ggg aca cat aga ttt gtc caa          1155
Pro Ser Gly Asp Ala Phe Ser Ser Val Gly Thr His Arg Phe Val Gln
            370                 375                 380 aag ccc tat agt cgc tct tcc tcc atg tct tcc att gat cta gtc agt          1203
Lys Pro Tyr Ser Arg Ser Ser Ser Met Ser Ser Ile Asp Leu Val Ser
        385                 390                 395 gcc tct gat gat gtt cac aga ttc agc tcc cag gtt gaa gag atg gtg          1251
Ala Ser Asp Asp Val His Arg Phe Ser Ser Gln Val Glu Glu Met Val
    400                 405                 410 cag aac cac atg act tac tca tta cag gat gta ggc gga gat gcc aat          1299
Gln Asn His Met Thr Tyr Ser Leu Gln Asp Val Gly Gly Asp Ala Asn
415                 420                 425                 430 tgg cag ttg gtt gta gaa gaa gga gaa atg aag gta tac aga aga gaa          1347
Trp Gln Leu Val Val Glu Glu Gly Glu Met Lys Val Tyr Arg Arg Glu
                435                 440                 445 gta gaa gaa aat ggg att gtt ctg gat cct tta aaa gct acc cat gca          1395
Val Glu Glu Asn Gly Ile Val Leu Asp Pro Leu Lys Ala Thr His Ala
            450                 455                 460 gtt aaa ggc gtc aca gga cat gaa gtc tgc aat tat ttc tgg aat gtt          1443
Val Lys Gly Val Thr Gly His Glu Val Cys Asn Tyr Phe Trp Asn Val
        465                 470                 475 gac gtt cgc aat gac tgg gaa aca act ata gaa aac ttt cat gtg gtg          1491
Asp Val Arg Asn Asp Trp Glu Thr Thr Ile Glu Asn Phe His Val Val
    480                 485                 490 gaa aca tta gct gat aat gca atc atc att tat caa aca cac aag agg          1539
Glu Thr Leu Ala Asp Asn Ala Ile Ile Ile Tyr Gln Thr His Lys Arg
495                 500                 505                 510 gtg tgg cct gct tct cag cga gac gta tta tat ctt tct gtc att cga          1587
Val Trp Pro Ala Ser Gln Arg Asp Val Leu Tyr Leu Ser Val Ile Arg
                515                 520                 525 aag ata cca gcc ttg act gaa aat gac cct gaa act tgg ata gtt tgt          1635
Lys Ile Pro Ala Leu Thr Glu Asn Asp Pro Glu Thr Trp Ile Val Cys
            530                 535                 540 aat ttt tct gtg gat cat gac agt gct cct cta aac aac cga tgt gtc          1683
Asn Phe Ser Val Asp His Asp Ser Ala Pro Leu Asn Asn Arg Cys Val
        545                 550                 555 cgt gcc aaa ata aat gtt gct atg att tgt caa acc ttg gta agc cca          1731
Arg Ala Lys Ile Asn Val Ala Met Ile Cys Gln Thr Leu Val Ser Pro
    560                 565                 570 cca gag gga aac cag gaa att agc agg gac aac att cta tgc aag att          1779
Pro Glu Gly Asn Gln Glu Ile Ser Arg Asp Asn Ile Leu Cys Lys Ile
575                 580                 585                 590 aca tat gta gct aat gtg aac cct gga gga tgg gca cca gcc tca gtg          1827
Thr Tyr Val Ala Asn Val Asn Pro Gly Gly Trp Ala Pro Ala Ser Val
                595                 600                 605
```

-continued

```
tta agg gca gtg gca aag cga gag tat cct aaa ttt cta aaa cgt ttt    1875
Leu Arg Ala Val Ala Lys Arg Glu Tyr Pro Lys Phe Leu Lys Arg Phe
        610                 615                 620 act tct tac gtc caa gaa aaa act gca gga aag cct att ttg ttc        1920
Thr Ser Tyr Val Gln Glu Lys Thr Ala Gly Lys Pro Ile Leu Phe
            625                 630                 635 tagtattaac aggtactaga agatatgttt tatctttttt taactttatt tgactaatat  1980
gactgtcaat actaaaattt agttgttgaa agtatttact atgttttttc cggaattc    2038

<210> SEQ ID NO 24
<211> LENGTH: 637
<212> TYPE: PRT
<213> ORGANISM: Artificial Sequence
<220> FEATURE:
<223> OTHER INFORMATION: Description of Artificial Sequence: GPBP-D169A

<400> SEQUENCE: 24

Met Ala Pro Leu Ala Asp Tyr Lys Asp Asp Asp Lys Met Ser Asp
  1               5                  10                  15

Asn Gln Ser Trp Asn Ser Ser Gly Ser Glu Glu Asp Pro Glu Thr Glu
                 20                  25                  30

Ser Gly Pro Pro Val Glu Arg Cys Gly Val Leu Ser Lys Trp Thr Asn
             35                  40                  45

Tyr Ile His Gly Trp Gln Asp Arg Trp Val Val Leu Lys Asn Asn Ala
         50                  55                  60

Leu Ser Tyr Tyr Lys Ser Glu Asp Glu Thr Glu Tyr Gly Cys Arg Gly
 65                  70                  75                  80

Ser Ile Cys Leu Ser Lys Ala Val Ile Thr Pro His Asp Phe Asp Glu
                     85                  90                  95

Cys Arg Phe Asp Ile Ser Val Asn Asp Ser Val Trp Tyr Leu Arg Ala
                100                 105                 110

Gln Asp Pro Asp His Arg Gln Gln Trp Ile Asp Ala Ile Glu Gln His
            115                 120                 125

Lys Thr Glu Ser Gly Tyr Gly Ser Glu Ser Ser Leu Arg Arg His Gly
        130                 135                 140

Ser Met Val Ser Leu Val Ser Gly Ala Ser Gly Tyr Ser Ala Thr Ser
145                 150                 155                 160

Thr Ser Ser Phe Lys Lys Gly His Ser Leu Arg Glu Lys Leu Ala Glu
                165                 170                 175

Met Glu Thr Phe Arg Ala Ile Leu Cys Arg Gln Val Asp Thr Leu Gln
            180                 185                 190

Lys Tyr Phe Asp Ala Cys Ala Asp Ala Val Ser Lys Asp Glu Leu Gln
        195                 200                 205

Arg Asp Lys Val Val Glu Asp Glu Asp Phe Pro Thr Thr Arg
    210                 215                 220

Ser Asp Gly Asp Phe Leu His Ser Thr Asn Gly Asn Lys Glu Lys Leu
225                 230                 235                 240

Phe Pro His Val Thr Pro Lys Gly Ile Asn Gly Ile Asp Phe Lys Gly
                245                 250                 255

Glu Ala Ile Thr Phe Lys Ala Thr Thr Ala Gly Ile Leu Ala Thr Leu
            260                 265                 270

Ser His Cys Ile Glu Leu Met Val Lys Arg Glu Asp Ser Trp Gln Lys
        275                 280                 285

Arg Leu Asp Lys Glu Thr Glu Lys Lys Arg Arg Thr Glu Glu Ala Tyr
    290                 295                 300
```

```
Lys Asn Ala Met Thr Glu Leu Lys Lys Ser His Phe Gly Gly Pro
305                 310                 315                 320

Asp Tyr Glu Glu Gly Pro Asn Ser Leu Ile Asn Glu Glu Phe Phe
            325                 330                 335

Asp Ala Val Glu Ala Ala Leu Asp Arg Gln Asp Lys Ile Glu Glu Gln
                340                 345                 350

Ser Gln Ser Glu Lys Val Arg Leu His Trp Pro Thr Ser Leu Pro Ser
        355                 360                 365

Gly Asp Ala Phe Ser Ser Val Gly Thr His Arg Phe Val Gln Lys Pro
    370                 375                 380

Tyr Ser Arg Ser Ser Ser Met Ser Ser Ile Asp Leu Val Ser Ala Ser
385                 390                 395                 400

Asp Asp Val His Arg Phe Ser Ser Gln Val Glu Glu Met Val Gln Asn
                405                 410                 415

His Met Thr Tyr Ser Leu Gln Asp Val Gly Gly Asp Ala Asn Trp Gln
            420                 425                 430

Leu Val Val Glu Glu Gly Glu Met Lys Val Tyr Arg Arg Glu Val Glu
                435                 440                 445

Glu Asn Gly Ile Val Leu Asp Pro Leu Lys Ala Thr His Ala Val Lys
    450                 455                 460

Gly Val Thr Gly His Glu Val Cys Asn Tyr Phe Trp Asn Val Asp Val
465                 470                 475                 480

Arg Asn Asp Trp Glu Thr Thr Ile Glu Asn Phe His Val Val Glu Thr
                485                 490                 495

Leu Ala Asp Asn Ala Ile Ile Ile Tyr Gln Thr His Lys Arg Val Trp
            500                 505                 510

Pro Ala Ser Gln Arg Asp Val Leu Tyr Leu Ser Val Ile Arg Lys Ile
        515                 520                 525

Pro Ala Leu Thr Glu Asn Asp Pro Glu Thr Trp Ile Val Cys Asn Phe
    530                 535                 540

Ser Val Asp His Asp Ser Ala Pro Leu Asn Asn Arg Cys Val Arg Ala
545                 550                 555                 560

Lys Ile Asn Val Ala Met Ile Cys Gln Thr Leu Val Ser Pro Pro Glu
                565                 570                 575

Gly Asn Gln Glu Ile Ser Arg Asp Asn Ile Leu Cys Lys Ile Thr Tyr
            580                 585                 590

Val Ala Asn Val Asn Pro Gly Gly Trp Ala Pro Ala Ser Val Leu Arg
        595                 600                 605

Ala Val Ala Lys Arg Glu Tyr Pro Lys Phe Leu Lys Arg Phe Thr Ser
    610                 615                 620

Tyr Val Gln Glu Lys Thr Ala Gly Lys Pro Ile Leu Phe
625                 630                 635

<210> SEQ ID NO 25
<211> LENGTH: 12482
<212> TYPE: DNA
<213> ORGANISM: Homo sapiens

<400> SEQUENCE: 25
tcgatcattt ccctcttcat attcagtgta tattgcacag atctctcaac aacacagcca    60
ttaaatagat attctccaag tgacacttac atcacacatg tttgagttta cgttacttgc   120
aaacataggg aaagaaagat acatgggata aactggtgca tgagaaatga gatcttagca   180
gttggttgaa ataaatgaga acaactgagg caaactaaag aggaagaagg gcaagtggca   240
```

-continued

```
gcttaacagg agtaagatga tgagatgaag ggcagaatac cttcatggag aggaggcaaa    300
gagatataca tgatatgttc ttaggaacat aactgaagca acaatgata ttatttctaa    360 ttatatataa acctgtgagt cagccttcca ggggcggcct gctaaggtag aatcattgga    420
atgatttggc cagggtttgg ataggagaga attggcagca gcgttaagat tgacccatga    480
taaataatgc tatgcaggta gcagggagtc tgactaggag caaaatcaac gaacttatcc    540
cttgcctaac atagtatctg tggagtcaga agaagaggt taaattggga tatctgaggc    600
aagtatcagg atttgccatg tctgcggagt agtttcataa ttctaatggt tataagcact    660
aaggcgttca ctaagtgaat gttggtagtt ccaggttata ttatccattc ttgagttaca    720
aaatacactt taaaaccttc ccatcttaat attatatgtt tttttagtca cagagtgaaa    780
aggtgagatt acattggcct acatccttgc cctctggaga tgccttttct tctgtgggga    840
cacatagatt tgtccaaaag gtaagctaat gtcagagttt actaaaagta caccttgtat    900
tgttcttcat tgttggtgga aatatctttt atttgagacg gagtctcact ctgtcaccag    960
agtggagtgc agtggcgcga tctcggctca ctacagtctc cacctcccgg gttcaagaga    1020
ttctcgtgcc tcagcctccc tggtagctgg gattacaggc atgtaccacc acacccagct    1080 aattttttgta ttttttaatgg agacagtttc accatggcca ggatggtctt gatctcctga    1140
ccttgtgatc cacccacctc agcctcccag agtgctggga ttacaggcgt gagccaccat    1200
gcccagccgg aaatatcttg tagtatataa gttttctccc cttttcatta atttaagtaa    1260
tgagactgtt tttggttta tatattgtat tccatataca tcctccaaaa cagttagaaa    1320
ttttgttctg aaaataaagt tctttcattt ttatttaagg ggaaagttgg gggtgggcaa    1380
ataaggagtg gctagtccaa aatagttaac cagaagtata tccagttata ctaaatctct    1440
ctcttctttg gggttaaatg gtattacttt gtattattgg aagcactaca ttctttttg    1500 gaatgatttt ggaacataat acataatagg tgcatgaagt cagcagttgc tgctgtgctt    1560
gtttcatata gtgctttgtt ttctcttccc tttatcttgt gtttggaagt tggtactgaa    1620
tgctctgttg tgcctttgtt ctgattactt ggttttttct ttgtctgtct ctggtagccc    1680
tatagtcgct cttcctccat gtcttccatt gatctagtca gtgcctctga tgatgttcac    1740
agattcagct cccaggtact gtatgaatgt atagagtgga cttgagtctt tctgtgctat    1800
atttcagcct gctttcccag ttcctagaaa tctttttggtt aggccactga ttttagttttt    1860 gaattttaaa tagtaacatt aagcattaaa aaggtcttcc ttgtctacta aatagttcct    1920
ctgtcaggtt tgcatgtgtc ctttactatt cacagcttgg aattttgtca tataggaggt    1980
actccagaaa gattttcaaa ctgaattgaa acaaatagaa gatactgggt tttgtatatc    2040
atgtaatatc tgtttcttca gtcaggattt agcagttttg atggacgtgg tccatatgat    2100
atgttatagc agaaaagcag attttttacaa gtctcacttt aaagcctaaa gtaccccaa    2160 ttaatattca acaaggaaat cacttttttaa taatatgttt catttccatt ataatactaa    2220
gctctattga gcagattgtg ttttcccttat gcaaattacc tttggatatt ataaatgaat    2280
atttctgttc atatgctaaa tctatggaaa tttgttttaa ttttttagcat tggtaagggt    2340 ttaggaattt aagacaggaa gctggatgct tgcggtctct aaagtctgta ccctcaaaat    2400
aaaatcagat taccattgga agaagttttt tttagtgtca gcgttagttc ttttttttaat    2460 tttcttaatc ttcacatctt tgccattcaa cttttttatct ttctggtgat tgcatttat    2520 tggactagat tatattatgt taatcttata ttaaagacct gagcactctg gtcagaatga    2580
ctcagtttaa accctggtta ggtgtatgat cccagtaagt tttctaactt ttttgtgctt    2640
```

```
cattttttatg atttagctag aacctgacac ataataagtg ctcaataaat gttaccttgt    2700
attgctatta taacataatt tctttgagct aataaaagtt atctacatca ttatttttc      2760 ctctgtgaga gtattgctat aaaagttttt aaaagtcata gtttaaagag atttctatta    2820
tttttatgtt tataaataaa gtttacatta gtttttaacc tgcaatagag aagaatatta    2880
agactttaat ttttctgact tgtacagcgt ttttctcctt gaatactctt aagaaaaaga    2940
tttagcaatt ctggatcaga aatcatccat aaccaaatat accacagtat attttaccttt   3000 ttgcttgtcc atttatgcat ttttttttaa ttttacttat ttattttcga gacagggtct    3060
tgctctgttg cccaggctgg agtgcagtgg cacgatctgg gctcactgca acctccatct    3120
cccaggttca gcaattctc ctgcctcagc ctcccaagta gctgggatta caggcacgca     3180
ccactatgcc cagctaattt ttgtattctt agtaaagacg gtttttcacc atgttggcca    3240
ggctggtcta gcactcctga cctcgtgatc tgcccacctc ggcctcccaa agtgctggga    3300
ttacaggtgt gagccaccat gcccggccct gcgtatgttt taaaaagag actcatattc     3360 ataatgaatc tgtgacaaaa ctacataata ctggggagact tggtttatt gtgctaagct    3420 ccacattgca ttaaaatcat atcacagact aatcaaaaat gcaggaatac ataggctata    3480
aatgaaagaa aatataatga cagcaaagaa agaatgtaag ccagtaataa agaatgccta    3540
agaattaggg gttcagaacc caaccaggg ccctcactgt agtgctgtag aacagctgaa      3600
ttgcttttaa gtccaggtaa ctatatcact gagaagcagg tgcctatatt tttacaaaat    3660
tttgctgaca gcttacttct tcgtaatatt aatacccttt tgtaaaactc atgtatgtaa    3720
cttgagagaa atcttgctgg attttttct ctaatatatg gtgctcatga ttgatcagat      3780
cctgttttag cctttgatta tgtactgttt tatatgccag aagaggtaaa aatgaagaaa    3840
ataacattaa ggtcttcaag tatttgttgt ccttgctaaa gcattagttg tcattagcag    3900
acgtggactc tagcaattca ctgttgtaat taaattgtgt gccttatgtt cagcagttcc    3960
tttataatag atgactaatt cccaattgat aagattttt gtttcagagg atgttacact      4020
gccttatcag ccattatcaa aggatctagc aagttgattc tgtatagtca cacttgagaa    4080
tatagcattg gatgtagatc tggagttaat attagttgag aaacattgtg ttatctggaa    4140
aactcttcca gttcaacaca gtgtaaaatt atagtagtga ctatacagta gtgttacatt    4200
ttacagttct cacaccctat agagactttt gtattaacaa ataagaggc tcaaaggtta     4260 ttcattaaca ttagaaacac ttatgttata ttacattgca tcggtctttt ctgtttttg     4320 tttttttttt tttttttgaga cggagtttcg cttttgttgc ccaggctgga gtgcaatggt   4380
acgatcttgg ctcactgcac cctctgcccc ctggattcaa gcgattctct tgcctcagcc    4440
acctgagtag ctgggattac aggcacctgc caccacaccc agctaatttt ttttcattt      4500 tagtagagat ggggtttcac catgttggcc aggctggtct cgaactcctg acctcaggtg    4560
atctgcccgc ctcggcctcc caaagtgctg ggattacagg catgagccgc cacacctggc    4620
ctacatcgtt cttaatacac aaatatacat cagttactcc acagcgcttg atatgggagg    4680
taaccaaatt ctttgtttta taatatcttc ataattaatt aaaaaactaa gtcgacattt    4740 ttaatcaccct ttaataattt gccaaaatat tatataagca taatataatc aattcttact   4800
tactccaaca aattttaaaa gtccagatac agataccata tctagttctct tgatcattta  4860 tatcagctcc catacagaag ccttctaaat ctctggtaat ttcactttgc tgtttatata    4920
agtgttggct catgactacc ttgttcttct tgaaatgatg ttttatagcc ttgaattggc    4980
```

```
tgaaataatc aagtgtacaa ttgagagatg ccctgaaaac agcttaaaat aaatatgta    5040 catctactag gaaattagta ccaacacatg aatctgtctg atgggcagat attaggaatg   5100
aagtcactcc agatctgaga aattaaagtt gtaaaggact gcaagttctg tgtttttgtt   5160
gttgttgttg ttgttgttgt tgtttgtttt ttcattttg ttttttgggt ttttttgaga    5220
cagagtctca ttctgtcacc caggctgtag tgcagtggca cgatctcaac tcactgcaac   5280
ctccgtctcc caggttcaag cgattctcct gtctcagctg ggattacagg cacacgctat   5340
cacacccagc taattttgt attttagta gagacagggt ttcaccatgt tagccaggct     5400
ggtctcgaac tcctgacctc aagtgatctg cccgtctcgg cctcccaaag tgctgggatt   5460
acaggcctga gacaccatgc ccagcatttt ttttttttt tttttttttt gtaaagagac    5520
aaggtttcac ttgtccaggc caagtgcagt ggcatgatca tagctctgta acctgacctc   5580
tgacctctga cttcctggac acaagtgatc ctcctgtctc tcagcctccc aagtagctgg   5640
gactacaggc attccaccac acccaactaa ttgtttttat ttttgtaga dacagggcct   5700 tgctatgttg cccaggctgg caagttcttg aaataatggc tgtggccaca actagaaaa   5760 taattttcag gtgtacagag aatagaaaga atttagattc ataaattgat catttttgttc  5820 acagttattt gcataacaca gttcacattt aaaggtgtca ccttagaaat caaaggggaa   5880
gaacatcatc ctctattgaa aaagaaagaa atcaaaggat gtacagtgaa tttgcagctt   5940
aatctatggg gagcatcatt gcaaaaaatg gttctgtgtg aggctctttc ccacccttg    6000 tccataggag cacattattg ttgtagtaat tatttcaccc ctctcccttt ttcagtgtac   6060
aagtgataca tgctaattt aacagaactt gaaagtagaa taaaattaaa ataatagttt    6120
actaatattc catttatctt ctctcatata tatgagataa atattaaggt gtatgtactt   6180
atccatatgt gcctgatttt ttaaaatcct tgtatatgca tctttgcacc cttatctaat   6240 tatttccta gaatatattc ctagaagcat aattgtggga acaaaggcca tgaacatttt    6300
caagtgttta ttttattatt ttattttatt tttattaatt ttgatacagg gttttgcttt   6360
gttccccaga ctggagtgca gtggtgagat caccactcac tgcaccttga cctcctggac   6420
tcaagcgatc cacctgcctc agtctcctca gtagcggggg ctaaggacta caggcacatg   6480
ccatcatgcc cagctaattt ttttatttgt agcagagacg aggtctcact gtgttgccca   6540
ggctgctatt ttatttattt tttaagagat agggtctcat tctgtcttcc aggctagaat   6600
gcagtggcac aatcatagct cactgcaacc tcaagcgatc tttgcctcag cctgagtagc   6660
tgggactaca ggcatgggcc accactctca gctaattttt ttttcaattt ttatttttt   6720 gtagatatgg gggtctcact gtgttgccta ggctggtctt gaaccccctag cctaaagtga  6780 tcttcccacc tcagcctccc aaagtgctag gattacaggc cacaggcctc agccaagttt  6840 taaaatttt tactgccaaa ctcttcatta gaaaagttga accagcttac attcccaggc   6900
cagttttcta ttgatatagt agcactgaat attataattc agttaacttt tgtcaatacg   6960
gtaggctaaa agtgctatgt tcttagccat ctctcttttg ggttaacagt gcactatttt  7020
gttattaata attattctat ctaacaagcc ccctctatgg ttttgtggct ttgtagtaag   7080
catagttgta tttccttttt tgaggtggag tcttgctatg ttgcccaggc tggagtgcag   7140
tggcgcgatc tcggctcact gcaccctccg cctcccgggt tcaagtgatt ctcctgcctc   7200
agactcctga gtatctggga ctacaggcat gcaccaccac gcccagctaa ttttttatat   7260
ttttagtaga gaggggagtt caccgtgtta gccgggatgg tctctatctc ttgacctcgt   7320
ggtccgcgtg cctcagcctc ccaaaatgct gtgattacag gcatgagcca ccctgcctgg   7380
```

```
ccaacatttc ttttacatgc ataaaagaga tctgagctgt ttttgagccc ttctagactt    7440 tcttttttt  ttttttttt  ttttttttt  ttttttttt  tttttttaa  gtagatgagg    7500 tcttgctatg ttgccgagac ttaacctcaa actcctaggc ccaagcaatc ctcccaagct    7560
gctgggacta caggcatgaa ccaccatgcc caacttagac ttttattgta ctatcaaaag    7620 gcaatttct  tttcaaattt ctgggtaata gtgttagaaa aatcctactt ggtaacatcc    7680
agaaatggca tcatactgag tgattcaaat gtgagatgga agaaaaggtt agaattggag    7740
tgaacgtccc ctcttatctc aaatgtattt tatctccatt ttgtttcata gtttattagt    7800
ttgaagatgc tttgaatgtc acctaatcat tttcaactct aggtccagaa aaatcaaggg    7860
catgatttct gaaattacac ttagcctaat taaaacttag aaacactgtt caccttcttc    7920 aatgttttg  actgagtctt tttcatttat aagtgacagg aggtgttact ataacattat    7980
ttcctagaat gtcaaatttt gagcctaata gcatggtaaa tttggctata tttgttgttt    8040
tttgtttttg ttttttttt  aatgaaactt agtatttcct tgtttcccac ttctttttt    8100 ttttttttt  ttttttttt  tgagacggag tctctctctg tcatccaggc tggagtgcaa    8160
tggcgtgatc ttggctcact gccacctccg cctcgcaggt tcacgctatt ctcctttcac    8220
agcctcctga gtagctggga ctacaggcac ccaccaccac gcccggccaa ttttttttgta   8280 tttttagtag agacggggtt ttaccatgtt aggcaggatg gtctcgaact cctgaccttg    8340
tgatctgccc gcctcagcct cccaaagtgc tgggattaca ggcgtgagcc accgcacctg    8400
gcctcccact tctttttaat atgtcgtgtc ataactgaac agtaaagtga gcagattatc    8460
aggttaaatc tgaagtgtca gtctggtcac cagtgcccaa gttactgccc ctatggtaat    8520
attggttact ttgtattttc ctacagcaaa cataaaattt gttatagtga gattttttacc   8580 tgtataccctc tcttaacttt aatgttatta cctcaaggaa gatattatca tgaatgaaga    8640
ttccatgatg aaagttttgc agagtttatt gcagtaattt agtacttcat tagaatcttt    8700
agttttttag gagcacagta ctgaatgttt gtttctttgt tggacctttt gaaaaccggt    8760
tttccattga tgcagtgtag ctgttacagg aatatcattt ttaaaacgtt tttatacagc    8820
atggctgaaa attgaacctg ggcctccctc gtggcctacc attgaaggaa cagcattttt    8880
tgcctatcta gaaagacaat gttaaatgtg ctatctatat attttttaac ttgtgctacc    8940
tactacgcgt ttatatttgt ggaatctgtt ttcttttgga caaaaccaca aatcaaaaac    9000
acctcatttc ttaggcattt gaaatcccta attcagaata atctcccaaa cagaaacaca    9060
actacctgca ttctttttga caaaagagct aagtagcatt agaaaattat tttaaaccca    9120
attctgtttt ttaacagaat aaaattcttc tgttcttcac attcttcttt cataggtaac    9180
ctattgaaag tagggtttat ttgggggaag catttctttc tgtctcttat ctcataataa    9240
atacaggtgt gcttaactac tagtttccta cctcaaagat atactcaaat ctaaagatgt    9300
ttaagatttt gggatctgaa gagtaaacat ttctcctaat cacaatgtga cagagacaaa    9360
tgaatcaagc caatgctact tttatttatg catactaact ggaacttttc tttttggaaa    9420
tcagatacat tttgtatgta ttagtaattt ggaatcctgc attggttatc ctcgccctcc    9480
caaagcagat tctgaaatta taaggtgca  caggttctcc atgcaacacc aaaagttata    9540
ttttccaagg ctttgtaaaa ttgtagaatg tcctgttaaa tttctgtcaa atcagtaact    9600
cacactgttt tgagaattat gaataaagga ataaatatt  gttagtgttt atttagtaca    9660
aaagtagatt atagaatctc agcattttg  tcaaaaaatt tcttttgat  gattgacaga    9720
```

```
tcaggagaca cttaaggcca tacctgcttt cagtaatcaa aaatgcattt aagatccaga   9780
aacttgaggt agcagaacat cactatcaca tataacatat cctttggtat agaaaattat   9840
attcccagag tgagtttctt ttttaaaacc attaatgagg ccaaggtggg aagatcactt   9900
gggaccagga gttcaagacc aagcctgggc cagatggcga gaccctgtct ctacaaaaaa   9960
ttaactggat gtggtggtgc actcctgtag tcccacctac tcagaggctg aggcaggagg  10020
atcccttgag cccaggaaat tgtagtggca gtgagctatg atcatactac tgtactgcag  10080
tctgggccac gaagtgagac cgtgtctctt aaaaaaaaaa aaatgttagg catggtggca  10140
caggcatata gttttagcta cttaggaggc tgaggcagga ggatcacttg agcccagaag  10200
ttcaagatta cagtgagtta tgattgtgcc gctgcactcc aacctgggtg acaaaataac  10260
cctgtctctg gcgggtaggg gggaagttga ttatttactt tgaaatatgt tcaaaactga  10320
ttcctgttct atattcctaa tgaacagaat agactttata taaacaaat agttaaactt  10380
aaggataaaa ttttaatgga agtataatat atatatcttc cagctcttct gtcttctaat  10440
gtatttatta cagaaaatga aattactttg tttccgcaat cttgtatca cttcagttct  10500
ccaataaatc tgagaattct ggtagtgtga aatattcagc tttctttgct tatttacata  10560
aaatgtataa ggacaattg tgataattaa gagttacatt taaatatcag gaaaagtta  10620
taaatttaaa ttaaaaatt ttaaaaggaa attattagaa attttaaaag aatgaactaa  10680
aaggtgatta tatgtaaatg cttgcatata tgaatattag cattgtcccc aaaataattt  10740
agaacaaaga aattggaatc aaataaataa aggtttgatt attttaaat tggcttatat  10800
tccatgataa aagagaggtt tatcagtggc ataagaaagg ttttcacct ttttgtatt  10860
gaaatctttg acatatacat atatatcttt gctcatcttt gtgtatcttt gctcgtatga  10920
gagcaaagat ataggcaaag atatgctctc tctctctatg tctttgttca taccaagacc  10980
ttcctgatat ctccacataa tcttaaatat aggaacatta gactggatga tctctgtgcc  11040
cccttatct ctactcttcc attattttat actttaacac atcatctctg ttttatgata  11100
taagaatgga atatttcttt tttcctgaaa atgcttattt tggtcacttg atacacatta  11160
ggccaatatg tgttacttga gtgacccatc ttccttcttt tcatttctgt ctcctgtcat  11220
taacctggat atctggaatg tggactaaac tcttcaaaca ctatgtaaaa cctactaacc  11280
tttgtgcatt tggttgctca gctactaaga gcaccatttc tgaactgaag ttaactgaag  11340
accattctgt tttagagatt atgacatacc ttttggattc tcatgccttt ttcctcccctt  11400
ctcaaggttg aagagatggt gcagaaccac atgacttact cattacagga tgtaggcgga  11460
gatgccaatt ggcagttggt tgtagaagaa ggagaaatga aggtaattcc ccctgaaatg  11520
ttatagattg ccaaaggcgt ctctgtttca gtcatattat cattactatt gatatgaata  11580
aggatagcac tttcaactta ccttttaaaac aaattattac atgtgatcaa agcagtacca  11640
tatattgagc aataaaatgt cttttttgctt ttctggcttt gcctttacta aaggtttta  11700
tgattataat ataaatatat gattaaacct ttctgttttg actaggccat gaagaaaata  11760
aaatttagag aattagatat gaccaggtca caattagctg atggtcctgt atttggatat  11820
ttccttttgt tttgttttttt taacatactg aatgttgtgc ctagatgaca ctttgtttct  11880
ctccctttt ggtctatacc ctccttcttt tcccttctct tactgcacct ttaattgata  11940
tttggacatt ggtcagttaa tcctggttac atccctaaac acatggacag aaaataagag  12000
cagggactga gagatacaga gatggattga aaagcaaaag caacattgaa ttttggattt  12060
tctcattcct aaggaactat gctaaataaa gatacaaaga taataagaca ctctccaagc  12120
```

-continued

```
taaagcttta gttaaggaaa aagaatattg acatttaaaa gatactattg gccaggcaca    12180
gtggctatgc ctgtaatccc agcactttta ggaggacatg gcaggcggat tacttgagct    12240
caggagttca agtcaaacct gggcaacacg gtgaaacccc gtctctacca aaaatacaaa    12300
aattagctgg gtgcagtacc acacacttgt agtcccagct acccaggagg ctgggcaaaa    12360
gattccttga gccagggagg tcaaggctgc aatgagccgc gtttgtgcca ctgcactcta    12420
gcctgggtca caaagtgaga ccctgtgtga gatatatata tatatatata tatatatata    12480
ta                                                                   12482
```

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: GPpep1

<400> SEQUENCE: 26

Lys Gly Lys Arg Gly Asp Ser Gly Ser Pro Ala Thr Trp Thr Thr Arg
 1               5                  10                  15

Gly Phe Val Phe Thr
            20

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: GPpep1Ala9

<400> SEQUENCE: 27

Lys Gly Lys Arg Gly Asp Ala Gly Ser Pro Ala Thr Trp Thr Thr Arg
 1               5                  10                  15

Gly Phe Val Phe Thr
            20

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence:
      ON-GPBP-54m

<400> SEQUENCE: 28
tcgaattcac catggcccca ctagccgact acaaggacga cgatgacaag              50

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence: ON-GPBP-55c

<400> SEQUENCE: 29
ccgagcccga cgagttccag ctctgattat ccgacatctt gtcatcgtcg              50

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence:

ON-HNC-B-N-14m

<400> SEQUENCE: 30
cgggatccgc tagctaagcc aggcaaggat gg                                32

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence:
        ON-HNC-B-N-16c

<400> SEQUENCE: 31
cgggatccat gcataaatag cagttctgct gt                                32

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: FLAG
        peptide

<400> SEQUENCE: 32

Asp Tyr Lys Asp Asp Asp Asp Lys
  1               5

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence:
        Hypothetical peptide

<400> SEQUENCE: 33

Pro Arg Ser Ala Arg Cys Gln Ala Arg Arg Arg Gly Gly Arg Thr
  1               5                  10                  15

Ser Ser

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: ON-GPBP-11m

<400> SEQUENCE: 34
gcgggactca gcggccggat tttct                                        25

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: ON-GPBP-15m

<400> SEQUENCE: 35
acagctggca gaagagac                                                18

<210> SEQ ID NO 36
<211> LENGTH: 18
<212> TYPE: DNA
<213> ORGANISM: Artificial Sequence
<220> FEATURE:

<223> OTHER INFORMATION: Description of Artificial Sequence: ON-GPBP-20c

<400> SEQUENCE: 36
catgggtagc ttttaaag                                                    18

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: ON-GPBP-22m

<400> SEQUENCE: 37
tagaagaaca gtcacagagt gaaaagg                                          27

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: ON-GPBP-53c

<400> SEQUENCE: 38
gaattcgaac aaaataggct ttc                                              23

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: ON-GPBP-56m

<400> SEQUENCE: 39
ccctatagtc gctcttc                                                     17

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: ON-GPBP-57c

<400> SEQUENCE: 40
ctgggagctg aatctgt                                                     17

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: ON-GPBP-62c

<400> SEQUENCE: 41
gtggttctgc accatctctt caac                                             24

<210> SEQ ID NO 42
<211> LENGTH: 41
<212> TYPE: DNA
<213> ORGANISM: Artificial Sequence
<220> FEATURE:
<223> OTHER INFORMATION: Description of Artificial Sequence: ON-GPBP-26

<400> SEQUENCE: 42
cacatagatt tgtccaaaag gttgaagaga tggtgcagaa c                          41

-continued

```
<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: GPIII
      derived peptide

<400> SEQUENCE: 43

Gln Arg Ala His Gly Gln Asp Leu Asp Ala Leu Phe Val Lys Val Leu
 1               5                  10                  15

Arg Ser Pro

<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: GPIII-IV-V
      derived peptide

<400> SEQUENCE: 44

Gln Arg Ala His Gly Gln Asp Leu Glu Ser Leu Phe His Gln
 1               5                  10

<210> SEQ ID NO 45
<211> LENGTH: 685
<212> TYPE: DNA
<213> ORGANISM: Artificial Sequence
<220> FEATURE:
<223> OTHER INFORMATION: Description of Artificial Sequence: GPDV
<221> NAME/KEY: CDS
<222> LOCATION: (1)..(633)

<400> SEQUENCE: 45 ggt ttg aaa gga aaa cgt gga gac agt gga tca cct gca acc tgg aca      48
Gly Leu Lys Gly Lys Arg Gly Asp Ser Gly Ser Pro Ala Thr Trp Thr
 1               5                  10                  15 acg aga ggc ttt gtc ttc acc cga cac agt caa acc aca gca att cct      96
Thr Arg Gly Phe Val Phe Thr Arg His Ser Gln Thr Thr Ala Ile Pro
                20                  25                  30 tca tgt cca gag ggg aca gtg cca ctc tac agt ggg ttt tct ttt ctt     144
Ser Cys Pro Glu Gly Thr Val Pro Leu Tyr Ser Gly Phe Ser Phe Leu
             35                  40                  45 ttt gta caa gga aat caa cga gcc cac gga caa gac ctt gga act ctt     192
Phe Val Gln Gly Asn Gln Arg Ala His Gly Gln Asp Leu Gly Thr Leu
         50                  55                  60 ggc agc tgc ctg cag cga ttt acc aca atg cca ttc tta ttc tgc aat     240
Gly Ser Cys Leu Gln Arg Phe Thr Thr Met Pro Phe Leu Phe Cys Asn
     65                  70                  75                  80 gtc aat gat gta tgt aat ttt gca tct cga aat gat tat tca tac tgg     288
Val Asn Asp Val Cys Asn Phe Ala Ser Arg Asn Asp Tyr Ser Tyr Trp
                 85                  90                  95 ctg tca aca cca gct ctg atg cca atg aac atg gct ccc att act ggc     336
Leu Ser Thr Pro Ala Leu Met Pro Met Asn Met Ala Pro Ile Thr Gly
            100                 105                 110 aga gcc ctt gag cct tat ata agc aga tgc act gtt tgt gaa ggt cct     384
Arg Ala Leu Glu Pro Tyr Ile Ser Arg Cys Thr Val Cys Glu Gly Pro
        115                 120                 125 gcg atc gcc ata gcc gtt cac agc caa acc act gac att cct cca tgt     432
Ala Ile Ala Ile Ala Val His Ser Gln Thr Thr Asp Ile Pro Pro Cys
    130                 135                 140 cct cac ggc tgg att tct ctc tgg aaa gga ttt tca ttc atc atg aaa     480
Pro His Gly Trp Ile Ser Leu Trp Lys Gly Phe Ser Phe Ile Met Lys
```

```
                    145                 150                 155                 160
gcc tat tcc atc aac tgt gaa agc tgg gga att aga aaa aat aat aag       528
Ala Tyr Ser Ile Asn Cys Glu Ser Trp Gly Ile Arg Lys Asn Asn Lys
                165                 170                 175 tcg ctg tca ggt gtg cat gaa gaa aag aca ctg aag cta aaa aag aca       576
Ser Leu Ser Gly Val His Glu Glu Lys Thr Leu Lys Leu Lys Lys Thr
            180                 185                 190 gca gaa ctg cta ttt ttc atc cta aag aac aaa gta atg aca gaa cat       624
Ala Glu Leu Leu Phe Phe Ile Leu Lys Asn Lys Val Met Thr Glu His
        195                 200                 205 gct gtt att taggtatttt tctttaacca aacaatattg ctccatgatg               673
Ala Val Ile
    210 acttagtaca aa                                                         685

<210> SEQ ID NO 46
<211> LENGTH: 211
<212> TYPE: PRT
<213> ORGANISM: Artificial Sequence
<220> FEATURE:
<223> OTHER INFORMATION: Description of Artificial Sequence: GPDV

<400> SEQUENCE: 46

Gly Leu Lys Gly Lys Arg Gly Asp Ser Gly Ser Pro Ala Thr Trp Thr
 1               5                  10                  15

Thr Arg Gly Phe Val Phe Thr Arg His Ser Gln Thr Thr Ala Ile Pro
                20                  25                  30

Ser Cys Pro Glu Gly Thr Val Pro Leu Tyr Ser Gly Phe Ser Phe Leu
            35                  40                  45

Phe Val Gln Gly Asn Gln Arg Ala His Gly Gln Asp Leu Gly Thr Leu
        50                  55                  60

Gly Ser Cys Leu Gln Arg Phe Thr Thr Met Pro Phe Leu Phe Cys Asn
    65                  70                  75                  80

Val Asn Asp Val Cys Asn Phe Ala Ser Arg Asn Asp Tyr Ser Tyr Trp
                85                  90                  95

Leu Ser Thr Pro Ala Leu Met Pro Met Asn Met Ala Pro Ile Thr Gly
            100                 105                 110

Arg Ala Leu Glu Pro Tyr Ile Ser Arg Cys Thr Val Cys Glu Gly Pro
        115                 120                 125

Ala Ile Ala Ile Ala Val His Ser Gln Thr Thr Asp Ile Pro Pro Cys
    130                 135                 140

Pro His Gly Trp Ile Ser Leu Trp Lys Gly Phe Ser Phe Ile Met Lys
145                 150                 155                 160

Ala Tyr Ser Ile Asn Cys Glu Ser Trp Gly Ile Arg Lys Asn Asn Lys
                165                 170                 175

Ser Leu Ser Gly Val His Glu Glu Lys Thr Leu Lys Leu Lys Lys Thr
            180                 185                 190

Ala Glu Leu Leu Phe Phe Ile Leu Lys Asn Lys Val Met Thr Glu His
        195                 200                 205

Ala Val Ile
    210

<210> SEQ ID NO 47
<211> LENGTH: 680
<212> TYPE: DNA
<213> ORGANISM: Artificial Sequence
<220> FEATURE:
<223> OTHER INFORMATION: Description of Artificial Sequence: GPDIII
```

<221> NAME/KEY: CDS
<222> LOCATION: (1)..(216)

<400> SEQUENCE: 47

| | | | | | | | | | | | | | | | | |
|---|---|---|---|---|---|---|---|---|---|---|---|---|---|---|---|---|
| ggt | ttg | aaa | gga | aaa | cgt | gga | gac | agt | gga | tca | cct | gca | acc | tgg | aca | 48 |
| Gly | Leu | Lys | Gly | Lys | Arg | Gly | Asp | Ser | Gly | Ser | Pro | Ala | Thr | Trp | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| acg | aga | ggc | ttt | gtc | ttc | acc | cga | cac | agt | caa | acc | aca | gca | att | cct | 96 |
| Thr | Arg | Gly | Phe | Val | Phe | Thr | Arg | His | Ser | Gln | Thr | Thr | Ala | Ile | Pro | |
| | | | | 20 | | | | | 25 | | | | | 30 | | |

| | | | | | | | | | | | | | | | | |
|---|---|---|---|---|---|---|---|---|---|---|---|---|---|---|---|---|
| tca | tgt | cca | gag | ggg | aca | gtg | cca | ctc | tac | agt | ggg | ttt | tct | ttt | ctt | 144 |
| Ser | Cys | Pro | Glu | Gly | Thr | Val | Pro | Leu | Tyr | Ser | Gly | Phe | Ser | Phe | Leu | |
| | | | | 35 | | | | | 40 | | | | | 45 | | |

| | | | | | | | | | | | | | | | | |
|---|---|---|---|---|---|---|---|---|---|---|---|---|---|---|---|---|
| ttt | gta | caa | gga | aat | caa | cga | gcc | cac | gga | caa | gac | ctt | gat | gca | ctg | 192 |
| Phe | Val | Gln | Gly | Asn | Gln | Arg | Ala | His | Gly | Gln | Asp | Leu | Asp | Ala | Leu | |
| | | | | 50 | | | | | 55 | | | | | 60 | | |

| | | | | | | | | | |
|---|---|---|---|---|---|---|---|---|---|
| ttt | gtg | aag | gtc | ctg | cga | tcg | cca | tagccgttca cagccaaacc actgacattc | 246 |
| Phe | Val | Lys | Val | Leu | Arg | Ser | Pro | | |
| 65 | | | | | 70 | | | | |

| | |
|---|---|
| ctccatgtcc tcacggctgg atttctctct ggaaaggatt ttcattcatc atgttcacaa | 306 |
| gtgcaggttc tgagggcacc gggcaagcac tggcctcccc tggctcctgc ctggaagaat | 366 |
| tccgagccag cccatttcta gaatgtcatg gaagaggaac gtgcaactac tattcaaatt | 426 |
| cctacagttt ctggctggct tcattaaacc cagaaagaat gttcagaaag cctattccat | 486 |
| caactgtgaa agctggggaa ttagaaaaaa taataagtcg ctgtcaggtg tgcatgaaga | 546 |
| aaagacactg aagctaaaaa agacagcaga actgctattt ttcatcctaa agaacaaagt | 606 |
| aatgacagaa catgctgtta tttaggtatt tttctttaac caaacaatat tgctccatga | 666 |
| tgacttagta caaa | 680 |

<210> SEQ ID NO 48
<211> LENGTH: 72
<212> TYPE: PRT
<213> ORGANISM: Artificial Sequence
<220> FEATURE:
<223> OTHER INFORMATION: Description of Artificial Sequence: GPDIII

<400> SEQUENCE: 48

| | | | | | | | | | | | | | | | |
|---|---|---|---|---|---|---|---|---|---|---|---|---|---|---|---|
| Gly | Leu | Lys | Gly | Lys | Arg | Gly | Asp | Ser | Gly | Ser | Pro | Ala | Thr | Trp | Thr |
| 1 | | | | 5 | | | | | 10 | | | | | 15 | |

| | | | | | | | | | | | | | | | |
|---|---|---|---|---|---|---|---|---|---|---|---|---|---|---|---|
| Thr | Arg | Gly | Phe | Val | Phe | Thr | Arg | His | Ser | Gln | Thr | Thr | Ala | Ile | Pro |
| | | | | 20 | | | | | 25 | | | | | 30 | |

| | | | | | | | | | | | | | | | |
|---|---|---|---|---|---|---|---|---|---|---|---|---|---|---|---|
| Ser | Cys | Pro | Glu | Gly | Thr | Val | Pro | Leu | Tyr | Ser | Gly | Phe | Ser | Phe | Leu |
| | | | | 35 | | | | | 40 | | | | | 45 | |

| | | | | | | | | | | | | | | | |
|---|---|---|---|---|---|---|---|---|---|---|---|---|---|---|---|
| Phe | Val | Gln | Gly | Asn | Gln | Arg | Ala | His | Gly | Gln | Asp | Leu | Asp | Ala | Leu |
| | | | | 50 | | | | | 55 | | | | | 60 | |

| | | | | | | | |
|---|---|---|---|---|---|---|---|
| Phe | Val | Lys | Val | Leu | Arg | Ser | Pro |
| 65 | | | | | 70 | | |

<210> SEQ ID NO 49
<211> LENGTH: 392
<212> TYPE: DNA
<213> ORGANISM: Artificial Sequence
<220> FEATURE:
<223> OTHER INFORMATION: Description of Artificial Sequence: GPDIII-IV-V
<221> NAME/KEY: CDS
<222> LOCATION: (1)..(204)

<400> SEQUENCE: 49

| | | | | | | | | | | | | | | | | |
|---|---|---|---|---|---|---|---|---|---|---|---|---|---|---|---|---|
| ggt | ttg | aaa | gga | aaa | cgt | gga | gac | agt | gga | tca | cct | gca | acc | tgg | aca | 48 |

```
Gly Leu Lys Gly Lys Arg Gly Asp Ser Gly Ser Pro Ala Thr Trp Thr
 1               5                  10                  15 acg aga ggc ttt gtc ttc acc cga cac agt caa acc aca gca att cct    96
Thr Arg Gly Phe Val Phe Thr Arg His Ser Gln Thr Thr Ala Ile Pro
             20                  25                  30 tca tgt cca gag ggg aca gtg cca ctc tac agt ggg ttt tct ttt ctt    144
Ser Cys Pro Glu Gly Thr Val Pro Leu Tyr Ser Gly Phe Ser Phe Leu
         35                  40                  45 ttt gta caa gga aat caa cga gcc cac gga caa gac ctt gaa agc cta    192
Phe Val Gln Gly Asn Gln Arg Ala His Gly Gln Asp Leu Glu Ser Leu
     50                  55                  60 ttc cat caa ctg tgaaagctgg ggaattagaa aaaataataa gtcgctgtca        244
Phe His Gln Leu
 65 ggtgtgcatg aagaaaagac actgaagcta aaaagacag cagaactgct attttcatc    304 ctaaagaaca agtaatgac agaacatgct gttatttagg tattttctt taaccaaaca    364 atattgctcc atgatgactt agtacaaa                                     392

<210> SEQ ID NO 50
<211> LENGTH: 68
<212> TYPE: PRT
<213> ORGANISM: Artificial Sequence
<220> FEATURE:
<223> OTHER INFORMATION: Description of Artificial Sequence: GPDIII-IV-V

<400> SEQUENCE: 50

Gly Leu Lys Gly Lys Arg Gly Asp Ser Gly Ser Pro Ala Thr Trp Thr
 1               5                  10                  15

Thr Arg Gly Phe Val Phe Thr Arg His Ser Gln Thr Thr Ala Ile Pro
             20                  25                  30

Ser Cys Pro Glu Gly Thr Val Pro Leu Tyr Ser Gly Phe Ser Phe Leu
         35                  40                  45

Phe Val Gln Gly Asn Gln Arg Ala His Gly Gln Asp Leu Glu Ser Leu
     50                  55                  60

Phe His Gln Leu
 65

<210> SEQ ID NO 51
<211> LENGTH: 507
<212> TYPE: DNA
<213> ORGANISM: Artificial Sequence
<220> FEATURE:
<223> OTHER INFORMATION: Description of Artificial Sequence: GPDIII-V
<221> NAME/KEY: CDS
<222> LOCATION: (1)..(216)

<400> SEQUENCE: 51 ggt ttg aaa gga aaa cgt gga gac agt gga tca cct gca acc tgg aca    48
Gly Leu Lys Gly Lys Arg Gly Asp Ser Gly Ser Pro Ala Thr Trp Thr
 1               5                  10                  15 acg aga ggc ttt gtc ttc acc cga cac agt caa acc aca gca att cct    96
Thr Arg Gly Phe Val Phe Thr Arg His Ser Gln Thr Thr Ala Ile Pro
             20                  25                  30 tca tgt cca gag ggg aca gtg cca ctc tac agt ggg ttt tct ttt ctt    144
Ser Cys Pro Glu Gly Thr Val Pro Leu Tyr Ser Gly Phe Ser Phe Leu
         35                  40                  45 ttt gta caa gga aat caa cga gcc cac gga caa gac ctt gat gca ctg    192
Phe Val Gln Gly Asn Gln Arg Ala His Gly Gln Asp Leu Asp Ala Leu
     50                  55                  60 ttt gtg aag gtc ctg cga tcg cca tagccgttca cagccaaacc actgacattc   246
```

```
Phe Val Lys Val Leu Arg Ser Pro
 65                  70 ctccatgtcc tcacggctgg atttctctct ggaaaggatt ttcattcatc atgaaagcct   306
attccatcaa ctgtgaaagc tggggaatta gaaaaaataa taagtcgctg tcaggtgtgc   366
atgaagaaaa gacactgaag ctaaaaaaga cagcagaact gctatttttc atcctaaaga   426
acaaagtaat gacagaacat gctgttattt aggtattttt ctttaaccaa acaatattgc   486
tccatgatga cttagtacaa a                                             507
```

<210> SEQ ID NO 52
<211> LENGTH: 72
<212> TYPE: PRT
<213> ORGANISM: Artificial Sequence
<220> FEATURE:
<223> OTHER INFORMATION: Description of Artificial Sequence: GPDIII-V

<400> SEQUENCE: 52

```
Gly Leu Lys Gly Lys Arg Gly Asp Ser Gly Ser Pro Ala Thr Trp Thr
 1               5                  10                  15

Thr Arg Gly Phe Val Phe Thr Arg His Ser Gln Thr Thr Ala Ile Pro
            20                  25                  30

Ser Cys Pro Glu Gly Thr Val Pro Leu Tyr Ser Gly Phe Ser Phe Leu
        35                  40                  45

Phe Val Gln Gly Asn Gln Arg Ala His Gly Gln Asp Leu Asp Ala Leu
     50                  55                  60

Phe Val Lys Val Leu Arg Ser Pro
 65                  70
```

<210> SEQ ID NO 53
<211> LENGTH: 659
<212> TYPE: DNA
<213> ORGANISM: Artificial Sequence
<220> FEATURE:
<223> OTHER INFORMATION: Description of Artificial Sequence: HMBP-21
<221> NAME/KEY: CDS
<222> LOCATION: (37)..(627)

<400> SEQUENCE: 53

```
gaaacagtg cagccacctc cgagagcctg gatgtg atg gcg tca cag aag aga      54
                                        Met Ala Ser Gln Lys Arg
                                         1               5 ccc tcc cag agg cac gga tcc aag tac ctg gcc aca gca agt acc atg    102
Pro Ser Gln Arg His Gly Ser Lys Tyr Leu Ala Thr Ala Ser Thr Met
             10                  15                  20 gac cat gcc agg cat ggc ttc ctc cca agg cac aga gac acg ggc atc    150
Asp His Ala Arg His Gly Phe Leu Pro Arg His Arg Asp Thr Gly Ile
         25                  30                  35 ctt gac tcc atc ggg cgc ttc ttt ggc ggt gac agg ggt gcg cca aag    198
Leu Asp Ser Ile Gly Arg Phe Phe Gly Gly Asp Arg Gly Ala Pro Lys
     40                  45                  50 cgg ggc tct ggc aag gta ccc tgg cta aag ccg ggc cgg agc cct ctg    246
Arg Gly Ser Gly Lys Val Pro Trp Leu Lys Pro Gly Arg Ser Pro Leu
 55                  60                  65                  70 ccc tct cat gcc cgc agc cag cct ggg ctg tgc aac atg tac aag gac    294
Pro Ser His Ala Arg Ser Gln Pro Gly Leu Cys Asn Met Tyr Lys Asp
             75                  80                  85 tca cac cac ccg gca aga act gct cac tat ggc tcc ctg ccc cag aag    342
Ser His His Pro Ala Arg Thr Ala His Tyr Gly Ser Leu Pro Gln Lys
         90                  95                 100 tca cac ggc cgg acc caa gat gaa aac ccc gta gtc cac ttc ttc aag    390
```

```
Ser His Gly Arg Thr Gln Asp Glu Asn Pro Val Val His Phe Phe Lys
        105                 110                 115 aac att gtg acg cct cgc aca cca ccc ccg tcg cag gga aag ggg aga      438
Asn Ile Val Thr Pro Arg Thr Pro Pro Pro Ser Gln Gly Lys Gly Arg
120                 125                 130 gga ctg tcc ctg agc aga ttt agc tgg ggg gcc gaa ggc cag aga cca      486
Gly Leu Ser Leu Ser Arg Phe Ser Trp Gly Ala Glu Gly Gln Arg Pro
135                 140                 145                 150 gga ttt ggc tac gga ggc aga gcg tcc gac tat aaa tcg gct cac aag      534
Gly Phe Gly Tyr Gly Gly Arg Ala Ser Asp Tyr Lys Ser Ala His Lys
                155                 160                 165 gga ttc aag gga gtc gat gcc cag ggc acg ctt tcc aaa att ttt aag      582
Gly Phe Lys Gly Val Asp Ala Gln Gly Thr Leu Ser Lys Ile Phe Lys
        170                 175                 180 ctg gga gga aga gat agt cgc tct gga tca ccc atg gct aga cgc          627
Leu Gly Gly Arg Asp Ser Arg Ser Gly Ser Pro Met Ala Arg Arg
        185                 190                 195 tgaaaaccca cctggttccg gaatcctgtc ct                                  659

<210> SEQ ID NO 54
<211> LENGTH: 197
<212> TYPE: PRT
<213> ORGANISM: Artificial Sequence
<220> FEATURE:
<223> OTHER INFORMATION: Description of Artificial Sequence: HMBP-21

<400> SEQUENCE: 54

Met Ala Ser Gln Lys Arg Pro Ser Gln Arg His Gly Ser Lys Tyr Leu
 1               5                  10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140

Ala Glu Gly Gln Arg Pro Gly Phe Gly Tyr Gly Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg
        195

<210> SEQ ID NO 55
<211> LENGTH: 12
<212> TYPE: DNA
<213> ORGANISM: Homo sapiens
```

<400> SEQUENCE: 55
ttttagtcac ag                                                               12

<210> SEQ ID NO 56
<211> LENGTH: 12
<212> TYPE: DNA
<213> ORGANISM: Homo sapiens

<400> SEQUENCE: 56
caaaaggtaa gc                                                               12

<210> SEQ ID NO 57
<211> LENGTH: 12
<212> TYPE: DNA
<213> ORGANISM: Homo sapiens

<400> SEQUENCE: 57
tggtagccct at                                                               12

<210> SEQ ID NO 58
<211> LENGTH: 12
<212> TYPE: DNA
<213> ORGANISM: Homo sapiens

<400> SEQUENCE: 58
tcccaggtac tg                                                               12

<210> SEQ ID NO 59
<211> LENGTH: 12
<212> TYPE: DNA
<213> ORGANISM: Homo sapiens

<400> SEQUENCE: 59
ctcaaggttg aa                                                               12

<210> SEQ ID NO 60
<211> LENGTH: 12
<212> TYPE: DNA
<213> ORGANISM: Homo sapiens

<400> SEQUENCE: 60
atgaaggtaa tt                                                               12

<210> SEQ ID NO 61
<211> LENGTH: 72
<212> TYPE: PRT
<213> ORGANISM: Homo sapiens

<400> SEQUENCE: 61

Gly Leu Lys Gly Lys Arg Gly Asp Ser Gly Ser Pro Ala Thr Trp Thr
 1               5                  10                  15

Thr Arg Gly Phe Val Phe Thr Arg His Ser Gln Thr Thr Ala Ile Pro
                20                  25                  30

Ser Cys Pro Glu Gly Pro Val Pro Leu Tyr Ser Gly Phe Ser Phe Leu
            35                  40                  45

Phe Val Gln Gly Asn Gln Arg Ala His Gly Gln Asp Leu Asp Ala Leu
        50                  55                  60

Phe Val Lys Val Leu Arg Ser Pro
    65                  70

```
<210> SEQ ID NO 62
<211> LENGTH: 69
<212> TYPE: PRT
<213> ORGANISM: Homo sapiens

<400> SEQUENCE: 62

Met Ala Ser Gln Lys Arg Pro Ser Gln Arg His Gly Ser Lys Tyr Leu
 1               5                  10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro
65

<210> SEQ ID NO 63
<211> LENGTH: 5
<212> TYPE: PRT
<213> ORGANISM: Homo sapiens

<400> SEQUENCE: 63

Lys Arg Gly Asp Ser
 1               5
```